US008663962B2

(12) United States Patent
Zhang et al.

(10) Patent No.: US 8,663,962 B2
(45) Date of Patent: Mar. 4, 2014

(54) PENTOSE FERMENTATION BY A RECOMBINANT MICROORGANISM

(75) Inventors: Xiyun Zhang, Fremont, CA (US); Ryan C. Fong, Redwood City, CA (US); Ezhilkani Subbian, Mountain View, CA (US)

(73) Assignee: Codexis, Inc., Redwood City, CA (US)

( * ) Notice: Subject to any disclaimer, the term of this patent is extended or adjusted under 35 U.S.C. 154(b) by 44 days.

(21) Appl. No.: 13/429,710

(22) Filed: Mar. 26, 2012

(65) Prior Publication Data

US 2012/0252074 A1     Oct. 4, 2012

Related U.S. Application Data

(60) Provisional application No. 61/469,505, filed on Mar. 30, 2011, provisional application No. 61/496,152, filed on Jun. 13, 2011.

(51) Int. Cl.
*C12N 9/04*     (2006.01)
*C12N 9/02*     (2006.01)
*C12P 19/02*    (2006.01)
*C07H 21/04*    (2006.01)
*C07K 1/00*     (2006.01)

(52) U.S. Cl.
USPC .......... 435/190; 435/189; 435/105; 536/23.2; 530/350

(58) Field of Classification Search
USPC .......... 435/190, 189, 105; 536/23.2; 530/350
See application file for complete search history.

(56) References Cited

U.S. PATENT DOCUMENTS

| | | | |
|---|---|---|---|
| 4,486,553 A | 12/1984 | Wesch | |
| 5,605,793 A | 2/1997 | Stemmer | |
| 5,811,238 A | 9/1998 | Stemmer et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,928,905 A | 7/1999 | Stemmer et al. | |
| 6,096,548 A | 8/2000 | Stemmer | |
| 6,117,679 A | 9/2000 | Stemmer | |
| 6,132,970 A | 10/2000 | Stemmer | |
| 6,165,793 A | 12/2000 | Stemmer | |
| 6,180,406 B1 | 1/2001 | Stemmer | |
| 6,251,674 B1 | 6/2001 | Tobin et al. | |
| 6,277,638 B1 | 8/2001 | Stemmer | |
| 6,287,861 B1 | 9/2001 | Stemmer et al. | |
| 6,287,862 B1 | 9/2001 | delCardayre et al. | |
| 6,291,242 B1 | 9/2001 | Stemmer | |
| 6,297,053 B1 | 10/2001 | Stemmer | |
| 6,303,344 B1 | 10/2001 | Patten et al. | |
| 6,309,883 B1 | 10/2001 | Minshull et al. | |
| 6,319,713 B1 | 11/2001 | Patten et al. | |
| 6,319,714 B1 | 11/2001 | Crameri et al. | |
| 6,323,030 B1 | 11/2001 | Stemmer | |
| 6,326,204 B1 | 12/2001 | delCardayre et al. | |
| 6,335,160 B1 | 1/2002 | Patten et al. | |
| 6,335,198 B1 | 1/2002 | delCardayre et al. | |
| 6,344,356 B1 | 2/2002 | Stemmer | |
| 6,352,859 B1 | 3/2002 | delCardayre et al. | |
| 6,355,484 B1 | 3/2002 | Patten et al. | |
| 6,358,740 B1 | 3/2002 | Patten et al. | |
| 6,358,742 B1 | 3/2002 | Stemmer | |
| 6,365,377 B1 | 4/2002 | Patten et al. | |
| 6,365,408 B1 | 4/2002 | Stemmer | |
| 6,368,861 B1 | 4/2002 | Crameri et al. | |
| 6,372,497 B1 | 4/2002 | Stemmer | |
| 6,376,246 B1 | 4/2002 | Crameri et al. | |
| 6,379,964 B1 | 4/2002 | delCardayre et al. | |
| 6,387,702 B1 | 5/2002 | Stemmer | |
| 6,391,552 B2 | 5/2002 | Stemmer | |
| 6,391,640 B1 | 5/2002 | Minshull et al. | |
| 6,395,547 B1 | 5/2002 | Stemmer | |
| 6,406,855 B1 | 6/2002 | Patten et al. | |
| 6,406,910 B1 | 6/2002 | Patten et al. | |
| 6,413,745 B1 | 7/2002 | Patten et al. | |
| 6,413,774 B1 | 7/2002 | Stemmer | |
| 6,420,175 B1 | 7/2002 | Stemmer | |
| 6,423,542 B1 | 7/2002 | Crameri et al. | |
| 6,426,224 B1 | 7/2002 | Crameri et al. | |
| 6,436,675 B1 | 8/2002 | Welch et al. | |
| 6,444,468 B1 | 9/2002 | Stemmer et al. | |
| 6,455,253 B1 | 9/2002 | Patten et al. | |
| 6,479,652 B1 | 11/2002 | Crameri et al. | |
| 6,482,647 B1 | 11/2002 | Stemmer | |
| 6,489,146 B2 | 12/2002 | Stemmer et al. | |
| 6,506,602 B1 | 1/2003 | Stemmer | |
| 6,506,603 B1 | 1/2003 | Stemmer | |

(Continued)

FOREIGN PATENT DOCUMENTS

EP     0 137 280 B1     3/1992
WO     93/03159 A1      2/1993

(Continued)

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Altschul, S.F., et al., "Gapped BLAST and PSI-BLAST: a new generation of protein database search programs," Nucleic Acids Res., 25(17):3389-3402 [1997].

(Continued)

*Primary Examiner* — Ganapathirama Raghu
(74) *Attorney, Agent, or Firm* — Codexis, Inc.

(57) ABSTRACT

The present invention provides methods and compositions suitable for use in the conversion of xylose to xylitol and xylulose, including nucleic acid constructs, recombinant fungal host cells, and related materials.

4 Claims, 5 Drawing Sheets

(56) References Cited

U.S. PATENT DOCUMENTS

| | | | |
|---|---|---|---|
| 6,519,065 | B1 | 2/2003 | Colbourne et al. |
| 6,521,453 | B1 | 2/2003 | Crameri et al. |
| 6,528,311 | B1 | 3/2003 | delCardayre et al. |
| 6,573,098 | B1 | 6/2003 | Stemmer |
| 6,576,467 | B1 | 6/2003 | Stemmer |
| 6,579,678 | B1 | 6/2003 | Patten et al. |
| 6,586,182 | B1 | 7/2003 | Patten et al. |
| 6,602,986 | B1 | 8/2003 | Stemmer et al. |
| 6,613,514 | B2 | 9/2003 | Patten et al. |
| 6,653,072 | B1 | 11/2003 | Patten et al. |
| 6,716,631 | B1 | 4/2004 | delCardayre et al. |
| 6,946,296 | B2 | 9/2005 | Patten et al. |
| 6,961,664 | B2 | 11/2005 | Selifonov et al. |
| 6,995,017 | B1 | 2/2006 | Stemmer |
| 7,024,312 | B1 | 4/2006 | Selifonov et al. |
| 7,058,515 | B1 | 6/2006 | Selifonov et al. |
| 7,105,297 | B2 | 9/2006 | Minshull et al. |
| 7,148,054 | B2 | 12/2006 | delCardayre et al. |
| 7,288,375 | B2 | 10/2007 | Stemmer et al. |
| 7,421,347 | B2 | 9/2008 | Selifonov et al. |
| 7,430,477 | B2 | 9/2008 | Selifonov et al. |
| 7,534,564 | B2 | 5/2009 | Patten et al. |
| 7,620,500 | B2 | 11/2009 | Mundorff et al. |
| 7,620,502 | B2 | 11/2009 | Selifonov et al. |
| 7,629,170 | B2 | 12/2009 | delCardayre et al. |
| 7,702,464 | B1 | 4/2010 | Emig et al. |
| 7,747,391 | B2 | 6/2010 | Gustafsson et al. |
| 7,747,393 | B2 | 6/2010 | Fox |
| 7,751,986 | B2 | 7/2010 | Gustafsson et al. |
| 7,776,598 | B2 | 8/2010 | Patten et al. |
| 7,783,428 | B2 | 8/2010 | Gustafsson et al. |
| 7,795,030 | B2 | 9/2010 | Minshull et al. |
| 7,853,410 | B2 | 12/2010 | Selifonov et al. |
| 7,868,138 | B2 | 1/2011 | Stemmer et al. |
| 7,873,499 | B2 | 1/2011 | Selifonov et al. |
| 7,904,249 | B2 | 3/2011 | Selifonov et al. |
| 7,957,912 | B2 | 6/2011 | Selifonov et al. |
| 7,960,152 | B2 * | 6/2011 | Taylor et al. ............ 435/138 |
| 2008/0220990 | A1 | 9/2008 | Fox |
| 2009/0312196 | A1 | 12/2009 | Colbeck et al. |

FOREIGN PATENT DOCUMENTS

| | | |
|---|---|---|
| WO | 95/22625 A1 | 8/1995 |
| WO | 96/00787 A1 | 1/1996 |
| WO | 97/00078 A1 | 1/1997 |
| WO | 97/35966 A1 | 10/1997 |
| WO | 98/27230 A1 | 6/1998 |
| WO | 98/31837 A1 | 7/1998 |
| WO | 00/04190 A1 | 1/2000 |
| WO | 01/75767 A2 | 10/2001 |
| WO | 2007/136762 A2 | 11/2007 |
| WO | 2009/152336 A1 | 12/2009 |
| WO | 2010/144103 A1 | 12/2010 |
| WO | 2011/006136 A2 | 1/2011 |

OTHER PUBLICATIONS

Blaiseau, P-L., et al., "Primary structure of a chitinase-encoding gene (chi1) from the filamentous fungus Aphanocladium album: similarity to bacterial chitinases," Gene, 120:243-248 [1992].
Boel, E., et al., "Two different types of intervening sequences in the glucoamylase gene from *Aspergillus niger*," EMBO J., 3:1581-85 [1984].
Botstein, D., et al., "Strategies and Applications of in Vitro Mutagenesis," Science, 229(4719):1193-1201 [1985].
Brat, D., et al., "Functional Expression of a Bacterial Xylose Isomerase in *Saccharomyces cerevisiae*," Appl. Environ. Microbiol. 75(8):2304-2311 [Feb. 13, 2009].
Carter, P., "Site-directed mutagenesis," Biochem. J., 237:1-7 [1986].
Case, M.E, et al., "Efficient transformation of *Neurospora crassa* by utilizing hybrid plasmid DNA," Proc. Natl. Acad. Sci. USA, 76(10):5259-5263 [1979].
Christians, F.C., et al., "Directed evolution of thymidine kinase for AZT phosphorylation using DNA family shuffling," Nat. Biotechnol., 17:259-264 [1999].
Crameri A., et al., "DNA shuffling of a family of genes from diverse species accelerates directed evolution," Nature, 391:288-291 [1998].
Crameri, A., et al., "Improved green fluorescent protein by molecular evolution using DNA shuffling," Nat. Biotechnol., 14:315-319 [1996].
Crameri, A., et al., "Molecular evolution of an arsenate detoxification pathway by DNA shuffling," Nat. Biotechnol., 15:436-438 [1997].
Dale, S.J. et al. "Oligonucleotide-Directed Random Mutagenesis Using the Phosphorothioate Method," Meth. Mol. Biol., 57:369-74 [1996].
Dayhoff, M.O. et al., in Atlas of Protein Sequence and Structure, "A model of evolutionary change in proteins," vol. 5, Suppl. 3, Natl. Biomed. Res. Round, Washington D.C. [1978], pp. 345-352.
Dupont, A.-L., et al., "Comprehensive characterisation of cellulose- and lignocellulosedegradation products in aged papers: Capillary zone electrophoresis of low-molar mass organic acids, carbohydrates, and aromatic lignin derivatives," Carbohydr. Polym., 68:1-16 [2007].
Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.
Henikoff, S., et al., "Amino acid substitution matrices from protein blocks," Proc. Natl. Acad. Sci. USA, 89:10915-10919 [1992].
Henriksen, A.L.S., et al., "Study of the glucoamylase promoter in *Aspergillllus niger* using green fluorescent protein," Microbiol., 145:729-34 [1999].
Hjersted, J.L., et al., "Genome-Scale Analysis of *Saccharomyces cerevisiae* Metabolism and Ethanol Productionin Fed-Batch Culture," Biotechnol. Bioengineer., 97(5):1190-1204 [2007].
Johnstone, I.L., et al., "Cloning an *Aspergillus nidulans* developmental gene by transformation," EMBO J.,4 (5):1307-1311 [1985].
Kelly, J.M., et al., "Transformation of *Asoergillus niger* by the amdS gene of *Aspergillus nidulans*," EMBO J., 4 (2):475-479 [1985].
Kinsey, J.A., et al., "Transformation of *Neurospora crassa* with the Cloned am (Glutamate Dehydrogenase) Gene," Mol. Cell. Biol., 4:117-122 [1984].
Kramer, B., et al., "Different base/base mismatches are corrected with different efficiencies by the methyl-directed DNA mismatch-repair system of *E. coli*," Cell, 38:879-887 [1984].
Kuyper, M., et al., "Metabolic engineering of a xylose-isomerase-expressing *Saccharomyces cerevisiae* strain for rapid anaerobic xylose fermentation," FEMS Yeast Res., A445:399-409 [2005].
Limon, C., et al., "Primary structure and expression pattern of the 33-kDa chitinase gene from the nucoparasitic fungus *Trichocherma harzianum*," Curr. Genet., 28:478-83 [1995].
Ling, M.M., et al., "Approaches to Dna Mutagenesis: An Overview," Anal. Biochem., 254(2):157-78 [1997].
Manivasakam, P., et al., "Nonhomologous End Joining during Restriction Enzyme-Mediated DNA Integration in *Saccharomyces cerevisiae*," Mol. Cell Biol., 18(3):1736-1745 [1998].A46.
Matsushika, A., et al., "Expression of protein engineered NADP+-dependent xylitol dehydrogenase increases ethanol production from xylose in recombinant *Saccharomyces cerevisiae*," Appl. Environ Microbiol., 81(2):243-55 [2008].
Matsushika, A., et al., "Ethanol production from xylose in engineered *Saccharomyces cerevisiae* strains: current state and perspectives," Appl. Microbiol. Biotechnol., 84:37-53 [2009].
Minshull, J., et al., "Protein evolution by molecular breeding," Curr. Op. Chem. Biol., 3:284-290 [1999].
Nakamura, Y., et al., "Codon usage tabulated from international DNA sequence databases: status for the year 2000," Nucl. Acids Res., 28:292 [2000].
Nunberg, J.H., et al., "Molecular Cloning and Characterization of the Glucoamylase Gene of *Aspergillus awamori*," Mol. Cell Biol., 4(11):2306-2315 [1984].
Oldenburg, K.R., et al., "Recombination-mediated PCR-directed plasmid construction in vivo in yeast," Nucl. Acids Res., 25(2):451-452 [1997].

(56) References Cited

OTHER PUBLICATIONS

McInerney, J.O., "GCUA: general codon usage analysis," Bioinformatics, 14(4):372-73 (1998).
Park J.B., et al., "The human glutaredoxin gene: determination of its organization, transcription start point, and promoter analysis," Gene, 197:189-93 [1997].
Romanos, M.A., et al., "Foreign Gene Expression in Yeast: a Review," Yeast 8:423-488 [1992].
Runquist, D., et al., "Comparison of heterologous xylose transporters in recombinant *Saccharomyces cerevisiae*," Biotechnol. Biofuels, 3(5):1-7 [2010].
Sauer, U., "Evolutionary Engineering of Industrially Important Microbial Phenotypes," Adv. Biochem. Engineer. Biotechnol., 73:129-169 [2001].
Sedlak, M., et al., "Characterization of the effectiveness of hexose transporters for transporting xylose during glucose and xylose co-fermentation by a recombinant *Saccharomyces* yeast," Yeast 21:671-684 [2004].
Sheir-Neiss, G., et al., "Characterization of the secreted cellulases of Trichoderma reesei wild type and mutants during controlled fermentations," Appl. Microbiol. Biotechnol., 20:46-53 [1984].
Smith, M., "In Vitro Mutagenesis," Ann. Rev. Genet., 19:423-462 [1985].
Sonderegger, M., et al., "Molecular Basis for Anaerobic Growth of *Saccharomyces cerevisiae* on Xylose, Investigated by Global Gene Expression and Metabolic Flux Analysis," Appl. Environ. Microbiol., 70(4):2307-2317 [2004].
Stemmer, W.P.C., "DNA shuffling by random fragmentation and reassembly: In vitro recombination for molecular evolution," Proc. Nat. Acad. Sci. USA, 91:10747-10751 [1994].
Stemmer, W.P.C., "Rapid evolution of a protein in vitro by DNA shuffling," Nature, 370:389-391 [1994].
Stenico, M., et al., "Codon usage in *Caenorhabditis elegans*: delineation of translational selection and mutational biases," Nucl. Acids Res. 22(13):2437-46 [1994].

Teixiera, M.C., et al., "Genome-Wide Identification of *Saccharomyces cerevisiae* Genes Required for Maximal Tolerance to Ethanol," Appl. Environ. Microbiol., 75(18):5761-5772 [2009].
Tilburn, J., et al., "Transformation by integration in *Aspergillus nidulans*," Gene 26:205-221 [1983].
Tiwari, S., et al., "Prediction of probable genes by Fourier analysis of genomic sequences," Comput. Appl. Biosci. 13 (3):263-270 [1997].
Uberbacher, E.C., et al., "Discovering and Understanding Genes in Human DNA Sequence Using GRAIL," Methods Enzymol., 266:259-281 [1996].
Wada, K., et al., "Codon usage tabulated from the GenBank genetic sequence data," Nucl. Acids Res., 20:2111-2118 [1992].
Wells, J.A., et al., "Cassette mutagenesis: an efficient method for generation of multiple mutations at defined sites," Gene, 34:315-323 [1985].
Wenger, J.W., et al., "Bulk Segregant Analysis by High-Throughput Sequencing Reveals a Novel Xylose Utilization Gene from *Saccharomyces cerevisiae*," PLoS Genet., 6(5):1-17 [2010].
Wisselink, H.W., et al., "Novel Evolutionary Engineering Approach for Accelerated Utilization of Glucose, Xylose, and Arabinose Mixtures by Engineered *Saccharomyces cerevisiae* Strains," Appl. Environ. Microbiol., 75(4):907-914 [2009].
Wright, A., et al., "Diverse Plasmid DNA Vectors by Directed Molecular Evolution of Cytomegalovirus Promoters," Hum. Gene Ther., 16:881-892 [2005].
Wright, F., "The 'effective number of codons' used in a gene," Gene 87:23-29 [1990].
Yelton, M.M., et al., "Transformation of *Aspergillus nidulans* by using a trpC plasmid," Proc. Natl. Acad. Sci. USA, 81:1480-1474 [1984].
Zhang, J.-H., et al., "Directed evolution of a fucosidase from a galactosidase by DNA shuffling and screening" Proc. Nat. Acad. Sci. U.S.A., 94:4504-4509 [1997].
Zhu, T., et al., "Construction of two Gateway vectors for gene expression in fungi," Plasmid 62:128-33 [2009].

* cited by examiner

PENTOSE FERMENTATION BY A RECOMBINANT MICROORGANISM

The present application claims priority to U.S. Pat. Appln. Ser. No. 61/469,505, filed on Mar. 30, 2011, and U.S. Pat. Appln. Ser. No. 61/496,152, filed on Jun. 13, 2011, both of which are incorporated by reference in their entirety herein.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX35-079US1_ST25.TXT, created on Apr. 12, 2012, 77,994 bytes, machine format IBM-PC, MS-Windows operating system, is hereby incorporated by reference.

FIELD OF THE INVENTION

The present invention provides methods and compositions suitable for use in the conversion of xylose to xylitol and xylulose, including nucleic acid constructs, recombinant fungal host cells, and related materials.

BACKGROUND

Ethanol and ethanol fuel blends are widely used in Brazil and in the United States as a transportation fuel. Combustion of these fuels is believed to produce fewer of the harmful exhaust emissions (e.g., hydrocarbons, nitrogen oxide, and volatile organic compounds [VOCs]) that are generated by the combustion of petroleum. Bioethanol is a particularly favored form of ethanol because the plant biomass from which it is produced utilizes sunlight, an energy source that is renewable. In the United States, ethanol is used in gasoline blends that are from 5% to 85% ethanol. Blends of up to 10% ethanol (E10) are approved for use in all gasoline vehicles in the U.S. and blends of up to 85% ethanol (E85) can be utilized in specially engineered flexible-fuel vehicles (FFV). The Brazilian government has mandated the use of ethanol-gasoline blends as a vehicle fuel, and the mandatory blend has been 25% ethanol (E25) since 2007.

Bioethanol is currently produced by the fermentation of hexose sugars that are obtained from carbon feedstocks. Currently, only the sugar from sugar cane and starch from feedstock such as corn can be economically converted. There is, however, much interest in using lignocellulosic feedstocks where the cellulose part of a plant is broken down to sugars and subsequently converted to ethanol. Lignocellulosic biomass is made up of cellulose, hemicelluloses, and lignin. Cellulose and hemicellulose can be hydrolyzed in a saccharification process to sugars that can be subsequently converted to ethanol via fermentation. The major fermentable sugars from lignocelluloses are glucose and xylose. For economical ethanol yields, a strain that can effectively convert all the major sugars present in cellulosic feedstock would be highly desirable.

SUMMARY OF THE INVENTION

The present invention provides methods and compositions suitable for use in the conversion of xylose to xylitol and xylulose, including nucleic acid constructs, recombinant fungal host cells, and related materials.

In some embodiments, the present invention provides recombinant nucleic acid constructs comprising at least one polynucleotide sequence that encodes at least one xylose reductase, wherein the polynucleotide is selected from: (a) a polynucleotide that encodes a polypeptide comprising an amino acid sequence having at least about 70% identity to SEQ ID NO:2, wherein the amino acid sequence comprises at least one substitution set forth herein; and (b) a polynucleotide that hybridizes under stringent hybridization conditions to the complement of a polynucleotide that encodes a polypeptide having the amino acid sequence of SEQ ID NO:2, and wherein the amino acid sequence comprises at least one substitution set forth herein. In some embodiments, the polynucleotide sequence encodes a polypeptide comprising an amino acid sequence at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:2, wherein the amino acid sequence comprises at least one substitution set forth herein. In some alternative embodiments, the polynucleotide sequence encodes a polypeptide comprising a portion of the amino acid sequence set forth in SEQ ID NO:2, wherein the amino acid sequence comprises at least one substitution set forth herein. In some further embodiments, the polynucleotide sequence encodes a polypeptide having an amino acid sequence that comprises at least one substitution at position 2, 3, 7, 11, 14, 17, 23, 24, 33, 36, 46, 47, 49, 56, 62, 68, 89, 97, 102, 108, 114, 116, 123, 132, 134, 143, 152, 155, 157, 162, 168, 184, 206, 219, 224, 225, 226, 228, 246, 231, 232, 233, 236, 240, 242, 245, 246, 249, 252, 255, 261, 266, 267, 275, 276, 279, 281, 282, 283, 285, 297, 301, 302, 303, and/or 318, wherein the positions are numbered by correspondence with the amino acid sequence of *P. stipitis* xylose reductase set forth in SEQ ID NO:2. In some additional embodiments, the polynucleotide sequence encodes a polypeptide having an amino acid sequence that comprises at least one substitution selected from P2, S3, N7, D11, A14, F17, D23, V24, R33, K36, E46, D47, A49, A56, I62, K68, E89, S97, D102, L108, T114, K116, K123, K132, D134, I143, K152, K155, G157, I162, P168, S184, R206, Q219, L224, N225, Q226, R228, A246, N231, T232, S233, F236, T240, K242, A245, A246, G249, P252, V255, 5261, A266, I267, P275, R276, E279, K281, D282, V283, S285, A297, I301, N302, L303, and/or V318, wherein the positions are numbered by correspondence with the amino acid sequence of *P. stipitis* xylose reductase set forth in SEQ ID NO:2. In yet some additional embodiments, the polynucleotide sequence encodes a polypeptide having an amino acid sequence that comprises at least one substitution selected from P2T, S3H, S3R, S3W, N7L, D11K, A14V, F17W, D23E, V24G, R33L, R22V, K36Q, E46K, D47G, D47N, A49G, A56E, A56Y, I62V, K68G, K68M, K68R, E89N, E89V, S97R, S97T, D102T, L108Y, T114S, K116Q, K123C, K132A, K132N, D134E, D134H, D134V, I143L, K152A, K152E, K152H, K152Q, K155A, K155D, K155I, K155R, K155Y, G157R, I162L, P168S, S184A, R206S, R206V, Q219H, Q219L, Q219T, L224A, L224S, L224V, N225D, N225E, N225K, N225S, N225Y, Q226D, Q226E, Q226S, Q226V, R228T, N231G, N231H, N231L, N231S, T232A, T232C, T232S, T232V, S233C, S233F, S233G, S233I, S233K, S233V, F236L, T240V, K242L, A245S, A246L, A246S, G249D, P252C, V255I, S261A, S261C, S261N, S261T, A266V, A266C, I267V, P275A, R276M, R276W, E279Q, K281L, K281V, D282C, D282G, D282R, V283H, S285E, S285T, A297H, A297S, I301C, I301Y, N302D, N302G, N302S, L303I, L303V, and/or V318C, wherein the positions are numbered by correspondence with the amino acid sequence of *P. stipitis* xylose reductase set forth in SEQ ID NO:2. In some embodiments, the polynucleotide sequence is at least about 80%, about 85%, about 90%, or at least 95% identical to SEQ ID NO:1, and wherein the polynucleotide sequence comprises at least one mutation set forth herein. In some additional embodiments, the polynucleotide sequence comprises at least one mutation selected from t82a, t99a, g156a, c201t, a280c, c306t, t354g, t358c, a378t, c408t, a426t, c438t, a478c, t511c, a585g, t670c, t688c, t703c, t747c, t751a, t766c, t811a, c816t, a826c, c849g, c855t, and/or c906t, wherein the nucleotide position is determined by alignment with SEQ ID NO:1. In some additional embodiments, the present invention provides nucleic acid constructs comprising SEQ ID NO:3 and/or SEQ ID NO:4.

The present invention also provides isolated xylose reductase variants, wherein the variants have xylose reductase activity and comprise a substitution at one or more positions selected from 2, 3, 7, 11, 14, 17, 23, 24, 33, 36, 46, 47, 49, 56, 62, 68, 89, 97, 102, 108, 114, 116, 123, 132, 134, 143, 152, 155, 157, 162, 168, 184, 206, 219, 224, 225, 226, 228, 246, 231, 232, 233, 236, 240, 242, 245, 246, 249, 252, 255, 261, 266, 267, 275, 276, 279, 281, 282, 283, 285, 297, 301, 302, 303, and/or 318, wherein the positions are numbered by correspondence with the amino acid sequence of *P. stipitis* xylose reductase set forth in SEQ ID NO:2. In some embodiments, the variant has xylose reductase activity and comprises a substitution at one or more positions selected from P2, S3, N7, D11, A14, F17, D23, V24, R33, K36, E46, D47, A49, A56, I62, K68, E89, S97, D102, L108, T114, K116, K123, K132, D134, I143, K152, K155, G157, I162, P168, S184, R206, Q219, L224, N225, Q226, R228, A246, N231, T232, S233, F236, T240, K242, A245, A246, G249, P252, V255, 5261, A266, I267, P275, R276, E279, K281, D282, V283, S285, A297, I301, N302, L303, and/or V318, wherein the positions are numbered by correspondence with the amino acid sequence of *P. stipitis* xylose reductase set forth in SEQ ID NO:2. In some additional embodiments, the variant has xylose reductase activity and comprises a substitution at one or more positions selected from P2T, S3H, S3R, S3W, N7L, D11K, A14V, F17W, D23E, V24G, R33L, R22V, K36Q, E46K, D47G, D47N, A49G, A56E, A56Y, I62V, K68G, K68M, K68R, E89N, E89V, S97R, S97T, D102T, L108Y, T114S, K116Q, K123C, K132A, K132N, D134E, D134H, D134V, I143L, K152A, K152E, K152H, K152Q, K155A, K155D, K155I, K155R, K155Y, G157R, I162L, P168S, S184A, R206S, R206V, Q219H, Q219L, Q219T, L224A, L224S, L224V, N225D, N225E, N225K, N225S, N225Y, Q226D, Q226E, Q226S, Q226V, R228T, N231G, N231H, N231L, N231S, T232A, T232C, T232S, T232V, S233C, S233F, S233G, S233I, S233K, S233V, F236L, T240V, K242L, A245S, A246L, A246S, G249D, P252C, V255I, S261A, S261C, S261N, S261T, A266V, A266C, I267V, P275A, R276M, R276W, E279Q, K281L, K281V, D282C, D282G, D282R, V283H, S285E, S285T, A297H, A297S, I301C, I301Y, N302D, N302G, N302S, L303I, L303V, and/or V318C, wherein the positions are numbered by correspondence with the amino acid sequence of *P. stipitis* xylose reductase set forth in SEQ ID NO:2. In some further embodiments, the isolated xylose reductase variants comprise the sequence set forth in SEQ ID NO:41, 43, 45, and/or 47. The present invention also provides isolated nucleic acid sequences comprising SEQ ID NO:3, 4, 40, 42, 44, and/or 46.

The present invention also provides recombinant nucleic acid constructs comprising at least one polynucleotide sequence that encodes a xylitol dehydrogenase, wherein the polynucleotide is selected from: (a) a polynucleotide that encodes a polypeptide comprising an amino acid sequence having at least 70% identity to SEQ ID NO:6, wherein the amino acid sequence comprises at least one substitution set forth herein; and (b) a polynucleotide that hybridizes under stringent hybridization conditions to the complement of a polynucleotide that encodes a polypeptide having the amino acid sequence of SEQ ID NO:6, wherein the amino acid sequence comprises at least one substitution set forth herein. The present invention further provides nucleic acid constructs, wherein the polynucleotide sequence encodes a polypeptide comprising an amino acid sequence at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:6, wherein the amino acid sequence comprises at least one substitution set forth herein. In some embodiments, the polynucleotide sequence encodes a polypeptide comprising at least a portion of the amino acid sequence set forth in SEQ ID NO:6, wherein the amino acid sequence comprises at least one substitution set forth herein. In some further embodiments, the polynucleotide sequence encodes a polypeptide having an amino acid sequence that comprises at least one substitution at position 5, 13, 19, 49, 81, 149, 187, 189, 202, 205, 206, 210, 215, 218, 226, 227, 228, 229, 230, 231, 235, 239, 241, 251, 252, 256, 260, 286, 287, 296, 307, 327, 350, and/or 352, wherein the positions are numbered by correspondence with the amino acid sequence of *P. stipitis* xylitol dehydrogenase set forth in SEQ ID NO:6. In some additional embodiments, the polynucleotide sequence encodes a polypeptide having an amino acid sequence that comprises at least one substitution selected from P5, D13, T19, A49, S81, H149, V187, L189, G202, V205, V206, I208, F209, D210, N211, M215, D218, F226, N227, S228, K229, T230, G231, E235, A239, G241, C251, T252, P256, L260, T286, V287, F296, K307, D327, A350, and/or K352, wherein the positions are numbered by correspondence with the amino acid sequence of *P. stipitis* xylitol dehydrogenase set forth in SEQ ID NO:6. In some further embodiments, the polynucleotide sequence encodes a polypeptide having an amino acid sequence that comprises at least one substitution selected from P5E, P5R, D13G, T19L, T19Q, A49Q, S81G, H149R, V187M, L189C, G202D, V205C, V205H, V206A, I208R, F209S, D210W, N211K, N211R, N211S, M215A, M215C, D218R, F226V, N227T, S228P, K229R, T230V, G231A, G231H, E235K, E235Q, A239C, G241W, C251G, C251T, T252S, P256A, P256Q, L260Q, T286V, V287L, F296R, K307R, D327A, A350D, and/or K352E, wherein the positions are numbered by correspondence with the amino acid sequence of *P. stipitis* xylitol dehydrogenase set forth in SEQ ID NO:6. In some still further embodiments, the polynucleotide sequence is at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99% identical to SEQ ID NO:5, and wherein the polynucleotide sequence comprises at least one mutation set forth herein. In some embodiments, the polynucleotide sequence comprises mutations at at least one position selected from t24g, c630t, a732g, a768t, a780g, wherein nucleotide position is determined by alignment with SEQ ID NO:5. In some additional embodiments, the nucleic acid construct comprises SEQ ID NO:7 and/or SEQ ID NO:8. In some further embodiments, the present invention provides an isolated nucleic acid sequence comprising SEQ ID NO:7, 8, and/or 48.

The present invention also provides isolated xylitol dehydrogenase variants comprising the sequence set forth in SEQ ID NO:49. In some additional embodiments, the present invention provides isolated xylitol dehydrogenase variants, wherein the variants have xylitol dehydrogenase activity and comprise a substitution at one or more positions selected from 5, 13, 19, 49, 81, 149, 187, 189, 202, 205, 206, 210, 215, 218, 226, 227, 228, 229, 230, 231, 235, 239, 241, 251, 252, 256, 260, 286, 287, 296, 307, 327, 350, and/or 352, wherein the positions are numbered by correspondence with the amino acid sequence of *P. stipitis* xylitol dehydrogenase set forth in SEQ ID NO:6. In some embodiments, the xylitol dehydrogenase variant have xylitol dehydrogenase activity and comprise a substitution at one or more positions selected from P5, D13, T19, A49, S81, H149, V187, L189, G202, V205, V206, I208, F209, D210, N211, M215, D218, F226, N227, S228, K229, T230, G231, E235, A239, G241, C251, T252, P256, L260, T286, V287, F296, K307, D327, A350, and/or K352, wherein the positions are numbered by correspondence with the amino acid sequence of *P. stipitis* xylitol dehydrogenase set forth in SEQ ID NO:6. In some further embodiments, the isolated xylitol dehydrogenase variant has xylitol dehydrogenase activity and comprises a substitution at one or more positions selected from P5E, P5R, D13G, T19L, T19Q, A49Q, S81G, H149R, V187M, L189C, G202D, V205C, V205H, V206A, I208R, F209S, D210W, N211K, N211R, N211S, M215A, M215C, D218F, F226V, N227T, S228P, K229R, T230V, G231A, G231H, E235K, E235Q, A239C, G241W, C251G, C251T, T252S, P256A, P256Q, L260Q, T286V, V287L, F296R, K307R, D327A, A350D, and/or K352E, wherein the positions are numbered by correspondence with the amino acid sequence of *P. stipitis* xylitol dehydrogenase set forth in SEQ ID NO:6. The present invention also provides recombinant nucleic acid constructs comprising SEQ ID NO:11 and/or SEQ ID NO:12.

The present invention also provides recombinant nucleic acid constructs comprising polynucleotide sequences encoding at least one xylose reductase and at least one xylitol dehydrogenase, wherein the polynucleotide sequences are selected from SEQ ID NOS:1, 3, 4, 40, 42, 44, and 46; and SEQ ID NOS:5, 7, 8, 48.

The present invention further provides recombinant nucleic acid constructs further comprising at least one polynucleotide sequence encoding at least one xylulokinase, wherein the polynucleotide sequence comprises SEQ ID NO:11 and/or SEQ ID NO:12. In some embodiments, the recombinant nucleic acid constructs comprise at least one sequence selected from SEQ ID NOS:1, 3, 4, 5, 7, 8, 11, 12, 40, 42, 44, 46, and 48. In some further embodiments, the constructs comprise SEQ ID NO:46 and/or 48. In some additional embodiments, the nucleic acid constructs further comprise at least one genetic element that facilitates stable integration into a fungal host genome. In some additional embodiments, the nucleic acid constructs further comprise a genetic element that facilitates stable integration into a fungal host genome. In some embodiments, the genetic element facilitates integration into a fungal host genome by homologous recombination. In yet some additional embodiments, the nucleic acid constructs comprise a fungal origin of replication. In some embodiments, the fungal origin of replication is a yeast origin of replication. In some further embodiments, the polynucleotide sequence is operatively linked to a promoter sequence that is functional in a fungal cell. In some embodiments, the promoter sequence is a fungal promoter sequence. In some additional embodiments, the fungal promoter sequence is a yeast promoter sequence. In still some further embodiments, the polynucleotide sequence is operatively linked to a transcription termination sequence that is functional in a fungal cell. In some embodiments, the polynucleotide sequence contains codons optimized for expression in a yeast cell. In some further embodiments, the polynucleotide sequence comprises SEQ ID NO:3, 4, 7, 8, 11, and/or 12.

The present invention also provides recombinant fungal host cells comprising at least one polynucleotide sequence encoding at least one xylose reductase, wherein the polynucleotide sequences comprise at least one mutation relative to SEQ ID NO:1, as set forth herein. In some embodiments, the recombinant fungal host cell comprises at least one polynucleotide sequence selected from SEQ ID NOS:3, 4, 40, 42, 44, and 46. In some embodiments, the recombinant fungal host cells comprise at least one polynucleotide sequence encoding at least one xylitol dehydrogenase, wherein the polynucleotide sequence comprises at least one mutation relative to SEQ ID NO: 5, as set forth herein. In some embodiments, at least one polynucleotide sequence is selected from SEQ ID NOS:7, 8, and 48.

The present invention also provides recombinant fungal host cells comprising at least one polynucleotide sequence encoding at least one xylulokinase, wherein the polynucleotide sequences comprise at least one mutation relative to SEQ ID NO:9. In some embodiments, at least one polynucleotide sequence is selected from SEQ ID NOS:11 and 12.

The present invention also provides recombinant fungal host cells comprising at least one polynucleotide sequence encoding at least one xylose reductase, wherein the polynucleotide sequence comprises SEQ ID NO:1, 3, 4, 40, 42, 44, and/or 46; and at least one polynucleotide encoding at least one xylitol dehydrogenase, wherein the polynucleotide sequence comprises SEQ ID NO:5, 7, 8, and/or 48. In some embodiments, the recombinant fungal host cells further comprise at least one polynucleotide encoding at least one xylulokinase, wherein the polynucleotide comprises SEQ ID NO:11 and/or 12. In some embodiments, at least one polynucleotide is integrated into the host cell genome. In some additional embodiments, the host cell is a yeast cell. In some embodiments, the host cell has had one or more native genes deleted from its genome. In some further embodiments, the deletion results in one or more phenotypes selected from increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced production of by products, wherein comparison is made with respect to the corresponding host cell without the deletion(s). In some additional embodiments, the host cell is altered to overexpress one or more polynucleotides. In some further embodiments, overexpression results in one or more phenotypes selected from increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and reduced product of by products, wherein comparison is made to the corresponding unaltered host cell. In still some further embodiments, the host cell comprises at least one xylose reductase variant and at least one xylitol dehydrogenase variant. In some additional embodiments, the recombinant fungal host cells further comprise at least one xylulokinase. In some embodiments, the xylulokinase is encoded by SEQ ID NO:11 and/or 12. In some additional embodiments, the recombinant fungal host cell is transformed using nucleic acid constructs comprising from about two to about fifty copies of at least one xylose reductase and/or xylitol dehydrogenase and/or xylulokinase. It is not intended that the present invention be limited to any particular copy number of xylose reductase and/or xylitol dehydrogenase genes and/or xylulokinase, as any suitable number finds use in the present invention. In some embodiments, the nucleic acid constructs comprise any combination of wild-type and/or variant xylose reductase and/or xylitol dehydrogenase and/or xylulokinase. Furthermore, any suitable method for introducing multiple copies of either xylose reductase and/or xylitol dehydrogenase and/or xylulokinase find use in the present invention.

The present invention also provides processes for producing a fermentation product, comprising: (a) providing at least one recombinant fungal host cell provided herein; (b) providing a fermentation medium comprising; and (c) contacting the fermentation medium with the recombinant fungal host cell under conditions suitable for generating the fermentation product. In some embodiments, the process further comprises (d) recovering the fermentation product. In some additional embodiments, the fermenting step is carried out under conditions selected from microaerobic or aerobic conditions. In some embodiments, the fermenting step is carried out under anaerobic conditions. In some further embodiments, the fermentation product is selected from an alcohol, a fatty acid, lactic acid, acetic acid, 3-hydroxypropionic acid, acrylic acid, succinic acid, citric acid, malic acid, fumaric acid, succinic acid, an amino acid, 1,3-propanediol, ethylene, glycerol, and a β-lactam. In some additional embodiments, the fermentation product is an alcohol selected from ethanol and butanol. In some embodiments, the fermentation product is ethanol. In some embodiments, the fermentation medium comprises product from a saccharification process. In some further embodiments, the fermentation medium comprises hemicellulosic feedstock.

DESCRIPTION OF THE FIGURES

FIG. 2A depicts the pentose phosphate pathway (PPP). The substrates and products are shown. The enzymes are represented by numbers as follows: 6. Ribulose-5-phosphate 3-epimerase; 7. Transketolase (TKL1); 8. Transaldolase (TAL1); 9. Ribose-5-phosphate ketoisomerase (RKI1); 10. 6-phosphogluconate dehydrogenase (GND1); 11. 6-phosphogluconalactonase (SOL3); and 12. Glucose-6-phosphate-1-dehydrogenase (ZWF).

FIG. 2B depicts the pathway of glycolysis. The substrates and products are shown. The enzymes are represented by numbers as follows: 13. Hexokinase; 14. Phosphoglucose isomerase; 15. Phosphofructokinase; 16. Aldolase; 17. Triose phosphate isomerase; 18. Glyceraldehyde 3-phosphate dehydrogenase; 19. 3-Phosphoglycerate kinase; 20. Phosphoglyceromutase; 21. Enolase; and 22. Pyruvate kinase.

FIG. 2C depicts the metabolic pathway for converting pyruvate to ethanol. The substrates and products are shown.

The enzymes are represented by numbers as follows: 23. Pyruvate decarboxylase; 24. Aldehyde dehydrogenase; and 25. Alcohol dehydrogenase.

Figure 3:
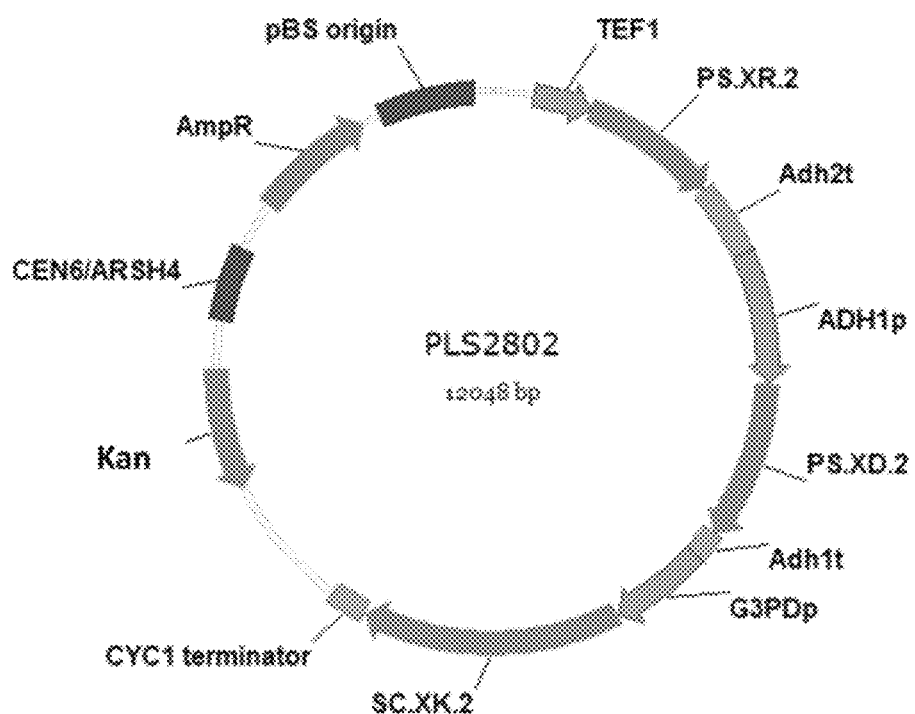

FIG. 3 provides a map of plasmid PLS2802, comprising XR.2, XD.2, and XK.2 genes.

DESCRIPTION OF THE INVENTION

The present invention provides methods and compositions suitable for use in the conversion of xylose to xylitol and xylulose, including nucleic acid constructs, recombinant fungal host cells, and related materials.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the terms "isolated" and "purified" are used to refer to a molecule (e.g., an isolated nucleic acid, polypeptide, etc.) or other component that is removed from at least one other component with which it is naturally associated.

As used herein, the term "reference enzyme" refers to an enzyme to which a variant enzyme of the present invention is compared in order to determine the presence of an improved property in the variant enzyme being evaluated, including but not limited to improved thermoactivity, improved thermostability, or improved stability. In some embodiments, a reference enzyme is a wild-type enzyme (e.g., wild-type xylose reductase or xylitol dehydrogenase). In some embodiments, a reference enzyme is another variant enzyme (e.g., another variant xylose reductase or xylitol dehydrogenase enzyme of the present invention).

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. A recombinant cell contains a recombinant polynucleotide or polypeptide.

As used herein, the terms "enzyme variant" and "variant enzyme" are used in reference to enzymes that are similar to a reference enzyme, particularly in their function, but have mutations in their amino acid sequence that make them different in sequence from the wild-type or another reference enzyme. Enzyme variants (e.g., "xylose reductase variants" and/or "xylitol dehydrogenase variants") can be made by a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific) or random mutagenesis over the entire gene (e.g., saturation mutagensis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. After the variants are produced, they can be screened for the desired property (e.g., high or increased; or low or reduced activity, increased thermal and/or alkaline stability, etc.).

As used herein, "combinatorial variant" refers to any variant that has a combination of two or more mutations (e.g., substitutions). In some embodiments, the combination of mutations results in changes in enzyme activity (e.g., improved thermostability, improved thermoactivity, improved specific activity, etc.).

As used herein, the term "overexpress" is intended to encompass increasing the expression of a protein to a level greater than the cell normally produces. It is intended that the term encompass overexpression of endogenous, as well as heterologous proteins.

For clarity, reference to a cell of a particular strain refers to a parental cell of the strain as well as progeny and genetically modified derivatives. Genetically modified derivatives of a parental cell include progeny cells that contain a modified genome or episomal plasmids that confer for example, antibiotic resistance, improved fermentation, the ability to utilize xylose as a carbon source, etc.

A nucleic acid construct, nucleic acid (e.g., a polynucleotide), polypeptide, or host cell is referred to herein as "recombinant" when it is non-naturally occurring, artificial or engineered.

The terms "xylose reductase" and "xylose reductase polypeptide" are used interchangeably herein to refer to an enzyme that is capable of catalyzing xylose to xylitol. The ability to catalyze xylose to xylitol is referred to herein as "xylose reductase activity".

The terms "protein" and "polypeptide" are used interchangeably herein to refer to a polymer of amino acid residues. The term "xylose reductase polynucleotide" refers to a polynucleotide that encodes a xylose reductase polypeptide.

In some embodiments, xylose reductase polynucleotides employed in the practice of the present invention encode a polypeptide comprising an amino acid sequence that is at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:2, wherein the sequence comprises at least one substitution set forth herein. In some embodiments, the xylose reductase polynucleotide encodes a polypeptide having an amino acid sequence comprising SEQ ID NO:41, 43, 45, and/or 47.

In some embodiments, xylose reductase polynucleotides employed in the practice of the present invention comprise polynucleotide sequences that are at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1, 3 and/or 4.

The terms "xylitol dehydrogenase" and "xylitol dehydrogenase polypeptide" are used interchangeably herein to refer to an enzyme that is capable of catalyzing xylitol to xylulose. The ability to catalyze xylitol to xylulose is referred to herein as "xylitol dehydrogenase activity". Also, as used herein, the term "xylitol dehydrogenase polynucleotide" refers to a polynucleotide that encodes a xylitol dehydrogenase polypeptide.

In some embodiments, xylitol dehydrogenase polynucleotides employed in the practice of the present invention encode polypeptides comprising amino acid sequences that are at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:6, wherein SEQ ID NO:6 further comprises at least one substitution as set forth herein. In some embodiments, the xylitol dehydrogenase polynucleotide encodes a polypeptide having an amino acid sequence comprising SEQ ID NO:6 and/or 49, wherein SEQ ID NO:6 further comprises at least one substitution as set forth herein In some embodiments, xylulokinase polynucleotides employed in the practice of the present invention comprise polynucleotides sequence that are at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:9, 11 and/or 12, wherein SEQ ID NO:9 further comprises at least one substitution.

The terms "percent identity," "% identity", "percent identical," and "% identical," are used interchangeably herein to refer to the percent amino acid or polynucleotide sequence identity that is obtained by ClustalW analysis (version W 1.8 available from European Bioinformatics Institute, Cambridge, UK), counting the number of identical matches in the alignment and dividing such number of identical matches by the length of the reference sequence, and using the following ClustalW parameters to achieve slow/accurate pairwise optimal alignments—DNA/Protein Gap Open Penalty: 15/10; DNA/Protein Gap Extension Penalty: 6.66/0.1; Protein weight matrix: Gonnet series; DNA weight matrix: Identity; Toggle Slow/Fast pairwise alignments=SLOW or FULL Alignment; DNA/Protein Number of K-tuple matches: 2/1; DNA/Protein number of best diagonals: 4/5; DNA/Protein Window size: 4/5.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art (See, e.g., Dayhoff et al., in Dayhoff [ed.], Atlas of Protein Sequence and Structure," Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g, Altschul et al., supra).

The present invention also provides a recombinant nucleic acid construct comprising a xylose reductase polynucleotide sequence that hybridizes under stringent hybridization conditions to the complement of a polynucleotide which encodes a polypeptide having the amino acid sequence of SEQ ID NO:2, wherein the polypeptide is capable of catalyzing the xylose to xylitol, and the polypeptide comprises at least one substitution set forth herein.

In some embodiments, the polynucleotide that hybridizes to the complement of a polynucleotide which encodes a polypeptide having the amino acid sequence of SEQ ID NO:2, wherein the polypeptide comprises at least one substitution as set forth herein, does so under high or very high stringency conditions to the complement of a reference sequence having the sequence of SEQ ID NO:1 (e.g., over substantially the entire length of the reference sequence). In some embodiments, the polynucleotide that hybridizes to the complement of a polynucleotide which encodes a polypeptide having the amino acid sequence of SEQ ID NO:2, wherein the polypeptide comprises at least one substitution as set forth herein, does so under high or very high stringency conditions to the complement of a reference sequence having the sequence of SEQ ID NO:3 (e.g., over substantially the entire length of the reference sequence). In some embodiments, the polynucleotide that hybridizes to the complement of a polynucleotide which encodes a polypeptide having the amino acid sequence of SEQ ID NO:2, wherein the amino acid sequence comprises at least one substitution as set forth herein, does so under high or very high stringency conditions to the complement of a reference sequence having the sequence of SEQ ID NO:4 (e.g., over substantially the entire length of the reference sequence).

The present invention also provides a recombinant nucleic acid construct comprising a xylitol dehydrogenase polynucleotide sequence that hybridizes under stringent hybridization conditions to the complement of a polynucleotide which encodes a polypeptide having the amino acid sequence of SEQ ID NO:6, wherein the polypeptide comprises at least one substitution set forth herein, and wherein the polypeptide is capable of catalyzing xylitol to xylulose.

Nucleic acids "hybridize" when they associate, typically in solution. There are numerous texts and other reference materials that provide details regarding hybridization methods for nucleic acids (See e.g., Tijssen, Laboratory Techniques in Biochemistry and Molecular Biology-Hybridization with Nucleic Acid Probes," Part1, Chapter 2, Elsevier, N.Y., [1993], which is incorporated herein by reference). For polynucleotides of at least 100 nucleotides in length, low to very high stringency conditions are defined as follows: prehybridization and hybridization at 42° C. in 5×SSPE, 0.3% SDS, 200 μg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The terms "corresponding to", "reference to" and "relative to" when used in the context of the numbering of a given amino acid or polynucleotide sequence refers to the numbering of the residues of a specified reference sequence when the given amino acid or polynucleotide sequence is compared to the reference sequence.

The "position" is denoted by a number that sequentially identifies each amino acid in the reference sequence based on its position relative to the N-terminus. Owing to deletions, insertions, truncations, fusions, and the like that must be taken into account when determining an optimal alignment, in general the amino acid residue number in a test sequence determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position the reference sequence. In the case of truncations or fusions there can be stretches of amino acids in either the reference or aligned sequence that do not correspond to any amino acid in the corresponding sequence.

As used herein, the terms "transformed" and "transformation" used in reference to a cell refer to a cell that has a non-native nucleic acid sequence integrated into its genome or has an episomal plasmid that is maintained through multiple generations.

As used herein, the term "by-product" refers to an organic molecule that is an undesired product of a particular fermentation process.

As used herein, the term "xylose pathway" refers to the steps of conversion of xylose to xylulose phosphate which is then metabolized through the pentose phosphate pathway. In some embodiments, this involves the reduction of xylose to xylitol, oxidation of xylitol to xylulose and subsequent conversion of xylulose to xylulose phosphate. In some other embodiments the xylose is directly converted to xylulose which is then phosphorylated to xylulose phosphate.

As used herein the term "xylose pathway enzymes" refers to the enzymes that catalyze the conversion of xylose to xylulose-phosphate. In some embodiments, these enzymes comprise xylose reductase, xylitol dehydrogenase and/or xylulose kinase. In some other embodiments, the enzymes comprise xylose isomerase and xylulose kinase.

DETAILED DESCRIPTION OF THE INVENTION

The present invention provides methods and compositions suitable for use in the conversion of xylose to xylitol and xylulose, including nucleic acid constructs, recombinant fungal host cells, and related materials.

Figure 1:
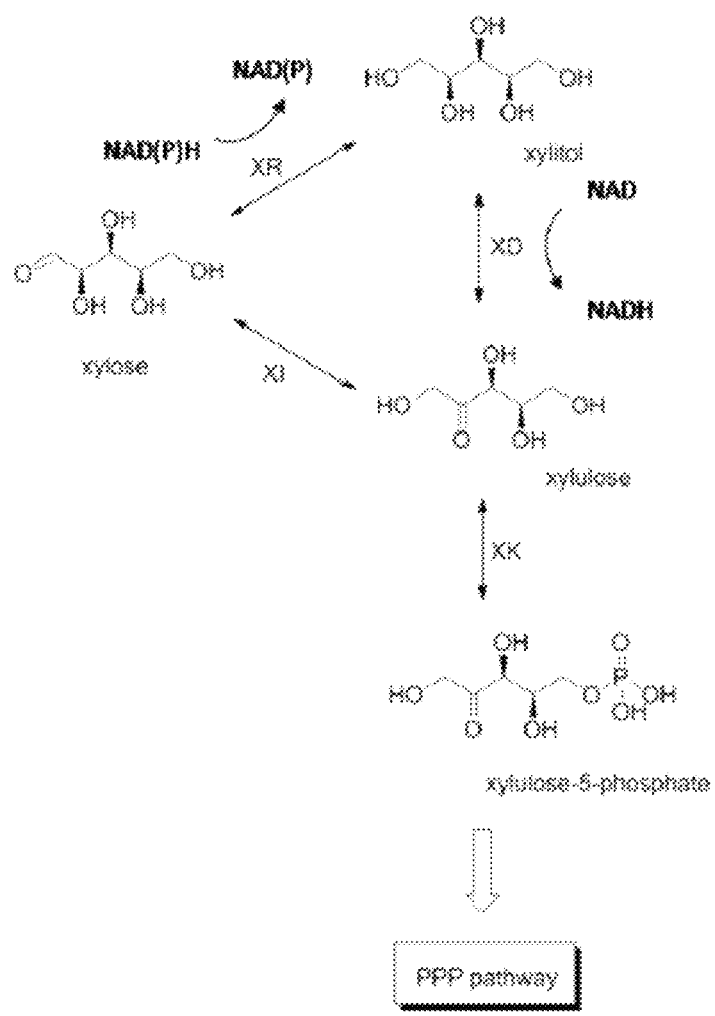
FIG. 1 depicts xylose conversion pathways. In yeast and filamentous fungi, D-xylose is initially reduced to xylitol by NAD(P)H-dependent xylose reductase ("XR"). Xylitol is subsequently oxidized to D-xylulose by NAD+-dependent xylitol dehydrogenase ("XDH" or "XD"). Xylulokinase ("XK") subsequently phosphorylates D-xylulose to produce D-xylulose 5-phosphate, which is then further metabolized through the pentose phosphate pathway ("PPP"). In bacteria, D-xylose is directly converted to D-xylulose by a xylose isomerase ("XI").

The initial metabolic pathways for xylose utilization in fungi and bacteria differ. In most fungi, including xylose-fermenting yeasts (e.g., *Pichia stipitis, Pachysolen tannophilus*, and *Candida shehatae*), D-xylose is converted to D-xylulose by two oxidoreductases involving cofactors NAD(P)H and NAD(P)+. (See, Matsushika et al., Appl. Microbiol. Biotechnol., 84:37-53 [2009]). In these organisms, D-xylose is initially reduced to xylitol by NAD(P)H-dependent xylose reductase ("XR") (EC 1.1.1.21). Xylitol is subsequently oxidized to D-xylulose by NAD+-dependent xylitol dehydrogenase ("XDH" or "XD") (EC 1.1.1.9). Xylulokinase ("XK") (EC 2.7.1.17) subsequently phosphorylates D-xylulose to produce D-xylulose 5-phosphate ("X5P"), which is then further metabolized through the pentose phosphate pathway ("PPP"). FIG. 1 provides a schematic of the pathway.

However, most strains of *S. cerevisiae* cannot utilize xylose even though the genes encoding XR, XDH, and XK are present in its genome, as the expression levels of these enzymes are too low to allow xylose utilization (See, Matsushika et al., supra). Some strains have been shown to natively utilize xylose but at very low rates and fermentation to ethanol has not been detected (See, Wenger et al., PLoS Genet., 6(5):e1000942 [2010]). Even when the endogenous genes are overexpressed in *S. cerevisiae*, only slow growth on xylose has been observed (See, Matsushika et al. supra).

In contrast, most bacteria (e.g., *Escherichia coli* and *Streptomyces* species) can isomerize D-xylose directly to D-xylulose by using a xylose isomerase ("XI") (EC 5.3.1.5) (See, Matsushika et al., supra). In bacteria, as in fungi, the D-xylulose is phosphorylated to D-xylulose 5-phosphate by XK, which is then further metabolized through the pentose phosphate pathway.

Figure 2A:
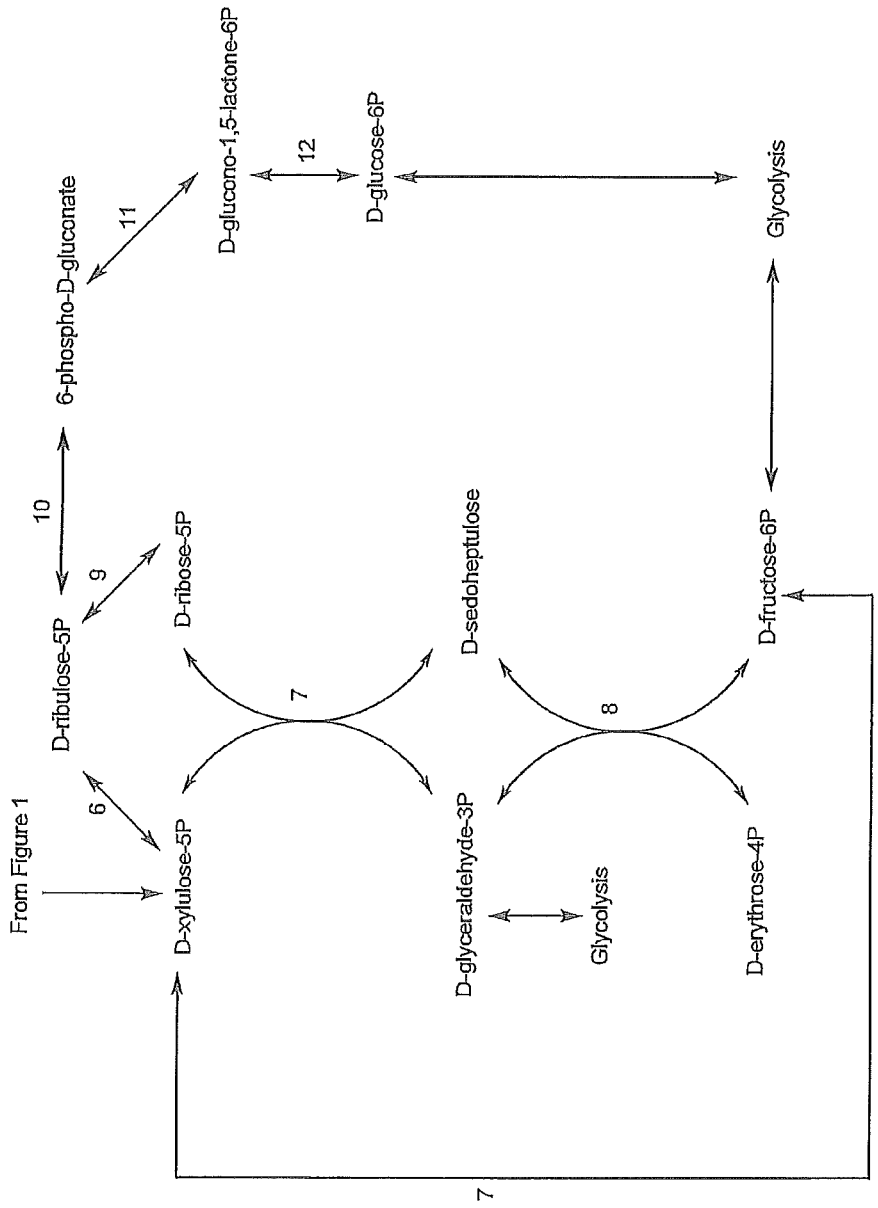
FIGS. 2A-C depict the metabolic pathways for converting D-xylulose-5-P to ethanol.

Xylose utilization by these host cells results in useful products that are produced metabolically by the host cell. In these host cells, D-xylulose may be phosphorylated by a native or recombinant xylulokinase to xylulose-5-P, as depicted in FIG. 1. The xylulose-5-P may be further metabolized by enzymes in the pentose phosphate pathway to products such as glucose-6-P, fructose-6-P, glyceraldehydes-3-P, and the like. The pentose phosphate pathway and relevant enzymes and products are depicted in FIG. 2A. As used herein, the terms "enzyme from the pentose phosphate pathway" and "pentose phosphate pathway enzyme" are used interchangeably to refer to an enzyme from the group of enzymes involved in the pentose phosphate pathway, (i.e., 6. ribulose-5-phosphate ketoisomerase (RK11); 7. transketolase (TKL1); 8. transaldolase (TAL1); 9. ribose-5-phosphate ketolisomerase (RK11); 10. 6-phosphogluconate dehydrogenase (GND1); 11. 6-phosphogluconalactonase (SOL3); and/or 12. glucose-6-phosphate-1-dehydrogenase (ZWF); the reference numbers correspond to those in FIG. 2A).

Figure 2B:
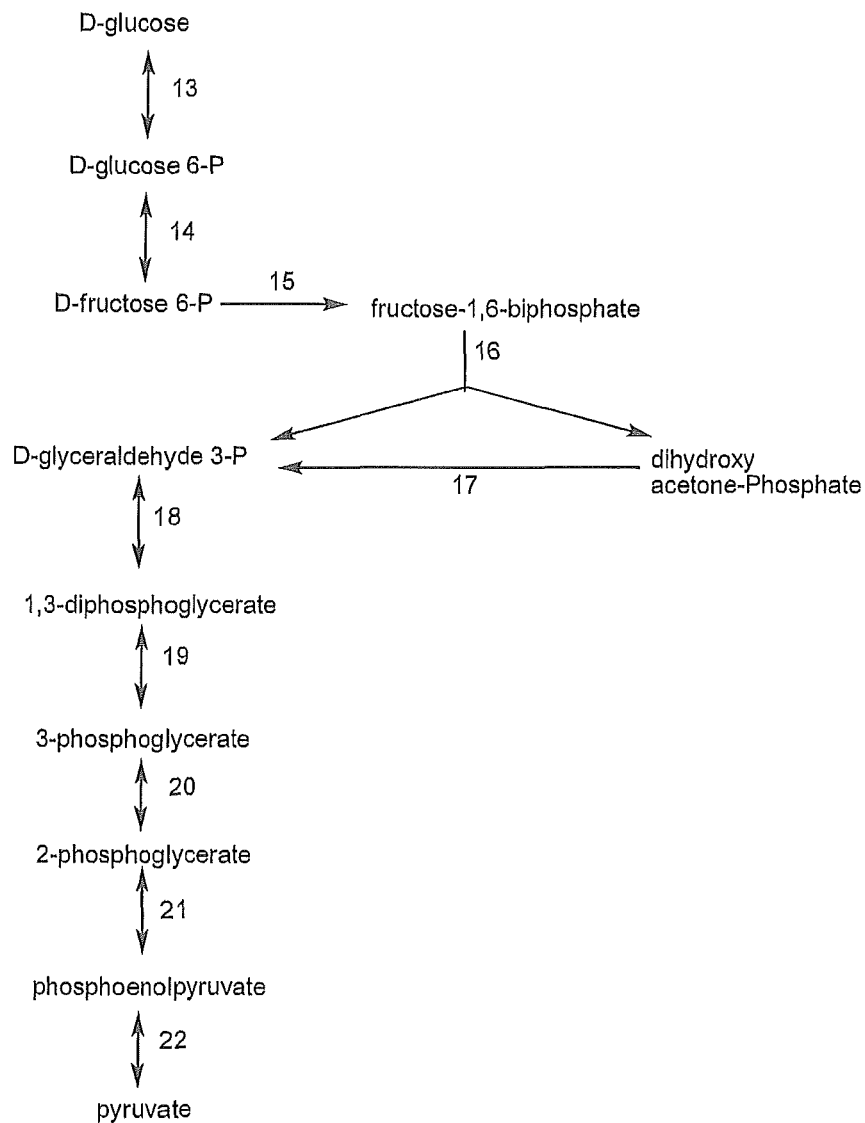

Products of the pentose phosphate pathway may be further metabolized through the process of glycolysis. The metabolic process of glycolysis is depicted in FIG. 2B. As used herein, the term "glycolytic enzyme" refers to an enzyme from the group of enzymes involved in glycolysis (i.e.: 13. hexokinase; 14. phosphoglucose isomerase; 15. phosphofructokinase; 16. aldolase; 17. triose phosphate isomerase; 18. glyceraldehyde phosphate dehydrogenase; 19. phosphoglycerate kinase; 20. phosphglyceromutase; 21. enoase; and/or 22. pyruvate kinase; the reference numbers correspond to those in FIG. 2B).

Figure 2C:
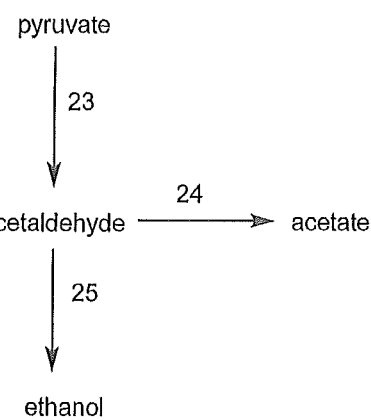

Pyruvate from the glycolytic pathway (i.e., glycolysis) may be further metabolized to ethanol as shown in FIG. 2C by ethanologenic enzymes. As used herein, the term "ethanologenic enzyme" refers to an enzyme involved in the conversion of pyruvate to ethanol, (e.g., a pyruvate decarboxylase, an aldehyde dehydrogenase, and/or an alcohol dehydrogenase). The term "ethanologenic pathway" refers to the pathway depicted in FIG. 2C.

Recombinant host cells transformed with xylose reductase and xylitol dehydrogenase genes are hence capable of converting xylose to xylitol and then converting xylitol to xylulose, which can lead to the production of desirable fermentation products (e.g., an alcohol, such as ethanol, butanol, and the like, including, but not limited to a fatty alcohol [e.g., a C8-C20 fatty alcohol], a fatty acid [e.g., a C8-C20 fatty acid], lactic acid, 3-hydroxpropionic acid, acrylic acid, acetic acid, succinic acid, citric acid, malic acid, fumaric acid, an amino acid, 1,3-propanediol, ethylene, glycerol, a β-lactam, and the like). However, cells transformed with wildtype xylose reductase and xylitol dehydrogenase genes from *Pichia stipitis* convert xylose inefficiently and with accumulation of xylitol (Matsushika et al., Appl. Environ Microbiol., 81:243-55

[2008]). The present application provides improved xylose reductase and xylitol dehydrogenase variants that significantly increase the efficiency of xylose conversion.

Recombinant Nucleic Acid Constructs

The present invention provides recombinant nucleic acid constructs comprising polynucleotide sequences that encode at least one polypeptide comprising an amino acid sequence having at least 70% identity to SEQ ID NO:2, wherein the polypeptide is capable of catalyzing xylose to xylitol, and wherein the polypeptide comprises at least one substitution set forth herein. SEQ ID NO:2 corresponds to the amino acid sequence encoding xylose reductase from the yeast, *Pichia stipitis*. SEQ ID NO:1 corresponds to the native *P. stipitis* polynucleotide sequence that encodes a *P. stipitis* xylose reductase (SEQ ID NO:2), while SEQ ID NOS:3 and 4 correspond to codon-optimized sequences encoding the xylose reductase. In some embodiments, the nucleic acid construct comprises SEQ ID NO:40, while in other embodiments, the nucleic acid construct comprises SEQ ID NO:42, in still other embodiments, the nucleic acid construct comprises SEQ ID NO:44, and in additional embodiments, the nucleic acid construct comprises SEQ ID NO:46. In some embodiments, the polypeptide comprises SEQ ID NO:41, while in other embodiments, the polypeptide comprises SEQ ID NO:43, in still other embodiments, the polypeptide comprises SEQ ID NO:45, and in further embodiments, the polypeptide comprises SEQ ID NO:47.

The present invention also provides a recombinant nucleic acid constructs comprising polynucleotide sequences that encode at least one polypeptide comprising an amino acid sequence having at least 70% identity to SEQ ID NO:6, wherein the polypeptide is capable of catalyzing xylitol to xylulose, and wherein the polypeptide comprises at least one substitution set forth herein. SEQ ID NO:6 corresponds to the amino acid sequence encoding xylitol dehydrogenase from the yeast, *Pichia* SEQ ID NO:5 corresponds to the native *P. stipitis* polynucleotide sequence that encodes a *P. stipitis* xylitol dehydrogenase (SEQ ID NO:6), while SEQ ID NOS:7 and 8 correspond to codon-optimized sequences encoding the xylitol dehydrogenase. In some embodiments, the nucleic acid construct comprises SEQ ID NO:48, while in other embodiments, the nucleic acid construct encodes a polypeptide comprising SEQ ID NO:49.

The present invention also provides recombinant nucleic acid constructs comprising polynucleotide sequences that encode polypeptide sequences having xylose reductase and xylitol dehydrogenase activity. In some embodiments, the nucleic acid constructs comprise at least one of SEQ ID NO:40, 42, 44, and/or 46, and SEQ ID NO:48.

The present invention also provides nucleic acid constructs comprising codon-optimized polynucleotides encoding xylulokinase. In some embodiments, the present invention provides SEQ ID NO:11, while in other embodiments, the present invention provides SEQ ID NO:12.

The present invention also provides nucleic acid constructs comprising polynucleotides encoding xylose reductase, xylitol dehydrogenase and xylulokinase. In some embodiments, the nucleic acid constructs comprise SEQ ID NO:1, 3, 4, 40, 42, 44, and/or 46, as well as SEQ ID NO: 5, 7, 8, and/or 48, and SEQ ID NO:9, 11, and/or 12.

In some embodiments, recombinant nucleic acid constructs of the present invention further comprise a polynucleotide sequence (genetic) element that facilitates integration into a fungal host cell genome, by homologous or non-homologous recombination. In some embodiments, the nucleic acid construct of the present invention further comprises an origin of replication that is functional in a fungal cell (e.g., a yeast origin of replication). Typically, the fungal host cell is a yeast or filamentous fungal cell, more typically, a yeast cell. In some embodiments, nucleic acid constructs of the present invention comprise a transcriptional regulatory element that is functional in a fungal cell. For example, in some embodiments the recombinant nucleic acid construct comprises a promoter sequence and/or transcription terminator sequence that is functional in a fungal cell such that the xylose reductase and/or xylitol dehydrogenase polynucleotide is operatively linked to the promoter sequence and/or transcription terminator sequences.

Xylose reductase and xylitol dehydrogenase polynucleotides that are suitable for use in the practice of the present invention include those encoding variants of SEQ ID NO:2 and/or 6, respectively. These variants include those having amino acid sequences with one or more conservative or non-conservative substitutions relative to the amino acid sequence of SEQ ID NO:2 and/or SEQ ID NO:6. As used herein, the term "conservative substitution" refers to the substitution of a residue for another residue that does not generally alter the specific activity of the encoded polypeptide. An exemplary conservative substitution is a substitution that is within the same group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions that do not generally alter the specific activity are well-known in the art. The most commonly occurring exchanges are Ala/Ser, Val/Ile, Asp/Glu, Thr/Ser, Ala/Gly, Ala/Thr. Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these in reverse.

In some embodiments, polynucleotides encoding conservatively substituted variations of the *P. stipitis* xylose reductase and/or xylitol dehydrogenase employed in the practice of the present invention include substitutions of a small percentage, typically less than about 5%, more typically less than 2%, and often less than about 1% of the amino acids of the polypeptide sequence, with a conservatively selected amino acid of the same conservative substitution group.

Other xylose reductase and/or xylitol dehydrogenase polynucleotides suitable for use in the practice of the present invention include those encoding variants of *P. stipitis* xylose reductase and/or xylitol dehydrogenase generated by mutagenesis, recombination, or other protein engineering method followed by screening of the variants for xylose utilization using a method, such as that described in the Examples. In some embodiments, the resulting variants comprise one or more substitutions (conservative or non-conservative), deletions, and/or insertions. The present invention thus provides methods for making improved *P. stipitis* xylose reductase and xylitol dehydrogenase polynucleotide variants, wherein the method comprises introducing one or more modifications into a polynucleotide encoding SEQ ID NO:1, 3 and/or 4; and/or 5, 7 and/or 8, respectively, to produce a modified polynucleotide, wherein the modification is selected from at least one substitution, at least one deletion, and/or at least one insertion; transforming a host cell with the modified polynucleotide; and screening the transformed host cell for an improvement in a desired phenotype relative to the corresponding untransformed host cell. In some embodiments, the improved variants are screened to assess improvements in a desired phenotype relative to a transformed host cell that has been transformed with wild-type sequences, while in other embodiments, transformed host cells are compared with other transformed host cells. Exemplary phenotypes include improved utilization of a pentose sugar (e.g., xylose, arabinose, etc.), stability, specific activity, lower Ki for xylitol, ethanol/acetate tolerance and/or tolerance to low pH, decreased by-product formation, and/or increased ethanol yield. Exemplary desirable xylose utilization phenotypes include the ability to ferment xylose to ethanol, the ability to ferment xylose to other metabolic intermediates/products, the ability to undergo aerobic or anaerobic growth on xylose, and the like.

Methods for generating variant libraries of polynucleotides encoding modified polypeptides are well known in the art. For example, mutagenesis and directed evolution methods can be readily applied to polynucleotides encoding the xylose reductase polypeptide of SEQ ID NO:2 and/or xylitol dehydrogenase of SEQ ID NO:6, to generate variant libraries that can be expressed, screened, and assayed using the methods described herein. Mutagenesis and directed evolution methods are well known in the art (See e.g., Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In some embodiments, the present invention provides *P. stipitis* polypeptide variants that comprise at least one modification that is a substitution, insertion, and/or deletion relative to SEQ ID NO:2. Typically, the polypeptide variant has from 1 to 2, 1 to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, up to about 50, 75, 100, or 130 modifications.

In some embodiments, the xylose reductase variants of the present invention comprise a substitution at position 276 of wild-type *P. stipitis* xylose reductase. In some alternative embodiments, the xylose reductase variants comprise at least one substitution at positions 2, 49, 132, 233, 267, and/or 276, wherein the positions are numbered by correspondence with the amino acid sequence of *P. stipitis* xylose reductase set forth in SEQ ID NO:2. In some additional embodiments, the substitutions comprise substitutions at R276, P2, A49, K132, S233, I267, and/or R276. In some further embodiments, the substitutions comprise R276W, P2T, A49G, K132N, S233K, I267V, and/or R276W, wherein the positions are numbered by correspondence with the amino acid sequence of *P. stipitis* xylose reductase set forth in SEQ ID NO:2. In some embodiments, the variants comprise substitutions P2T, A49G, and R276W, wherein the positions are numbered by correspondence with the amino acid sequence of *P. stipitis* xylose reductase set forth in SEQ ID NO:2. In some additional embodiments, the variants comprise substitutions P2T, A49G, K132N, S233K, I267V, and R276W, wherein the positions are numbered by correspondence with the amino acid sequence of *P. stipitis* xylose reductase set forth in SEQ ID NO:2. In some additional embodiments, the variants comprise at least one substitution selected from position 2, 3, 7, 11, 14, 17, 23, 24, 33, 36, 46, 47, 49, 56, 62, 68, 89, 97, 102, 108, 114, 116, 123, 132, 134, 143, 152, 155, 157, 162, 168, 184, 206, 219, 224, 225, 226, 228, 246, 231, 232, 233, 236, 240, 242, 245, 246, 249, 252, 255, 261, 266, 267, 275, 276, 279, 281, 282, 283, 285, 297, 301, 302, 303, and 318, wherein the positions are numbered by correspondence with the amino acid sequence of *P. stipitis* xylose reductase set forth in SEQ ID NO:2.

In still some further embodiments, the variants comprise at least one substitution selected from P2, S3, N7, D11, A14, F17, D23, V24, R33, K36, E46, D47, A49, A56, I62, K68, E89, S97, D102, L108, T114, K116, K123, K132, D134, I143, K152, K155, G157, I162, P168, S184, R206, Q219, L224, N225, Q226, R228, A246, N231, T232, S233, F236, T240, K242, A245, A246, G249, P252, V255, S261, A266, I267, P275, R276, E279, K281, D282, V283, S285, A297, I301, N302, L303, and V318, wherein the positions are numbered by correspondence with the amino acid sequence of *P. stipitis* xylose reductase set forth in SEQ ID NO:2.

In some additional embodiments, the substitutions comprise at least one substitution selected from P2T, S3H, S3R, S3W, N7L, D11K, A14V, F17W, D23E, V24G, R33L, R22V, K36Q, E46K, D47G, D47N, A49G, A56E, A56Y, I62V, K68G, K68M, K68R, E89N, E89V, S97R, S97T, D102T, L108Y, T114S, K116Q, K123C, K132A, K132N, D134E, D134H, D134V, I143L, K152A, K152E, K152H, K152Q, K155A, K155D, K155I, K155R, K155Y, G157R, I162L, P168S, S184A, R206S, R206V, Q219H, Q219L, Q219T, L224A, L224S, L224V, N225D, N225E, N225K, N225S, N225Y, Q226D, Q226E, Q226S, Q226V, R228T, N231G, N231H, N231L, N231S, T232A, T232C, T232S, T232V, S233C, S233F, S233G, S233I, S233K, S233V, F236L, T240V, K242L, A245S, A246L, A246S, G249D, P252C, V255I, S261A, S261C, S261N, S261T, A266V, A266C, I267V, P275A, R276M, R276W, E279Q, K281L, K281V, D282C, D282G, D282R, V283H, S285E, S285T, A297H, A297S, I301C, I301Y, N302D, N302G, N302S, L303I, L303V, and V318C, wherein the positions are numbered by correspondence with the amino acid sequence of *P. stipitis* xylose reductase set forth in SEQ ID NO:2.

In some embodiments, the present invention provides polynucleotide sequences encoding xylose reductase variants comprising SEQ ID NO:40, as provided below. In some additional embodiments, the present invention provides polypeptide sequences comprising SEQ ID NO:41, as provided below.

(SEQ ID NO: 40)
ATGCCTTCTATTAAGTTGAACTCTGGTTACGACATGCCAGCCGTCGGTTTCGGCTGTTGGAAA

GTTGACGTTGACACCTGTTCTGAACAGGTCTACCGTGCTATCAAGACCGGTTACAGATTGTT

CGACGGTGCCGAAGATTACGCCAACGAAAAGTTAGTTGGTGCCGGTGTCAAGAAGGCCATT

GACGAAGGTATCGTCAAGCGTGAAGACTTGTTCCTTACCTCCAAGTTGTGGAACAACTACCA

CCACCCAGACAACGTCGAAAAGGCCTTGAACAGAACCCTTTCTGACTTGCAAGTTGACTACG

-continued

```
TTGACTTGTTCTTGATCCACTTCCCAGTCACCTTCAAGTTCGTTCCATTAGAAGAAAAGTACC

CACCAGGATTCTACTGTGGTAAGGGTGACAACTTCGACTACGAAGATGTTCCAATTTTAGAG

ACCTGGAAGGCTCTTGAAAAGTTGGTCAAGGCCGGTAAGATCAGGTCTATCGGTGTTTCTAA

CTTCCCAGGTGCTTTGCTCTTGGACTTGTTGAGAGGTGCTACCATCAAGCCATCTGTCTTGCA

AGTTGAACACCACCCATACTTGCAACAACCAAGATTGATCGAGTTCGCTCAATCCCGTGGTA

TTGCTGTCACCGCTTACTCTTCGTTCGGTCCTCAATCTTTCGTTGAATTGAACCAAGGTAGAG

CTTTGAACACTTCTCCATTGTTCGAGAACGAAACTATCAAGGCTATCGCTGCTAAGCACGGT

AAGTCTCCAGCTCAAGTCTTGTTGAGATGGTCTTCCCAAAGAGGCATTGCCATCATTCCAAA

GTCCAACACTGTCCCATGGTTGTTGGAAAACAAGGATGTCAACAGCTTCGACTTGGACGAAC

AAGATTTCGCTGACATTGCCAAGTTGGACATCAACTTGAGATTCAACGACCCATGGGACTGG

GACAAGATTCCTATCTTCGTCTAA
```

(SEQ ID NO: 41)
```
MPSIKLNSGYDMPAVGFGCWKVDVDTCSEQVYRAIKTGYRLFDGAEDYANEKLVGAGVKKAI

DEGIVKREDLFLTSKLWNNYHHPDNVEKALNRTLSDLQVDYVDLFLIHFPVTFKFVPLEEKYPPG

FYCGKGDNFDYEDVPILETWKALEKLVKAGKIRSIGVSNFPGALLLDLLRGATIKPSVLQVEHHP

YLQQPRLIEFAQSRGIAVTAYSSFGPQSFVELNQGRALNTSPLFENETIKAIAAKHGKSPAQLLR

WSSQRGIAIIPKSNTVPWLLENKDVNSFDLDEQDFADIAKLDINLRFNDPWDWDKIPIFV
```

In some embodiments, the present invention provides polynucleotide sequences encoding xylose reductase variants comprising SEQ ID NO:42, as provided below. In some additional embodiments, the present invention provides polypeptide sequences comprising SEQ ID NO:43, as provided below.

(SEQ ID NO: 42)
```
ATGACCTCTATTAAGTTGAACTCTGGTTACGACATGCCAGCCGTCGGTTTCGGCTGTTGGAA

AGTTGACGTTGACACCTGTTCTGAACAGGTCTACCGTGCTATCAAGACCGGTTACAGATTGT

TCGACGGTGCCGAAGATTACGGCAACGAAAAGTTAGTTGGTGCCGGTGTCAAGAAGGCCAT

TGACGAAGGTATCGTCAAGCGTGAAGACTTGTTCCTTACCTCCAAGTTGTGGAACAACTACC

ACCACCCAGACAACGTCGAAAAGGCCTTGAACAGAACCCTTTCTGACTTGCAAGTTGACTAC

GTTGACTTGTTCTTGATCCACTTCCCAGTCACCTTCAAGTTCGTTCCATTAGAAGAAAAGTAC

CCACCAGGATTCTACTGTGGTAAGGGTGACAACTTCGACTACGAAGATGTTCCAATTTTAGA

GACCTGGAAGGCTCTTGAAAAGTTGGTCAAGGCCGGTAAGATCAGGTCTATCGGTGTTTCTA

ACTTCCCAGGTGCTTTGCTCTTGGACTTGTTGAGAGGTGCTACCATCAAGCCATCTGTCTTGC

AAGTTGAACACCACCCATACTTGCAACAACCAAGATTGATCGAGTTCGCTCAATCCCGTGGT

ATTGCTGTCACCGCTTACTCTTCGTTCGGTCCTCAATCTTTCGTTGAATTGAACCAAGGTAGA

GCTTTGAACACTTCTCCATTGTTCGAGAACGAAACTATCAAGGCTATCGCTGCTAAGCACGG

TAAGTCTCCAGCTCAAGTCTTGTTGAGATGGTCTTCCCAAAGAGGCATTGCCATCATTCCAA

AGTCCAACACTGTCCCATGGTTGTTGGAAAACAAGGATGTCAACAGCTTCGACTTGGACGAA

CAAGATTTCGCTGACATTGCCAAGTTGGACATCAACTTGAGATTCAACGACCCATGGGACTG

GGACAAGATTCCTATCTTCGTCTAA
```

(SEQ ID NO: 43)
```
MTSIKLNSGYDMPAVGFGCWKVDVDTCSEQVYRAIKTGYRLFDGAEDYGNEKLVGAGVKKAI

DEGIVKREDLFLTSKLWNNYHHPDNVEKALNRTLSDLQVDYVDLFLIHFPVTFKFVPLEEKYPPG

FYCGKGDNFDYEDVPILETWKALEKLVKAGKIRSIGVSNFPGALLLDLLRGATIKPSVLQVEHHP
```

-continued
YLQQPRLIEFAQSRGIAVTAYSSFGPQSFVELNQGRALNTSPLFENETIKAIAAKHGKSPAQVLLR

WSSQRGIAIIPKSNTVPWLLENKDVNSFDLDEQDFADIAKLDINLRFNDPWDWDKIPIFV

In some embodiments, the present invention provides polynucleotide sequences encoding xylose reductase variants comprising SEQ ID NO:44, as provided below. In some additional embodiments, the present invention provides polypeptide sequences comprising SEQ ID NO:45, as provided below.

```
(SEQ ID NO: 44)
ATGACCTCTATTAAGTTGAACTCTGGTTACGACATGCCAGCCGTCGGTTTCGGCTGTTGGAA

AGTTGACGTTGACACCTGTTCTGAACAGGTCTACCGAGCTATCAAGACCGGTTACAGATTGT

TCGACGGTGCCGAAGATTACGGCAACGAAAAATTAGTTGGTGCCGGTGTCAAGAAGGCCAT

TGACGAAGGTATCGTCAAGCGTGAAGACTTGTTCCTTACCTCCAAGTTGTGGAACAACTACC

ACCACCCAGACAACGTCGAAAAGGCCTTGAACAGAACCCTTTCTGACTTGCAAGTTGACTAC

GTTGACTTGTTCTTGATCCACTTCCCAGTCACCTTCAAGTTCGTTCCATTAGAAGAAAGTAC

CCACCAGGATTCTACTGTGGTAACGGTGACAACTTCGACTACGAAGATGTTCCAATTTTAGA

GACCTGGAAGGCTCTTGAAAAGTTGGTCAAGGCCGGTAAGATCAGGTCTATCGGTGTTTCTA

ACTTCCCAGGTGCTTTGCTCTTGGACTTGTTGAGAGGTGCTACCATCAAGCCATCTGTCTTGC

AAGTTGAACACCACCCATACTTGCAACAACCAAGATTGATCGAGTTCGCTCAATCCCGTGGT

ATTGCTGTCACCGCTTACTCTTCGTTCGGTCCTCAATCTTTCGTTGAATTGAACCAAGGTAGA

GCTTTGAACACTAAGCCATTGTTCGAGAACGAAACTATCAAGGCTATCGCTGCTAAGCACGG

CAAGAGCCCAGCTCAAGTCTTGTTGAGATGGTCTTCCCAAAGAGGCATTGCCGTTATTCCAA

AGTCCAACACTGTCCCATGGTTGTTGGAAAACAAGGATGTCAACAGCTTCGACTTGGACGAA

CAAGATTTCGCTGACATTGCCAAGTTGGACATCAACTTGAGATTCAACGACCCATGGGACTG

GGACAAGATTCCTATCTTCGTCTAA
```

```
(SEQ ID NO: 45)
MTSIKLNSGYDMPAVGFGCWKVDVDTCSEQVYRAIKTGYRLFDGAEDYGNEKLVGAGVKKAI

DEGIVKREDLFLTSKLWNNYHHPDNVEKALNRTLSDLQVDYVDLFLIHFPVTFKFVPLEEKYPPG

FYCGNGDNFDYEDVPILETWKALEKLVKAGKIRSIGVSNFPGALLLDLLRGATIKPSVLQVEHHP

YLQQPRLIEFAQSRGIAVTAYSSFGPQSFVELNQGRALNTKPLFENETIKAIAAKHGKSPAQVLLR

WSSQRGIAVIPKSNTVPWLLENKDVNSFDLDEQDFADIAKLDINLRFNDPWDWDKIPIFV
```

In some embodiments, the present invention provides polynucleotide sequences encoding xylose reductase variants comprising SEQ ID NO:46, as provided below. In some additional embodiments, the present invention provides polypeptide sequences comprising SEQ ID NO:47, as provided below.

```
(SEQ ID NO: 46)
ATGCCTTCTATTAAGTTGAACTCTGGTTACGACATGCCAGCCGTCGGTTTCGGCTGTTGGAAA

GTTGACGTTGACACCTGTTCTGAACAGGTCTACCGTGCTATCAAGACCGGTTACAGATTGTT

CGACGGTGCCGAAGATTACGCCAACGAAAAGTTAGTTGGTGCCGGTGTCAAGAAGGCCATT

GACGAAGGTATCGTCAAGCGTGAAGACTTGTTCCTTACCTCCAAGTTGTGGAACAACTACCA

CCACCCAGACAACGTCGAAAAGGCCTTGAACAGAACCCTTTCTGACTTGCAAGTTGACTACG

TTGACTTGTTCTTGATCCACTTCCCAGTCACCTTCAAGTTCGTTCCATTAGAAGAAAGTACC

CACCAGGATTCTACTGTGGTAAGGGTGACAACTTCGACTACGAAGATGTTCCAATTTTAGAG

ACCTGGAAGGCTCTTGAAAAGTTGGTCAAGGCCGGTAAGATCAGGTCTATCGGTGTTTCTAA
```

-continued

```
CTTCCCAGGTGCTTTGCTCTTGGACTTGTTGAGAGGTGCTACCATCAAGCCATCTGTCTTGCA

AGTTGAACACCACCCATACTTGCAACAACCAAGATTGATCGAGTTCGCTCAATCCCGTGGTA

TTGCTGTCACCGCTTACTCTTCGTTCGGTCCTCAATCTTTCGTTGAATTGAACCAAGGTAGAG

CTTTGAACACTTCTCCATTGTTCGAGAACGAAACTATCAAGGCTATCGCTGCTAAGCACGGT

AAGTCTCCAGCTCAAGTCTTGTTGAGATGGTCTTCCCAAAGAGGCATTGCCATCATTCCAAA

GAGCAATACTGTCCCATTCTTGTTGGAAAACAAGGATGTCAACAGCTTCGACTTGGACGAAC

AAGATTTCGCTGACATTGCCAAGTTGGACATCAACTTGAGATTCAACGACCCATGGGACTGG

GACAAGATTCCTATCTTCGTCTAA
```

(SEQ ID NO: 47)
```
MPSIKLNSGYDMPAVGFGCWKVDVDTCSEQVYRAIKTGYRLFDGAEDYANEKLVGAGVKKAI

DEGIVKREDLFLTSKLWNNYHHPDNVEKALNRTLSDLQVDYVDLFLIHFPVTFKFVPLEEKYPPG

FYCGKGDNFDYEDVPILETWKALEKLVKAGKIRSIGVSNFPGALLLDLLRGATIKPSVLQVEHHP

YLQQPRLIEFAQSRGIAVTAYSSFGPQSFVELNQGRALNTSPLFENETIKAIAAKHGKSPAQVLLR

WSSQRGIAIIPKSNTVPFLLENKDVNSFDLDEQDFADIAKLDINLRFNDPWDWDKIPIFV
```

In some embodiments, the present invention also provides nucleic acid substitutions in sequences encoding xylose reductase variants (e.g., SEQ ID NOS:1, 3 and/or 4). In some embodiments, the nucleic acids comprise substitutions at positions 42, 82, 99, 156, 201, 280, 306, 354, 358, 378, 408, 438, 478, 511, 585, 670, 688, 703, 747, 751, 766, 855, 849, and/or 906, wherein the positions are numbered by correspondence with the nucleic acid sequence of P. stipitis xylose reductase set forth in SEQ ID NO:1, 3 and/or 4. In some embodiments, the substitutions comprise t82a, t99a, g156a, c201t, a280c, c306t, t354g, t358c, a378t, c408t, a426t, c438t, a478c, t511c, a585g, t670c, t688c, t703c, t747c, t751a, t766c, c849g, c855t, and/or c906t, wherein the positions are numbered by correspondence with the nucleic acid sequence of P. stipitis xylose reductase set forth in SEQ ID NO:1, 3 and/or 4.

In some embodiments, the present invention further provides xylitol dehydrogenase variants comprising at least one substitution at positions 5, 13, 19, 49, 81, 149, 187, 189, 202, 205, 206, 208, 209, 211, 215, 218, 226, 227, 228, 229, 231, 235, 239, 241, 251, 252, 256, 260, 287, 296, 307, 327, 350, and/or 352, wherein the positions are numbered by correspondence with the amino acid sequence of P. stipitis xylose reductase set forth in SEQ ID NO:6.

In some embodiments, the xylitol dehydrogenase variants comprise substitution at position 208, wherein the positions are numbered by correspondence with the amino acid sequence of P. stipitis xylitol dehydrogenase set forth in SEQ ID NO:6. In some embodiments, the substitution at position 208 is I208X. In some further embodiments, the substitution at position 208 is I208R. In some embodiments, the xylitol dehydrogenase variants comprise substitutions at position 211, wherein the positions are numbered by correspondence with the amino acid sequence of P. stipitis xylitol dehydrogenase set forth in SEQ ID NO:6. In some embodiments, the substitution at position 211 is N211X. In some further embodiments, the substitution is N211K, while in other embodiments, the substitution is N211S, and in still other embodiments, the substitution is N211K.

In some embodiments, the xylitol dehydrogenase variants comprise substitutions at positions 208 and 211, wherein the positions are numbered by correspondence with the amino acid sequence of P. stipitis xylitol dehydrogenase set forth in SEQ ID NO:6. In some embodiments, the substitution at position 208 is I208X and the substitution at position 211 is N211X. In some further embodiments, the substitutions comprise I208R and N211K, while in some other embodiments, the substitutions comprise I208R and N211S.

In some embodiments, the xylitol dehydrogenase variants comprise substitutions at positions 209 and 211, wherein the positions are numbered by correspondence with the amino acid sequence of P. stipitis xylitol dehydrogenase set forth in SEQ ID NO:6. In some embodiments, the substitutions are F209X and N211X.

In some embodiments, the xylitol dehydrogenase variants comprise substitutions at positions 208, 209 and 211, wherein the positions are numbered by correspondence with the amino acid sequence of P. stipitis xylitol dehydrogenase set forth in SEQ ID NO:6. In some embodiments, the substitutions are I208X, F209X, and N211X. In some further embodiments, the substitutions are I208R, F209S, and N211S.

In some embodiments, the present invention also provides nucleic acid substitutions in sequences encoding xylitol dehydrogenase variants (e.g., SEQ ID NOS:5, 7, and/or 8). In some embodiments, the nucleic acids comprise substitutions at positions t24g, c630t, a732g, a768t, and/or a780g, wherein the positions are numbered by correspondence with the nucleic acid sequence of P. stipitis xylose reductase set forth in SEQ ID NO:5, 7 and/or 8.

In some embodiments, the present invention provides polypeptides that comprise XR and XD substitutions, including, but not limited to combinations of substitutions at positions 271, 270, 272, and/or 276 in XR (wherein the positions are numbered by correspondence with SEQ ID NO:2) and substitutions at positions 208, 209, and/or 211 in XD (wherein the positions are numbered by correspondence with SEQ ID NO:6). In some embodiments, the substitutions comprise substitutions S271X, K270, N272, and/or R276 in XR (wherein the positions are numbered by correspondence with SEQ ID NO:2) and substitutions I208X, F209X, and/or N211X in XD (wherein the positions are numbered by correspondence with SEQ ID NO:6). In some embodiments, the substitutions comprise substitutions S271G, K270R, N272P, and/or R276F in XR (wherein the positions are numbered by correspondence with SEQ ID NO:2) and substitutions I208R, F209S, and/or N211K in XD (wherein the positions are numbered by correspondence with SEQ ID NO:6).

In some embodiments, the substitutions comprise R276F in XR (wherein the position is numbered by correspondence with SEQ ID NO:2), and I208R in XD (wherein the position is numbered by correspondence with SEQ ID NO:6). In some embodiments, the substitutions comprises R276F in XR (wherein the position is numbered by correspondence with SEQ ID NO:2), and F209S and N211K in XD (wherein the positions are numbered by correspondence with SEQ ID NO:6). In some embodiments, the substitutions comprise S271G in XR (wherein the position is numbered by correspondence with SEQ ID NO:2), and I208R and N211K in XD (wherein the positions are numbered by correspondence with SEQ ID NO:6). In some embodiments, the substitutions comprise S271G in XR (wherein the position is numbered by correspondence with SEQ ID NO:2), and I208R and N211S in XD (wherein the positions are numbered by correspondence with SEQ ID NO:6). In some embodiments, the substitutions comprise R276F in XR (wherein the position is numbered by correspondence with SEQ ID NO:2), and I208R, F209S and N211K in XD (wherein the positions are numbered by correspondence with SEQ ID NO:6). In some embodiments, the substitutions comprise S271G in XR (wherein the position is numbered by correspondence with SEQ ID NO:2), and I208R in XD (wherein the positions are numbered by correspondence with SEQ ID NO:6). In some embodiments, the substitutions comprise K270R in XR (wherein the position is numbered by correspondence with SEQ ID NO:2), and I208R and N211R in XD (wherein the positions are numbered by correspondence with SEQ ID NO:6). In some embodiments, the substitutions comprise K270R in XR (wherein the position is numbered by correspondence with SEQ ID NO:2), and F209S and N211K in XD (wherein the positions are numbered by correspondence with SEQ ID NO:6). In some embodiments, the substitutions comprise N272P and R276F in XR (wherein the position is numbered by correspondence with SEQ ID NO:2), and F209S and N211K in XD (wherein the positions are numbered by correspondence with SEQ ID NO:6). In some embodiments, the substitutions comprise K270R, N272P and R276F in XR (wherein the position is numbered by correspondence with SEQ ID NO:2), and N211K in XD (wherein the positions are numbered by correspondence with SEQ ID NO:6).

In some additional embodiments, the present invention provides XR and XD variants having amino acid and nucleic acid substitutions, wherein amino acid substitutions in SEQ ID NO:2 comprises R276F, amino acid substitutions in SEQ ID NO:6 comprise I208R, and the nucleic acid substitutions comprise t811a and c816t in SEQ ID NO:1, 3 and/or 4. In some additional embodiments, the present invention provides XR and XD variants having amino acid and nucleic acid substitutions, wherein amino acid substitutions in SEQ ID NO:2 comprise R276F, amino acid substitutions in SEQ ID NO:6 comprise F209S and N211K, and the nucleic acid substitutions comprise t811a and c816t in SEQ ID NO:1, 3 and/or 4. In some additional embodiments, the present invention provides XR and XD variants having amino acid and nucleic acid substitutions, wherein amino acid substitutions in SEQ ID NO:2 comprise S271G, amino acid substitutions in SEQ ID NO:6 comprise I208R and N211K, and the nucleic acid substitutions comprise c816t and a826c in SEQ ID NO:1, 3 and/or 4. In some additional embodiments, the present invention provides XR and XD variants having amino acid and nucleic acid substitutions, wherein amino acid substitutions in SEQ ID NO:2 comprise S271G, amino acid substitutions in SEQ ID NO:6 comprise I208R and N211S, and the nucleic acid substitutions comprise c816t and a826c in SEQ ID NO:1, 3 and/or 4. In some additional embodiments, the present invention provides XR and XD variants having amino acid and nucleic acid substitutions, wherein amino acid substitutions in SEQ ID NO:2 comprise R276F, amino acid substitutions in SEQ ID NO:6 comprise I208R, F209S and N211K, and the nucleic acid substitutions comprise t811a and c816t in SEQ ID NO:1, 3 and/or 4. In some additional embodiments, the present invention provides XR and XD variants having amino acid and nucleic acid substitutions, wherein amino acid substitutions in SEQ ID NO:2 comprise S271G, amino acid substitutions in SEQ ID NO:6 comprise I208R, and the nucleic acid substitutions comprise c816t and a826c in SEQ ID NO:1, 3 and/or 4. In some additional embodiments, the present invention provides XR and XD variants having amino acid and nucleic acid substitutions, wherein amino acid substitutions in SEQ ID NO:2 comprise K270R, amino acid substitutions in SEQ ID NO:6 comprise I208R and N211R, and the nucleic acid substitutions comprise t811a, c816t, and a826c, in SEQ ID NO:1, 3 and/or 4. In some additional embodiments, the present invention provides XR and XD variants having amino acid and nucleic acid substitutions, wherein amino acid substitutions in SEQ ID NO:2 comprise K270R, amino acid substitutions in SEQ ID NO:6 comprise F209S and N211K, and the nucleic acid substitutions comprise t811a, c816t, and a826c, in SEQ ID NO:1, 3 and/or 4. In some additional embodiments, the present invention provides XR and XD variants having amino acid and nucleic acid substitutions, wherein amino acid substitutions in SEQ ID NO:2 comprise K272P and R276F, amino acid substitutions in SEQ ID NO:6 comprise F209S and N211K, and the nucleic acid substitutions comprise t811a in SEQ ID NO:1, 3 and/or 4. In some additional embodiments, the present invention provides XR and XD variants having amino acid and nucleic acid substitutions, wherein amino acid substitutions in SEQ ID NO:2 comprise K270R, N272P, and R276F, amino acid substitutions in SEQ ID NO:6 comprise N211K, and the nucleic acid substitutions comprise t811a in SEQ ID NO:1, 3 and/or 4. In some additional embodiments, the present invention provides XR and XD variants having amino acid and nucleic acid substitutions, wherein amino acid substitutions in SEQ ID NO:6 comprise I208R, and the nucleic acid substitutions comprise t811a, c816t, and a826c, in SEQ ID NO:1, 3 and/or 4.

In some embodiments, the present invention provides polynucleotide sequences encoding xylitol dehydrogenase variants comprising SEQ ID NO:48, as provided below. In some additional embodiments, the present invention provides polypeptide sequences comprising SEQ ID NO:49, as provided below.

(SEQ ID NO: 48)
ATGACCGCTAATCCCTCTCTTGTTTTGAATAAGATTGACGACATTTCTTTTGAAACTTACGAT

GCTCCCGAAATTAGCGAACCCACAGACGTTTTAGTTCAAGTTAAAAAAACTGGTATCTGCGG

TTCTGACATCCACTTCTACGCTCATGGAAGGATCGGCAACTTCGTCTTAACAAAGCCAATGG

-continued

```
TTCTGGGTCATGAAAGCGCGGGTACTGTTGTTCAAGTCGGTAAAGGTGTTACTTCACTGAAG

GTTGGTGATAACGTCGCAATCGAGCCCGGTATTCCATCTAGGTTCAGTGATGAGTACAAATC

TGGTCACTACAACCTGTGTCCACACATGGCATTTGCTGCTACTCCCAATTCTAAAGAGGGTG

AACCAAACCCACCAGGAACTCTATGTAAGTACTTCAAATCTCCAGAAGACTTCCTGGTTAAG

TTACCCGATCATGTTTCTTTGGAGTTGGGTGCTTTGGTCGAGCCACTATCTGTTGGGGTCCAT

GCTAGTAAATTAGGCTCCGTTGCATTTGGCGATTACGTTGCTGTTTTTGGTGCTGGTCCAGTA

GGATTACTGGCTGCCGCTGTCGCTAAGACATTTGGTGCCAAGGGTGTGATTGTCGTTGATAT

ATCTGACAAGAAGCTGAAGATGGCCAAAGACATAGGTGCCGCTACACATACCTTCAACTCC

AAGACGGGAGGTAGTGAAGAATTGATCAAAGCCTTCGGTGGTAATGTACCAAATGTTGTCTT

GGAATGTACTGGGGCTGAACCATGTATTAAGCTAGGTGTTGATGCCATCGCACCAGGTGGTA

GATTCGTGCAAGTTGGTAATGCTGCTGGTCCCGTGTCCTTTCCCATAACAGTGTTCGCTATGA

AAGAACTTACTTTGTTTGGTTCATTTCGTTATGGTTTCAACGACTATAAGACAGCCGTGGGTA

TCTTTGATACTAACTACCAGAACGGTAGAGAGAATGCTCCCATTGACTTTGAACAGCTTATC

ACGCACAGATACAAATTCAAAGACGCCATTGAAGCCTACGACCTAGTAAGAGCAGGTAAAG

GGGCTGTCAAGTGTTTGATTGATGGTCCAGAATAA
```

(SEQ ID NO: 49)
MTANPSLVLNKIDDISFETYDAPEISEPTDVLVQVKKTGICGSDIHFYAHGRIGNFVLTKPMVLGH

ESAGTVVQVGKGVTSLKVGDNVAIEPGIPSRFSDEYKSGHYNLCPHMAFAATPNSKEGEPNPPGT

LCKYFKSPEDFLVKLPDHVSLELGALVEPLSVGVHASKLGSVAFGDYVAVFGAGPVGLLAAAV

AKTFGAKGVIVVDISDKKLKMAKDIGAATHTFNSKTGGSEELIKAFGGNVPNVVLECTGAEPCIK

LGVDAIAPGGRFVQVGNAAGPVSFPITVFAMKELTLFGSFRYGFNDYKTAVGIFDTNYQNGREN

APIDFEQLITHRYKFKDAIEAYDLVRAGKGAVKCLIDGPE

In some embodiments, the present invention provides polynucleotide sequences encoding xylose reductase variants comprising SEQ ID NO:46 and xylitol dehydrogenase variants comprising SEQ ID NO:48. In some additional embodiments, the present invention provides polypeptide sequences comprising SEQ ID NO:47 and SEQ ID NO:49.

Also suitable for use in the practice of the present invention are polynucleotides encoding a truncated variant of *P. stipitis* xylose reductase and/or a truncated variant xylitol dehydrogenase capable of catalyzing xylose to xylitol and/or xylitol to xylulose. In some embodiments, these truncation variants are truncated at the carboxy (C)-terminus and/or the amino (N)-terminus. Typically, the truncation is from about 1 to about 50 amino acid residues in length.

Those having ordinary skill in the art will understand that due to the degeneracy of the genetic code, a multitude of nucleotide sequences that encode the xylose isomerase polypeptides described herein exist. Table 1 provides the standard triplet genetic code for each amino acid. For example, the codons AGA, AGG, CGA, CGC, CGG, and CGU all encode the amino acid arginine. Thus, at every position in the nucleic acids referred to herein, where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

TABLE 1

Genetic Code

| Amino Acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |

TABLE 1-continued

Genetic Code

| Amino Acids | | | Codon |
|---|---|---|---|
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In some embodiments, DNA sequences are designed for high codon usage bias (i.e., codons that are used at higher frequency in the protein coding regions than other codons that code for the same amino acid). In some embodiments, the preferred codons are determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available (See e.g., Henaut and Danchin in Neidhardt et al. [eds.], *Escherichia coli and Salmonella*, ASM Press, Washington D.C., [1987], p. 2047-2066, which is incorporated herein by reference).

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See, GCG CodonPreference, Genetics Computer Group Wisconsin Package; Peden, *Codon W*, University of Nottingham; McInerney, Bioinform., 14:372-73 [1998]; Stenico et al., Nucl. Acids Res. 222437-46 [1994]; Wright, Gene 87:23-29 [1990]; Wada et al., Nucl. Acids Res., 20:2111-2118 [1992]; Nakamura et al., Nucl. Acids Res., 28:292 [2000]; and Henaut and Danchin, supra; all of which are incorporated herein by reference). The data source for obtaining codon usage may rely on any available nucleotide sequence capable of coding for a protein. These data sets include nucleic acid sequences actually known to express proteins (e.g., complete protein coding sequences-CDS), expressed sequence tags (ESTs), or predicted coding regions of genomic sequences (See e.g., Mount, *Bioinformatics: Sequence and Genome Analysis*, Chapter 8, Cold Spring Harbor Laboratory Press, Cold Spring Harbor, N.Y., [2001]; Uberbacher, Methods Enzymol., 266:259-281 [1996]; and Tiwari et al., Comput. Appl. Biosci. 13:263-270 [1997]; all of which are incorporated herein by reference).

In some embodiments, the xylose reductase and xylitol dehydrogenase polynucleotides contain codons optimized for expression in a fungal cell, particularly a yeast cell. In some embodiments, codon-optimized xylose reductase polynucleotide sequence is provided as SEQ ID NOS:3 and 4. In addition, codon-optimized xylitol dehydrogenase polynucleotides are provided herein (SEQ ID NOS:7 and 8), as well as codon-optimized xylulokinase polynucleotides (SEQ ID NOS:11 and 12). In some embodiments, the codon-optimized sequences provide various advantages, as compared to the corresponding wild-type *S. cerevisiae* sequence(s).

Certain silent mutations have been identified in *P. stipitis* xylose reductase and xylitol dehydrogenase polynucleotide variants that appear to confer the property of greater xylose utilization in transformed *Saccharomyces cerevisiae*. These variants are described in the Examples. The silent mutations include t24g, t82a, t99a, g156a, c201t, a280c, c306t, t354g, t358c, a378t, c408t, a426t, c438t, a478c, t511c, a585g, c630t, t670c, t688c, t703c, a732g, t747c, t751a, t766c, a768t, a780g, t811a, c816t, a826c, c849g, c855t, and c906t (where the nucleotide position is determined by alignment with SEQ ID NO:1). However, it is not intended that the present invention be limited to these particular substitutions as alternative substitutions find use in the present invention.

In some embodiments, the xylose reductase and/or xylitol dehydrogenase polynucleotides are employed in recombinant nucleic acid constructs that comprise a vector (e.g., a plasmid, a cosmid, a phage, a virus, a yeast artificial chromosome (YAC), and the like), into which a xylose reductase and/or xylitol dehydrogenase polynucleotide sequence has been inserted. The xylose reductase and xylitol dehydrogenase polynucleotides provided herein find use when incorporated into any one of a variety of vectors. Suitable vectors include, but are not limited to chromosomal, nonchromosomal and synthetic DNA sequences, yeast plasmids, vectors derived from combinations of plasmids and phage DNA, and many others. Any suitable vector that transduces genetic material into a cell, and, if replication is desired, which is replicable and viable in the relevant host find use in the present invention.

Nucleic acid constructs of the present invention find use in transforming a host cell to permit the host to express the xylose reductase and/or xylitol dehydrogenase polypeptide. Methods for recombinant expression of proteins in fungi are well known in the art, and a number of vectors are available or can be constructed using routine methods (See e.g., Zhu et al., Plasmid 6:128-33 [2009], incorporated herein by reference; and the many standard reference works in this field).

In some embodiments, recombinant nucleic acid constructs of the present invention further comprise a transcriptional regulatory element that is functional in a fungal cell. In some embodiments, the nucleic acid construct comprises the xylose reductase and/or xylitol dehydrogenase polynucleotide operatively linked to a transcriptional regulatory sequence (e.g., a promoter, transcription termination sequence, and the like), that is functional in a fungal cell. Examples of promoters that are functional in a fungal host cell include, but are not limited to promoters from yeast and filamentous fungi. Promoters that are suitable for use in the practice of the present invention include endogenous or heterologous promoters and include both constitutive and inducible promoters that are natural or modified. Particularly useful promoters are those that are insensitive to catabolite (glucose) repression and/or do not require xylose for induction. Such promoters are well known in the art. In some embodiments, a promoter sequence is operably linked to the 5' region of the xylose isomerase or xylitol dehydrogenase coding sequence using routine methods that are well known in the art.

Promoters that are suitable for use in the practice of the present invention include, but are not limited to yeast promoters from glycolytic genes (e.g., yeast phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters, and the like; See e.g., WO 93/03159, which is incorporated herein by reference); promoters of glucose transporters; ribosomal protein encoding gene promoters; alcohol dehydrogenase promoters (e.g., ADH1, ADH4, and the like), and the enolase promoter (ENO).

Exemplary promoters that are useful for directing the transcription of the nucleic acid constructs of the present invention in yeast host cells include, but are not limited to those from the genes for *Saccharomyces cerevisiae* enolase (eno-1), *Saccharomyces cerevisiae* galactokinase (gal1), *Saccharomyces cerevisiae* alcohol dehydrogenase/glyceraldehyde-3-phosphate dehydrogenase (ADH1/ADH2/GAP), and *Saccharomyces cerevisiae* 3-phosphoglycerate kinase, *Saccharomyces cerevisiae* transcription elongation factor (TEF), *Saccharomyces cerevisiae* fructose 1,6-bisphosphate aldolase (FBA1), and *Saccharomyces cerevisiae* 3-phosphate glycerate kinase (PGK1). Other useful promoters for yeast host cells are well known in the art (See e.g., Romanos et al., Yeast 8:423-488 [1992], which is incorporated herein by reference).

Suitable filamentous fungal promoters that are useful in the practice of the present invention include, but are not limited to promoters obtained from the genes for *Aspergillus oryzeae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xyn1, amy, and glaA (See, Nunberg et al., Mol. Cell. Biol., 4:2306-2315 [1984]; Boel et al., EMBO J. 3:1581-85 [1984]; and EP 0 137 280A, all of which are incorporated herein by reference), and mutant, truncated, and hybrid promoters thereof. Promoters associated with chitinase production in fungi also find use in sme embodiments (See e.g., Blaiseau and Lafay, Gene 120: 243-248 [1992] [filamentous fungus *Aphanocladium album*]; and Limon et al., Curr. Genet., 28:478-83 [1995] [*Trichoderma harzianum*]; both of which are incorporated herein by reference).

Any other suitable promoter sequence that drives expression in a fungal host cell, particularly a yeast host cell finds use in the present invention. Suitable promoter sequences can be identified using well known methods. In one approach, a putative promoter sequence is linked 5' to a sequence encoding a reporter protein, the construct is transfected into the host cell and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (See, Henriksen et al., Microbiol., 145:729-34 [1999], which is incorporated herein by reference) or a lacZ reporter gene (See, Punt et al., Gene, 197:189-93 [1997], which is incorporated herein by reference). In some embodiments, functional promoters are derived from naturally occurring promoter sequences by directed evolution methods (See e.g., Wright et al., Hum. Gene Ther., 16:881-892 [2005], which is incorporated herein by reference).

Exemplary transcription termination sequences (terminators) that are functional in a fungal host cell, include transcription termination sequences from yeast and filamentous fungi, that are well known in the art. In some embodiments, the transcription termination sequence is from a yeast. Exemplary yeast transcription termination sequences include, but are not limited to CYC1, ADH1t, ADH2t, etc. In some embodiments, the nucleic acid constructs of the present invention contain a ribosome binding site for translation initiation. In some embodiments, the construct includes appropriate sequences for amplifying expression (e.g., an enhancer). Such elements are well known in the art and any suitable enhancers and/or transcription termination sequences, and/or ribosome binding sites find use in the present invention.

In some additional embodiments, nucleic acid constructs of the present invention contain one or more selectable marker genes to provide a phenotypic trait for selection of transformed host cells. Suitable marker genes include, but are not limited to those coding for antimicrobial resistance such as, ampicillin (ampR), kanamycin, chloramphenicol, tetracycline, streptomycin or spectinomycin (e.g., the aada gene); including but not limited to the streptomycin phosphotransferase (spt) gene coding for streptomycin resistance, the neomycin phosphotransferase (nptII) gene encoding kanamycin or geneticin resistance, the nourseothricin actetyltransferase (nat1) gene coding for nourseothricin resistance, the hygromycin phosphotransferase (hpt) gene coding for hygromycin resistance, genes encoding dihydrofolate reductase, phleomycin, or neomycin resistance for eukaryotic cell culture, and tetracycline or ampicillin resistance in *E. coli*, as well as other marker genes that are well known in the art.

Nucleic acid constructs of the present invention typically comprise a fungal origin of replication, such as, for example, a filamentous fungal or yeast origin of replication. Typically, the recombinant nucleic acid constructs of the present invention comprise a yeast origin of replication. Examples include, but are not limited to constructs containing autonomous replicating sequences, constructs containing 2 micron DNA including the autonomous replicating sequence and rep genes, constructs containing centromeres like the CEN6, CEN4, CEN11, CDN3 and autonomous replicating sequences, and other like sequences that are well known in the art. Exemplary nucleic acid constructs include constructs suitable for transforming yeast. These include, but are not limited to episomal constructs based on the yeast 2μ or CEN origin based plasmids like pYES2/CT, pYES3/CT, pESC/His, pESC/Ura, pESC/Trp, pES/Leu, p427TEF, pRS405, pRS406, pRS413, and other yeast-based constructs that are known in the art.

In some embodiments, the nucleic acid constructs of the present invention comprise elements to facilitate integration of the xylose reductase and/or xylitol dehydrogenase polynucleotide into a fungal host chromosome (I.e., the genome), by either homologous or non-homologous recombination and either site-directed or random mutagenesis. In some embodiments, the nucleic acid constructs comprise elements that facilitate homologous integration. In some embodiments, the xylose reductase and/or xylitol dehydrogenase polynucleotide is integrated at one or more site and is present in one or more copies. In some embodiments, the nucleic acid construct comprises the xylose reductase and/or xylitol dehydrogenase polynucleotide(s) and no promoter that is operatively linked to the xylose reductase and/or xylitol dehydrogenase polynucleotide. This type of construct typically comprises genetic elements to facilitate integration into the fungal host chromosome at a location that is downstream of a native promoter (i.e., in the host chromosome). In some embodiments, a second nucleic acid construct is employed which comprises a promoter and genetic elements to facilitate integration into the fungal host chromosome in a location upstream of the targeted integration site of the xylose reductase and/or xylitol dehydrogenase polynucleotide. In some embodiments, the nucleic acid construct comprises the xylose reductase and/or xylitol dehydrogenase polynucleotide operatively linked to a promoter or promoter and terminator sequences such that all are integrated into the host chromosome (genome).

Genetic elements that facilitate integration by homologous recombination are those having sequence homology to targeted integration sites in the fungal host chromosome (genome). Suitable sites that find use as targets for integration include, but are not limited to the TY1 loci, the RDN loci, the ura3 locus, the GPD locus, aldose reductase (GRE3) locus, etc. Those having ordinary skill in the art appreciate that additional sites for integration can be readily identified using methods known in the art, including but not limited to microarray analysis, metabolic flux analysis, comparative genome hybridization analysis, etc.

Genetic elements or techniques which facilitate integration by non-homologous recombination include, but are not limited to restriction enzyme-mediated integration (REMI) (See e.g., Manivasakam et al., Mol. Cell. Biol., 18(3):1736-1745 [1998], which is incorporated herein by reference), transposon-mediated integration, and other elements and methods that are well known in the art.

In some embodiments, the nucleic acid constructs of the present invention comprise at least one further recombinant polynucleotide that is capable of conferring a desired phenotype to a fungal host cell, particularly in the context of xylose fermentation. In some embodiments, the recombinant polynucleotide that is capable of conferring an improved phenotype to the fungal host cell is a non-coding polynucleotide such as a regulatory polynucleotide, a coding polynucleotide, or combination thereof.

Exemplary further desired phenotypes include, but are not limited to increased transport of xylose into the host cell, increased xylulose kinase activity, increased flux through the pentose phosphate pathway, decreased sensitivity to catabolite repression, increased tolerance to ethanol, increased tolerance to increased osmolarity, increased tolerance to organic acids, reduced production of by-products, and other similar properties related to increasing flux through the pentose phosphate and glycolysis pathways to produce a desired metabolic product/intermediate at higher levels as compared to the corresponding wild-type host cell. Typically, the desired metabolic product is an alcohol (e.g., ethanol).

In some embodiments, nucleic acid constructs comprising at least one further polynucleotide that is capable of conferring a desired phenotype to a fungal host cell comprise a polynucleotide encoding a protein known to impact the desired phenotype, wherein the polynucleotide is either native or heterologous to the fungal host cell. In some embodiments, this polynucleotide is operatively linked to its native promoter, or to a heterologous promoter (i.e., a promoter that is not associated with the polynucleotide in the corresponding native gene). In some embodiments, the at least one further polynucleotide is overexpressed. In some embodiments, the nucleic acid constructs comprise multiple copies of a least one polynucleotide. Suitable polynucleotides include, but are not limited to those that facilitate overexpression of proteins known to have an impact on the desired phenotype.

Exemplary recombinant polynucleotides that are capable of conferring a desired phenotype to a fungal host cell include recombinant polynucleotides (either wild-type or mutated forms) which encode a xylose or hexose transporter, a xylulose kinase (XKS), an enzyme from the pentose phosphate pathway (See e.g., FIG. 2A), a glycolytic enzyme (i.e., from the glycolytic metabolic pathway; See e.g., FIG. 2B), and an ethanologenic enzyme (See e.g., FIG. 2C), regulatory sequences that enhance expression of these sequences, and combinations thereof. Additional recombinant polynucleotides (either wild-type or mutated forms) that find use in the present invention include those that encode additional proteins involved in the pentose phosphate, glycolysis, and ethanologenic pathways (See e.g., FIGS. 2A-C).

Exemplary transporters include, but are not limited to GXF1, SUT1 and At6g59250 from *Candida intermedia, Pichia stipitis* and *Arabidopsis thaliana*, respectively (See e.g., Runquist et al., Biotechnol. Biofuels., 3:5 [2010], which is incorporated herein by reference), as well as HXT4, HXT5, HXT7, GAL2, AGT1, GXF2 (See e.g., Matsushika et al., Appl. Microbiol. Biotechnol., 84:37-53 [2009], which is incorporated herein by reference). In some embodiments, overexpression of native *S. cerevisiae* transporters is desirable, particularly HXT5 and HXT7.

Particularly suitable recombinant polynucleotides include those which encode: a xylulose kinase (XK); an enzyme from the pentose phosphate pathway (e.g., a ribulose-5-phosphate 3-epimerase (RPE1), a ribose-5-phosphate ketol-isomerase (RKI1), a transketolase (TKL1), a transaldolase (TAL1), etc.); a glycolytic enzyme (e.g., a hexokinase (HXK1/HXK2), a glyceraldehyde-3-phosphate dehydrogenase (GAPDH), a pyruvate kinase (PVK2), etc.); and an ethanologenic enzyme (e.g., a pyruvate decarboxylase, an alcohol dehydrogenase, etc.).

Exemplary regulatory polynucleotides include promoters, enhancer, terminator, and other regulatory elements that function to improve the expression of polynucleotides in a fungal host cell, particularly, a yeast host cell. These include, but are not limited to the regulatory elements described hereinabove.

The nucleic acid constructs described herein are useful for transforming fungal host cells to confer to these cells the property of xylose utilization.

Recombinant Fungal Host Cells

The present invention provides recombinant fungal host cells comprising at least one xylose reductase and/or xylitol dehydrogenase polynucleotide provided herein. More specifically, the recombinant fungal host cell comprises a polynucleotide sequence that encodes a polypeptide which is capable of catalyzing xylose to xylitol, wherein the polynucleotide is selected from: (a) a polynucleotide that encodes a polypeptide comprising an amino acid sequence that is at least about 70% identical to SEQ ID NO:2, wherein the polypeptide comprises at least one substitution set forth herein; and (b) a polynucleotide that hybridizes under stringent hybridization conditions to the complement of a polynucleotide encoding a polypeptide having the amino acid sequence of SEQ ID NO:2, wherein the polypeptide comprises at least one substitution set forth herein. In some other embodiments, the recombinant fungal host cell comprises a polynucleotide sequence that encodes a polypeptide which is capable of catalyzing xylitol to xylulose, wherein the polynucleotide is selected from: (a) a polynucleotide that encodes a polypeptide comprising an amino acid sequence that is at least about 70% identical to SEQ ID NO:6, wherein the polypeptide comprises at least one substitution as set forth herein; and (b) a polynucleotide that hybridizes under stringent hybridization conditions to the complement of a polynucleotide encoding a polypeptide having the amino acid sequence of SEQ ID NO:6, wherein the polypeptide comprises at least one substitution set forth herein. In some embodiments, the recombinant fungal host cell comprises polynucleotide sequences that encode a polypeptide which is capable of catalyzing xylose to xylitol and a polypeptide capable of catalyzing xylitol to xylulose-5-P, wherein the polynucleotides are selected from: (a) polynucleotides that encode polypeptides comprising amino acid sequences that are at least about 70% identical to SEQ ID NO:2 and/or 6, wherein each of the polypeptides comprise at least one substitution set forth herein; and (b) polynucleotides that hybridize under stringent hybridization conditions to the complement of polynucleotides encoding polypeptides having the amino acid sequences of SEQ ID NO:2 and/or 6, wherein each of the polypeptides comprise at least one substitution set forth herein.

In some embodiments, the recombinant fungal host cell further comprises at least one xylulokinase, including but not limited to the xylulokinase provided herein (SEQ ID NO:10), encoded by SEQ ID NO:9, and by codon-optimized sequences SEQ ID NOS:11 and 12.

In some embodiments, the recombinant fungal host cell comprises at least one xylose reductase, at least one xylitol dehydrogenase, and at least one xylulokinase. In some embodiments, the xylose reductase comprises SEQ ID NO:2, 41, 43, 45, and/or 47. In some embodiments, the xylitol dehydrogenase comprises SEQ ID NO:6 and/or 42. In some embodiments, the xylulokinase comprises SEQ ID NO:10.

In some embodiments, the present invention provides a recombinant fungal host cell comprising or transformed with a nucleic acid construct of the present invention. In some embodiments, the xylose reductase and/or xylitol dehydrogenase and/or xylulokinase polynucleotide is integrated into the host cell genome. Typically, the recombinant fungal host cell is a filamentous fungal or yeast host cell. More typically, the recombinant fungal host cell is a yeast host cell.

The present invention also provides methods for producing a recombinant fungal host cell, wherein the method comprises: (a) providing at least one nucleic acid construct of the present invention, wherein the nucleic acid construct comprises at least one xylose reductase and/or xylitol dehydrogenase and/or at least one xylulokinase polynucleotide provided herein; and (b) transforming a fungal host cell with the nucleic acid construct to produce a recombinant fungal host cell. In some additional embodiments, the recombinant fungal host cell is transformed using nucleic acid constructs comprising from about two to about fifty copies of at least one xylose reductase and/or xylitol dehydrogenase and/or xylulokinase. It is not intended that the present invention be limited to any particular copy number of xylose reductase and/or xylitol dehydrogenase genes and/or xylulokinase, as any suitable number of copies finds use in the present invention. In some embodiments, the nucleic acid constructs comprise any combination of wild-type and/or variant xylose reductase and/or xylitol dehydrogenase and/or xylulokinase. Furthermore, any suitable method for introducing multiple copies of either xylose reductase and/or xylitol dehydrogenase and/or xylulokinase find use in the present invention.

Introduction of the expression construct of the present invention into the host cell can be accomplished using any suitable method, including but not limited to calcium phosphate transfection, DEAE-dextran mediated transfection, electroporation, or any other suitable technique. Indeed, there are numerous methods known in the art and described in various standard reference texts. In some embodiments, the xylose reductase and/or xylitol dehydrogenase and/or xylulokinase polynucleotide sequence is integrated into the host cell genome.

Suitable fungal host cells include yeast and filamentous fungal host cells. In some embodiments, the fungal host cell is a yeast cell. Exemplary yeast host cells that are useful in the practice of the present invention include, but are not limited to *Candida*, *Hansenula*, *Saccharomyces*, *Schizosaccharomyces*, *Pichia*, *Kluyveromyces*, and *Yarrowia*. In some embodiments of the invention, the yeast cell is *Hansenula polymorpha*, *Saccharomyces cerevisiae*, *Saccharomyces carlsbergensis*, *Saccharomyces diastaticus*, *Saccharomyces norbensis*, *Saccharomyces kluyveri*, *Schizosaccharomyces pombe*, *Pichia pastoris*, *Pichia finlandica*, *Pichia trehalophila*, *Pichia kodamae*, *Pichia membranaefaciens*, *Pichia opuntiae*, *Pichia thermotolerans*, *Pichia salictaria*, *Pichia quercuum*, *Pichia pijperi*, *Pichia stipitis*, *Pichia methanolica*, *Pichia angusta*, *Kluyveromyces lactis*, *Candida albicans*, or *Yarrowia lipolytica*. In some embodiments, the yeast host cell is *Saccharomyces* species. In some additional embodiments, the yeast host cell is *Saccharomyces cerevisiae*.

Any suitable yeast strain finds use in the present invention, including but not limited to strains such as those commercially available from companies such as Lallemand (e.g., Superstart™, THERMOSACC®, etc.); RED STAR and ETHANOL RED® (Fermentis/Lesaffre); FALI (AB Mauri); (Baker's Best Yeast, Baker's Compressed Yeast, etc. (Fleishmann's Yeast); BIOFERM AFT, XP, CF, and XR (North American Bioproducts Corp.); TurboYeast (Gert Strand AB); FERMIOL® (DSM Specialties); BY4741 (e.g., ATCC 201388); Y108-1 (ATCC PTA.10567) and LNH-ST (See, US Pat. Publ. No. 2011/0159560); NRRL YB-1952 (ARS Culture Collection), as well as any additional suitable strains.

In some embodiments, the filamentous fungal host cell is a species of *Achlya*, *Acremonium*, *Aspergillus*, *Aureobasidium*, *Bjerkandera*, *Ceriporiopsis*, *Cephalosporium*, *Chrysosporium*, *Cochliobolus*, *Corynascus*, *Cryphonectria*, *Cryptococcus*, *Coprinus*, *Coriolus*, *Diplodia*, *Endothia*, *Fusarium*, *Gibberella*, *Gliocladium*, *Humicola*, *Hypocrea*, *Myceliophthora*, *Mucor*, *Neurospora*, *Penicillium*, *Podospora*, *Phlebia*, *Piromyces*, *Pyricularia*, *Rhizomucor*, *Rhizopus*, *Schizophyllum*, *Scytalidium*, *Sporotrichum*, *Talaromyces*, *Thermoascus*, *Thielavia*, *Trametes*, *Tolypocladium*, *Trichoderma*, *Verticillium*, *Volvariella*, or teleomorphs, or anamorphs, and synonyms or taxonomic equivalents thereof. However, it is not intended that the present invention be limited to any particular species of filamentous fungal host cell. Exemplary filamentous fungal host cells that find use in the present invention include, but are not limited to a filamentous fungal host cell of the *Trichoderma* species (e.g., *T. longibrachiatum*, *T. viride* [e.g., ATCC 32098 and 32086], *T. reesei* [NRRL 15709, ATTC 13631, 56764, 56765, 56466, 56767, and RL-P37 and derivatives thereof; See e.g., Sheir-Neiss et al., Appl. Microbiol. Biotechnol., 20:46-53 [1984], incorporated herein by reference), *T. koningii*, and *T. harzianum*), as well as *Hypocrea jecorina*. The term "*Trichoderma*" refers to any fungal strain that was previously classified as *Trichoderma* or is currently classified as *Trichoderma*.

In some embodiments of the present invention, the filamentous fungal host cell is an *Aspergillus* species (e.g., *A. awamori*, *A. funigatus*, *A. japonicas*, *A. nidulans*, *A. niger*. *A. aculeatus*, *A. foetidus*, *A. oryzae*, *A. sojae*, or *A. kawachi* (See e.g., Kelly and Hynes, EMBO J., 4:475479 [1985]; NRRL 3112, ATCC 11490, 22342, 44733, and 14331; Yelton et al., Proc. Natl. Acad. Sci. USA, 81, 1480-1474 [1984]; Tilburn et al., Gene 26, 205-221 [1982]; and Johnston et al., EMBO J., 4:1307-1311 [1985], all of which are incorporated herein by reference). In some embodiments of the invention, the filamentous fungal host cell is a *Fusarium* species (e.g., *F. bactridioides*, *F. cerealis*, *F. crookwellense*, *F. culmorum*, *F. graminaearum*, *F. graminum*, *F. oxysporum*, *F. rosium*, or *F. venenatum*). In some embodiments of the invention, the filamentous fungal host cell is of a *Neurospora* species (e.g., *N.* crassa*; See e.g., Case, et al., Proc. Natl. Acad. Sci. USA, 76:5259-5263 [1979]; U.S. Pat. No. 4,486,553; and Kinsey and Rambosek, Mol. Cell. Biol., 4:117-122 [1984], all of which are incorporated herein by reference). In some embodiments of the invention, the filamentous fungal host cell is of a *Humicola* species (e.g., *H. insolens. H. grisea*, or *H. lanuginose*). In some embodiments of the invention, the filamentous fungal host cell is a *Mucor* species (e.g., *M. miehei* or *M. circinelloides*). In some embodiments of the invention, the filamentous fungal host cell is a *Rhizopus* species (e.g., *R. oryzae* or *R. niveus*). In some embodiments of the invention, the filamentous fungal host cell is of a *Penicillum* species (e.g., *P. purpurogenum, P. chrysogenum*, or *P. verruculosum*). In some embodiments of the invention, the filamentous fungal host cell is a *Thielavia* species (e.g., *T. terrestris*). In some embodiments of the invention, the filamentous fungal host cell is a *Tolypocladium* species (e.g., *T. inflatum* or *T. geodes*). In some embodiments of the invention, the filamentous fungal host cell is a *Trametes* species (e.g., *T. villosa* or *T. versicolor*). In some embodiments of the invention, the filamentous fungal host cell is a *Chrysosporium* species, (e.g., *C. lucknowense, C. keratinophilum, C. tropicum, C. merdarium, C. inops, C. pannicola*, or *C. zonatum*).

Strains that find use in the present invention include those that are readily accessible to the public from a number of culture collection, including but not limited to the American Type Culture Collection (ATCC), Deutsche Sammlung von Mikroorganismen and Zellkutlturen GmbH (DSM), Centraalbureau Voor Schimmelcultures (CBS), and Agricultural Research Service Patent Culture Collection, Northern Regional Research Center (NRRL).

Recombinant fungal host cells of the present invention are capable of fermenting xylose when provided with a xylose based culture medium. Typically the recombinant fungal host cells described herein are capable of fermenting xylose at a faster rate compared to the corresponding wild-type fungal host cell. In some embodiments, the recombinant fungal host cells provided herein are capable of fermenting xylose at a faster rate compared to fungal host cells transformed with a nucleic acid construct comprising xylose reductase and/or xylitol dehydrogenase genes. In some other embodiments, the recombinant fungal host cells provided herein are capable of fermenting xylose at a faster rate compared to fungal host cells transformed with a nucleic acid construct comprising of xylose reductase, xylitol dehydrogenase and/or xylulose kinase genes. In some embodiments, the recombinant fungal host cells are capable of fermenting xylose at a rate of at least about 1 g/L/h and sometimes at a rate of at least about 2 g/L/h. Exemplary xylose-based culture media include culture media which have been formulated to contain xylose, as well as feedstock from cellulosic saccharification processes and/or feedstock from a hemicellulose pre-treatment process (i.e., a "hemicellulosic feedstock").

In some embodiments, the fungal host cell is a wild-type fungal cell, while in other embodiments, it is a mutated or otherwise altered or engineered form of a wild-type fungal cell. Typically, the fungal host cell (either wild-type or otherwise altered or engineered) comprises polynucleotides encoding a xylulokinase and one or more enzymes in the pentose phosphate, glycolytic, and/or ethanologenic pathways. In some embodiments, the fungal host cell comprises polynucleotides encoding a xylulokinase and all of the enzymes in the pentose phosphate, glycolytic, and ethanologenic pathways. In some embodiments, the fungal host cell comprises recombinant polynucleotides encoding enzymes that are heterologous to the fungal host cell (i.e., not native to the fungal host cell). In some additional embodiments, the fungal host cell is engineered to comprise other metabolic pathways that utilize products/intermediates from the pentose phosphate, glycolytic, and/or enthanologenic pathways to produce other desirable products. For example, in some embodiments, the fungal host cell is engineered to comprise a metabolic pathway for the biosynthesis of a fatty alcohol or fatty acid (See e.g., WO 2007/136762, which is incorporated herein by reference). In some embodiments, the fatty alcohol or fatty acid is a C8-C20 fatty acid or fatty alcohol. In some embodiments, the fungal host cell is altered or engineered to overexpress any one or more of the polynucleotides encoding the enzymes in one or more of these metabolic pathways.

In some embodiments, the recombinant fungal host cell of the present invention further comprises genetic modifications in addition to the xylose reductase and/or xylitol dehydrogenase polynucleotide. In some embodiments, in addition to having a xylose reductase and/or xylitol dehydrogenase polynucleotide described herein, the recombinant host cell comprises at least one different recombinant polynucleotide that is capable of conferring a further desired phenotype to the fungal host cell. In some embodiments, the present invention provides a recombinant fungal host cell comprising at least one *P. stipitis* xylose reductase and/or xylitol dehydrogenase polynucleotide or variant thereof as described herein, and at least one recombinant polynucleotide that encodes a polypeptide which differs from the *P. stipitis* xylose reductase and/or xylitol dehydrogenase and/or variant(s) thereof, wherein the recombinant polynucleotide imparts a desired phenotype to the fungal host cell. It is contemplated that in some embodiments, the recombinant polynucleotide that is capable of conferring a desired phenotype to the fungal host cell is introduced to the fungal host cell on the same nucleic construct as the xylose reductase and/or xylitol dehydrogenase polynucleotide, or on a separate nucleic acid construct. Nucleic acid constructs of the present invention comprising at least one xylose reductase and xylitol dehydrogenase polynucleotides and at least one further recombinant polynucleotide capable of conferring a desired phenotype to the fungal host cell are also provided by the present invention.

In some embodiments, the recombinant polynucleotide that is capable of conferring a desired phenotype to the fungal host cell is a non-coding polynucleotide (e.g., a regulatory polynucleotide, a coding polynucleotide, or a combination thereof). As described above, exemplary further desired phenotypes include, but are not limited to increased transport of xylose into the host cell, increased xylulose kinase activity, increased flux through the pentose phosphate pathway, decreased sensitivity to catabolite repression, increased tolerance to ethanol, increased tolerance to increased osmolarity, increased tolerance to organic acids, reduced production of by-products, and other like properties related to increasing flux through the pentose phosphate, glycolysis, and/or ethanologenic pathways to produce the desired metabolic product/intermediate at higher levels as compared to the corresponding wild-type host cell. In some embodiments, the desired metabolic product is an alcohol (e.g., ethanol).

In some embodiments, recombinant fungal host cells comprising at least one further polynucleotide capable of conferring a desired phenotype to the fungal host cell comprise at least one polynucleotide encoding a protein known to impact the desired phenotype, wherein the polynucleotide is either native or heterologous to the fungal host cell. In some embodiments, the polynucleotide(s) are operatively linked to its native promoter, while in other embodiments, the polynucleotide is operatively linked to a heterologous promoter (i.e., one not associated with the polynucleotide in the corresponding native gene). In some embodiments, the polynucleotide is overexpressed. In some embodiments, the recombinant fungal host cell comprises multiple copies of the polynucleotide. Suitable polynucleotides include, but are not limited to those that facilitate overexpression of proteins known to have an impact on the desired phenotype. Therefore, in some embodiments, the fungal host cell is altered or engineered to overexpress one or more polynucleotides.

In some embodiments, recombinant polynucleotides that are capable of imparting a desired phenotype to a fungal host cell include, but are not limited to recombinant polynucleotides which encode a xylose or hexose transporter, a xylulose kinase (XKS), an enzyme from the pentose phosphate pathway (See e.g., FIG. 2A), a glycolytic enzyme (i.e., from the metabolic pathway of glycolysis; See e.g., FIG. 2B), and an ethanologenic enzyme (See e.g., FIG. 2C), the regulatory sequences associated with these sequences, and any combination thereof.

Exemplary transporters that find use in the present invention include, but are not limited to GXF1, SUT1 and At6g59250 from *Candida intermedia, Pichia stipitis*, and *Arabidopsis thaliana*, respectively (See e.g., Runquist et al., 84:37-53 [2010], incorporated herein by reference), HXT4, HXT5, HXT7, GAL2, AGT1, and GXF2, (See e.g., Matsushika et al., Appl. Microbiol. Biotechnol., 84:37-53 [2009]). In some embodiments, overexpression of native *S. cerevisiae* transporters is desirable, particularly HXT5 and HXT7.

Particularly suitable recombinant polynucleotides include, but are not limited to those that encode: a xylulose kinase (XK); an enzyme from the pentose phosphate pathway (e.g., a ribulose-5-phosphate 3-epimerase (RPE1), a ribose-5-phosphate ketol-isomerase (RKI1), a transketolase (TKL1), a transaldolase (TAL1), etc.); a glycolytic enzyme (e.g., a hexokinase (HXK1/HXK2), a glyceraldehyde-3-phosphate dehydrogenase (GAPDH), a pyruvate kinase (PVK2), etc.; and an ethanologenic enzyme (e.g., a pyruvate decarboxylase, an alcohol dehydrogenase, etc.).

Exemplary regulatory polynucleotides include promoters, enhancer, terminator, and other regulatory elements that function to improve the expression of polynucleotides in a fungal host cell, particularly, a yeast host cell, as described above.

In some embodiments, recombinant host cells of the present invention comprise one or more native genes deleted from its genome. In some embodiments, the deletion(s) cause removal or diminishment of a biological activity that is otherwise exhibited by the fungal host cell. In some embodiments, the cumulative effect of the deletion(s) also leads to an improvement in a phenotype of the fungal host cell. Any suitable method for deleting gene finds use in the present invention. There are numerous methods well known in the art.

For example, in some embodiments, recombinant host cells of the present invention have certain native genes deleted from the host genome in order to improve the utilization of pentose sugars (e.g., xylose), increase transport of xylose into the host cell, increase xylulose kinase activity, increase flux through the pentose phosphate pathway, decrease sensitivity to catabolite repression, increase tolerance to ethanol/acetate, increase tolerance to increased osmolarity, increase tolerance to organic acids (low pH), reduce production of by-products, and other like properties related to increasing flux through the relevant pathways to produce ethanol and other desired metabolic products at higher levels, where comparison is made with respect to the corresponding host cell without the deletion(s). Genes targeted for deletion include, but are not limited to genes encoding enzymes in the pentose phosphate pathway, a glycolytic enzyme, and/or an ethanologenic enzyme.

In some embodiments, other genes are targeted for deletion, including but not limited to those encoding aldose reductase (GRE3) (See e.g., Matsushika et al., Appl. Microbiol. Biotechnol., 84:37-53 [2009]), sorbitol dehydrogenases (SOR1/SOR2), a glutamate dehydrogenase (GDH1), a 6-phosphogluconate dehydrogenase (GND), a glucose-5-phosphate dehydrogenase (ZWF1), and any enzyme for which its deletion is known in the art to improve the utilization of a pentose sugar, decrease by-product formation, and/or increase the ethanol yield of a fungal host cell. The genes encoding these enzymes in many fungi are known in the art. Those having ordinary skill in the art appreciate that additional genes encoding these enzymes can be readily identified by microarray analysis (See e.g., Sedlak et al., Yeast 21:671-684 [2004]), metabolic flux analysis (See e.g Sonderegger et al., Appl. Environ. Microbiol., 70(4):2307-2317 [2004]), in silico modeling (See e.g Hjersted et al., Biotechnol. Bioengineer. 97(5):1190-1204 [2007]), chemogenomics (See e.g Teixeira et al., Appl. Environ. Microbiol., 75(18):5761-5772 [2009]), and other well known methods.

In some embodiments, the host cells employed in the practice of the present invention are mutagenized and/or evolved to exhibit further desired phenotypes, for example, further improvement in the utilization of pentose sugars (e.g., xylose, arabinose, etc.), increased transport of xylose into the host cell, increased xylulose kinase activity, increased flux through the pentose phosphate pathway, decreased sensitivity to catabolite repression, increased tolerance to ethanol/acetate, increased tolerance to increased osmolarity, increased tolerance to organic acids (low pH), reduced production of by-products, and other like properties related to increasing flux through the pentose phosphate and glycolysis pathways to produce a desired metabolic product/intermediate at higher levels. In some embodiments, the desired metabolic product is an alcohol (e.g., ethanol). In some embodiments, the host cells are mutagenized and/or evolved using known methods either prior to or after transformation with the xylose reductase and/or xylitol dehydrogenase polynucleotide. These methods include, but are not limited to classical mutagenesis, whole genome shuffling, evolutionary engineering methods, which employ screening and/or selection methods, or any combination of such well known methods.

Classical mutagenesis methods include, but are not limited to treatment of the host cell with a mutagen such as a chemical mutagen or irradiation exposure (e.g., ultraviolet or gamma-irradiation). Whole genome shuffling methods involving, for example, recombination of genomic DNA between native genomic DNA sequences and/or variants thereof, can be facilitated by sexual mating, protoplast fusion methods and other methods well known in the art (See e.g., WO 98/31837 and WO 2000/04190, incorporated herein by reference). These methods are coupled with screening and/or selection methods to identify altered fungal host cells that exhibit the desired phenotype. For example, such methods find use in altering or engineering a fungal host cell to overexpress one or more desired polynucleotides.

Mutagenesis may be performed in accordance with any of the techniques known in the art, including random and site-specific mutagenesis. Directed evolution can be performed with any of the techniques known in the art to screen for improved promoter variants including shuffling. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03, 344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related US and non-US counterparts; Ling et al., Anal. Biochem., 254(2):157-78 [1997]; Dale et al., Meth. Mol. Biol., 57:369-74 [1996]; Smith, Ann Rev. Genet., 19:423-462 [1985]; Botstein et al., Science, 229: 1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

Evolutionary engineering can be done by prolonged cultivation and selection of strains under desired conditions through chemostat, turbidostat or batch cultures. Evolutionary engineering methods can be practiced under either aerobic or anaerobic conditions. Selection strategies can be optimized by varying culture conditions, for example, carbon source, nitrogen source, aeration, pH and temperature. Methods for evolutionary engineering are well known in the art (See e.g., Wisselink et al., Appl. Environ. Microbiol., 75(4): 907-914 [2009]; Kuyper et al., FEMS Yeast Res., 5:399-409 [2005]; and Sauer, Adv. Biochem. Engineer. Biotechnol., 73:129-169 [2001], all of which are incorporated herein by reference).

Therefore, in some embodiments, the recombinant fungal host cell comprising a xylose reductase and/or xylitol dehydrogenase polynucleotide exhibits an improved phenotype relative to the corresponding fungal host cell without the xylose reductase and/or xylitol dehydrogenase polynucleotide.

In some embodiments, whole genome shuffling and evolutionary engineering methods result in increased copy number of xylose reductase and/or xylitol dehydrogenase and/or xylulokinase from two to fifty copies. It is not intended that the present invention be limited to any particular copy number of xylose reductase and/or xylitol dehydrogenase genes and/or xylulokinase, as any suitable number of copies finds use in the present invention. In some embodiments, the nucleic acid constructs comprise any combination of wild-type and/or variant xylose reductase and/or xylitol dehydrogenase and/or xylulokinase. Furthermore, any suitable method of increasing copies of either xylose reductase and/or xylitol dehydrogenase and/or xylulokinase finds use in the present invention.

In some embodiments, the improved phenotype comprises further improvement in the utilization of pentose sugars (e.g., xylose, arabinose, etc.), increased transport of xylose into the host cell, increased xylulose kinase activity, increased flux through the pentose phosphate pathway, decreased sensitivity to catabolite repression, increased tolerance to ethanol/acetate, increased tolerance to increased osmolarity, increased tolerance to organic acids (low pH), and reduced production of by products, or other properties.

Fermentation

The present invention provides processes for producing fermentation products, wherein the method comprises: (a) providing the recombinant fungal cell of the present invention; (b) providing a fermentation medium comprising xylose; (c) contacting the fermentation medium with the recombinant fungal cell under conditions suitable for generating the fermentation product; and optionally (d) recovering the fermentation product. In some embodiments, the fermentation product is an alcohol (e.g., ethanol, butanol, etc.), a fatty alcohol (e.g., a C8-C20 fatty alcohol), a fatty acid (e.g., a C8-C20 fatty acid), lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., cephalosporin). However, it is contemplated that other fermentation products will be produced using the methods of the present invention.

In some embodiments, the fermentation medium is feedstock from a cellulosic saccharification process and/or feedstock from a hemicellulose pre-treatment process. Such feedstocks include, but are not limited to carbohydrates (e.g., lignocellulose, xylans, cellulose, starch, etc.), other sugars (e.g., glucose, xylose, arabinose, etc.), and other compositions. Compositions of fermentation media suitable for the growth of yeast and filamentous fungi are well known in the art and there are various reference texts that provide recipes for these media.

Fermentation conditions suitable for generating desired fermentation products are well known in the art and any suitable method finds use in the present invention. In some embodiments, the fermentation process is carried out under aerobic or microaerobic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generated NAD+. In some embodiments of the present invention, when the fermentation process is carried out under anaerobic conditions, pyruvate may be reduced to a fermentation product such as ethanol, butanol, lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., a cephalosporin).

The fermentation process is typically run at a temperature that is optimal for the recombinant fungal cell. For example, in some embodiments, the fermentation process is performed at a temperature in the range of from about 25° C. to about 42° C. Typically the process is carried out a temperature that is less than about 38° C., less than about 35° C., less than about 33° C., or less than about 38° C., but at least about 20° C., 22° C., or 25° C.

In some embodiments, recombinant host cells of the present invention are grown under batch or continuous fermentation conditions. Classical batch fermentation is a closed system, wherein the composition of the medium is set at the beginning of the fermentation and is not subject to artificial alterations during the fermentation. A variation of the batch system is a fed-batch fermentation, which also finds use in the present invention. In this variation, the substrate is added in increments as the fermentation progresses. Fed-batch systems are useful when catabolite repression is likely to inhibit the metabolism of the cells and/or where it is desirable to have limited amounts of substrate in the medium. Batch and fed-batch fermentations are common and well known in the art. Continuous fermentation is an open system where a defined fermentation generally maintains the culture at a constant high density where cells are primarily in log phase growth. Continuous fermentation systems strive to maintain steady state growth conditions. Methods for modulating nutrients and growth factors for continuous fermentation processes, as well as techniques for modulating nutrients and growth factors for continuous fermentation processes as well as techniques for maximizing the rate of product formation are well known in the art of industrial microbiology.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); HPLC (high pressure liquid chromatography); MES (2-N-morpholino ethanesulfonic acid); FIOPC (fold improvements over positive control); YPD (10 g/L yeast extract, 20 g/L peptone, and 20 g/L dextrose); SOE-PCR (splicing by overlapping extension PCR); ARS (ARS Culture Collection or NRRL Culture Collection, Peoria, Ill.); Axygen (Axygen, Inc., Union City, Calif.); Lallemand (Lallemand Ethanol Technology, Milwaukee, Wis.); Dual Biosystems (Dual Biosystems AG, Schlieven, Switzerland); Megazyme (Megazyme International Ireland, Ltd., Wicklow, Ireland); Dasgip (Dasgip Biotools, LLC, Shrewsbury, Mass.); Difco (Difco Laboratories, BD Diagnostic Systems, Detroit, Mich.); PCRdiagnostics (PCRdiagnostics, by E coli SRO, Slovak Republic); Agilent (Agilent Technologies, Inc., Santa Clara, Calif.); and Bio-Rad (Bio-Rad Laboratories, Hercules, Calif.).

The following sequences find use in the present invention. SEQ ID NO:2 provides the polypeptide sequence of P. stipitis xylose reductase ("XR.1"), while SEQ ID NO:1 provides the native polynucleotide sequence, SEQ ID NO:3 provides one codon optimized DNA sequence ("XR.2"), and SEQ ID NO:4 provides an alternative codon optimized DNA sequence ("XR.3"). SEQ ID NO:6 provides the polypeptide sequence of P. stipitis xylitol dehydrogenase ("XD.1"), while SEQ ID NO:5 provides the native polynucleotide sequence, SEQ ID NO:7 provides one codon optimized DNA sequence ("XD.2"), and SEQ ID NO:8 provides an alternative codon optimized DNA sequence ("XD.3"). SEQ ID NO:10 provides the polypeptide sequence of S. cerevisiae xylulokinase ("XK.1"), SEQ ID NO:9 provides the native polynucleotide sequence, SEQ ID NO:11 provides one codon optimized DNA sequence ("XK.2"), and SEQ ID NO:12 provides an alternative codon optimized DNA sequence ("XK.3").

(SEQ ID NO: 2)
MPSIKLNSGYDMPAVGFGCWKVDVDTCSEQIYRAIKTGYRLFDGAEDYANEKLVGAGVKKAID

EGIVKREDLFLTSKLWNNYHHPDNVEKALNRTLSDLQVDYVDLFLIHFPVTFKFVPLEEKYPPGF

YCGKGDNFDYEDVPILETWKALEKLVKAGKIRSIGVSNFPGALLLDLLRGATIKPSVLQVEHHPY

LQQPRLIEFAQSRGIAVTAYSSFGPQSFVELNQGRALNTSPLFENETIKAIAAKHGKSPAQVLLRW

SSQRGIAIIPKSNTVPRLLENKDVNSFDLDEQDFADIAKLDINLRFNDPWDWDKIPIFV (SEQ ID NO: 1)
ATGCCTTCTATTAAGTTGAACTCTGGTTACGACATGCCAGCCGTCGGTTTCGGCTGTTGGAAA

GTCGACGTCGACACCTGTTCTGAACAGATCTACCGTGCTATCAAGACCGGTTACAGATTGTT

CGACGGTGCCGAAGATTACGCCAACGAAAAGTTAGTTGGTGCCGGTGTCAAGAAGGCCATT

GACGAAGGTATCGTCAAGCGTGAAGACTTGTTCCTTACCTCCAAGTTGTGGAACAACTACCA

CCACCCAGACAACGTCGAAAAGGCCTTGAACAGAACCCTTTCTGACTTGCAAGTTGACTACG

TTGACTTGTTCTTGATCCACTTCCCAGTCACCTTCAAGTTCGTTCCATTAGAAGAAAAGTACC

CACCAGGATTCTACTGTGGTAAGGGTGACAACTTCGACTACGAAGATGTTCCAATTTTAGAG

ACCTGGAAGGCTCTTGAAAAGTTGGTCAAGGCCGGTAAGATCAGATCTATCGGTGTTTCTAA

CTTCCCAGGTGCTTTGCTCTTGGACTTGTTGAGAGGTGCTACCATCAAGCCATCTGTCTTGCA

AGTTGAACACCACCCATACTTGCAACAACCAAGATTGATCGAATTCGCTCAATCCCGTGGTA

TTGCTGTCACCGCTTACTCTTCGTTCGGTCCTCAATCTTTCGTTGAATTGAACCAAGGTAGAG

CTTTGAACACTTCTCCATTGTTCGAGAACGAAACTATCAAGGCTATCGCTGCTAAGCACGGT

AAGTCTCCAGCTCAAGTCTTGTTGAGATGGTCTTCCCAAAGAGGCATTGCCATCATTCCAAA

```
GTCCAACACTGTCCCAAGATTGTTGGAAAACAAGGACGTCAACAGCTTCGACTTGGACGAA

CAAGATTTCGCTGACATTGCCAAGTTGGACATCAACTTGAGATTCAACGACCCATGGGACTG

GGACAAGATTCCTATCTTCGTCTAATAA
```

(SEQ ID NO: 3)
```
ATGCCCTCCATAAAGCTAAACTCTGGTTATGATATGCCTGCCGTTGGATTCGGTTGTTGGAA

AGTAGATGTTGATACCTGCTCAGAACAGATTTATAGGGCTATTAAAACAGGTTACAGGTTGT

TCGACGGTGCCGAGGACTACGCGAATGAGAAGTTAGTTGGAGCTGGTGTTAAGAAGGCCAT

CGACGAGGGCATTGTTAAGAGGGAGGACCTGTTCTTAACGTCTAAACTGTGGAATAACTATC

ACCACCCAGACAATGTTGAAAAAGCCCTGAATAGAACTTTGAGTGATTTGCAGGTGGATTAC

GTTGACTTGTTTCTAATCCATTTCCCCGTTACTTTCAAGTTCGTCCCTTTAGAGGAGAAGTAT

CCACCAGGTTTCTATTGTGGTAAGGGCGACAACTTCGACTATGAAGATGTTCCTATTCTGGA

GACCTGGAAGGCTCTGGAGAAACTGGTCAAGGCAGGCAAAATAAGGTCCATAGGCGTCTCT

AACTTCCCAGGAGCACTACTGCTTGACTTGTTGAGGGGAGCTACCATCAAACCTTCAGTCTT

GCAAGTTGAACACCACCCCTATTTGCAACAACCCAGGCTGATAGAGTTTGCTCAATCCAGAG

GTATAGCTGTTACTGCATACTCTTCCTTTGGACCTCAATCCTTCGTCGAACTTAACCAAGGTA

GAGCGTTGAATACTTCCCCCTTGTTCGAGAATGAAACTATCAAGGCTATTGCGGCTAAGCAC

GGTAAGTCACCAGCTCAAGTGTTACTTAGATGGTCTTCCCAAAGGGGTATCGCAATCATTCC

AAAGTCTAACACTGTTCCCAGATTGTTGGAGAATAAAGATGTTAATTCTTTCGATTTGGACG

AACAAGACTTTGCAGACATAGCCAAACTAGATATTAATCTGAGATTCAATGATCCCTGGGAT

TGGGACAAGATACCAATCTTCGTTTAATAA
```

(SEQ ID NO: 4)
```
ATGCCATCTATTAAGTTGAACTCTGGTTACGACATGCCAGCTGTCGGTTTCGGTTGTAAGGTT

GACGTTGACACCTGTTCTGAACAAATTTACAGAGCTATTAAGACCGGTTACAGATTGTTCGA

CGGTGCTGAAGACTACGCTAACGAAAAGTTGGTTGGTGCTGGTGTCAAGAAGGCTATTGAC

GAAGGTATTGTCAAGAGAGAAGACTTGTTCTTGACCTCTAAGTTGAACAACTACCACCACCC

AGACAACGTCGAAAAGGCTTTGAACAGAACCTTGTCTGACTTGCAAGTTGACTACGTTGACT

TGTTCTTGATTCACTTCCCAGTCACCTTCAAGTTCGTCCCATTGGAAGAAAAGTACCCACCAG

GTTTCTACTGTGGTAAGGGTGACAACTTCGACTACGAAGACGTTCCAATTTTGGAAACCAAG

GCTTTGGAAAAGTTGGTTAAGGCTGGTAAGATTAGGTCTATTGGTGTTTCTAACTTCCCAGGT

GCTTTGTTGTTGGACTTGTTGAGAGGTGCTACCATTAAGCCATCTGTTTTGCAAGTTGAACAC

CACCCATACTTGCAACAACCAAGATTGATTGAGTTCGCTCAATCTAGGGGTATTGCTGTCAC

CGCTTACTCTTCTTTCGGTCCACAATCTTTCGTCGAATTGAACCAAGGTAGAGCTTTGAACAC

CTCTCCATTGTTCGAAAACGAAACCATTAAGGCTATTGCTGCTAAGCACGGTAAGTCTCCAG

CTCAAGTCTTGTTGAGGTCTTCTCAAAGAGGTATTGCTATTATTCCAAAGTCTAACACCGTCC

CAAGATTGTTGGAAAACAAGGACGTTAACTCTTTCGACTTGGACGAACAAGACTTCGCTGAC

ATTGCTAAGTTGGACATTAACTTGAGATTCAACGACCCAGACGACAAGATTCCAATTTTCGT

TTAATAA
```

(SEQ ID NO: 6)
```
MTANPSLVLNKIDDISFETYDAPEISEPTDVLVQVKKTGICGSDIHFYAHGRIGNFVLTKPMVLGH

ESAGTVVQVGKGVTSLKVGDNVAIEPGIPSRFSDEYKSGHYNLCPHMAFAATPNSKEGEPNPPGT

LCKYFKSPEDFLVKLPDHVSLELGALVEPLSVGVHASKLGSVAFGDYVAVFGAGPVGLLAAAV

AKTFGAKGVIVVDIFDNKLKMAKDIGAATHTFNSKTGGSEELIKAFGGNVPNVVLECTGAEPCIK
```

LGVDAIAPGGRFVQVGNAAGPVSFPITVFAMKELTLFGSFRYGFNDYKTAVGIFDTNYQNGREN

APIDFEQLITHRYKFKDAIEAYDLVRAGKGAVKCLIDGPE (SEQ ID NO: 5)
ATGACTGCTAACCCTTCCTTGGTGTTGAACAAGATCGACGACATTTCGTTCGAAACTTACGA

TGCCCCAGAAATCTCTGAACCTACCGATGTCCTCGTCCAGGTCAAGAAAACCGGTATCTGTG

GTTCCGACATCCACTTCTACGCCCATGGTAGAATCGGTAACTTCGTTTTGACCAAGCCAATG

GTCTTGGGTCACGAATCCGCCGGTACTGTTGTCCAGGTTGGTAAGGGTGTCACCTCTCTTAA

GGTTGGTGACAACGTCGCTATCGAACCAGGTATTCCATCCAGATTCTCCGACGAATACAAGA

GCGGTCACTACAACTTGTGTCCTCACATGGCCTTCGCCGCTACTCCTAACTCCAAGGAAGGC

GAACCAAACCCACCAGGTACCTTATGTAAGTACTTCAAGTCGCCAGAAGACTTCTTGGTCAA

GTTGCCAGACCACGTCAGCTTGGAACTCGGTGCTCTTGTTGAGCCATTGTCTGTTGGTGTCCA

CGCCTCTAAGTTGGGTTCCGTTGCTTTCGGCGACTACGTTGCCGTCTTTGGTGCTGGTCCTGT

TGGTCTTTTGGCTGCTGCTGTCGCCAAGACCTTCGGTGCTAAGGGTGTCATCGTCGTTGACAT

TTTCGACAACAAGTTGAAGATGGCCAAGGACATTGGTGCTGCTACTCACACCTTCAACTCCA

AGACCGGTGGTTCTGAAGAATTGATCAAGGCTTTCGGTGGTAACGTGCCAAACGTCGTTTTG

GAATGTACTGGTGCTGAACCTTGTATCAAGTTGGGTGTTGACGCCATTGCCCCAGGTGGTCG

TTTCGTTCAAGTCGGTAACGCTGCTGGTCCAGTCAGCTTCCCAATCACCGTTTTCGCCATGAA

GGAATTGACTTTGTTCGGTTCTTTCAGATACGGATTCAACGACTACAAGACTGCTGTTGGAA

TCTTTGACACTAACTACCAAAACGGTAGAGAAAATGCTCCAATTGACTTTGAACAATTGATC

ACCCACAGATACAAGTTCAAGGACGCTATTGAAGCCTACGACTTGGTCAGAGCCGGTAAGG

GTGCTGTCAAGTGTCTCATTGACGGCCCTGAGTAATAA (SEQ ID NO: 7)
ATGACCGCTAATCCCTCTCTTGTTTTGAATAAGATTGACGACATTTCTTTTGAAACTTACGAT

GCTCCCGAAATTAGCGAACCCACAGACGTTTTAGTTCAAGTTAAAAAAACTGGTATCTGCGG

TTCTGACATCCACTTCTACGCTCATGGAAGGATCGGCAACTTCGTCTTAACAAAGCCAATGG

TTCTGGGTCATGAAAGCGCGGGTACTGTTGTTCAAGTCGGTAAAGGTGTTACTTCACTGAAG

GTTGGTGATAACGTCGCAATCGAGCCCGGTATTCCATCTAGGTTCAGTGATGAGTACAAATC

TGGTCACTACAACCTGTGTCCACACATGGCATTTGCTGCTACTCCCAATTCTAAAGAGGGTG

AACCAAACCCACCAGGAACTCTATGTAAGTACTTCAAATCTCCAGAAGACTTCCTGGTTAAG

TTACCCGATCATGTTTCTTTGGAGTTGGGTGCTTTGGTCGAGCCACTATCTGTTGGGGTCCAT

GCTAGTAAATTAGGCTCCGTTGCATTTGGCGATTACGTTGCTGTTTTTGGTGCTGGTCCAGTA

GGATTACTGGCTGCCGCTGTCGCTAAGACATTTGGTGCCAAGGGTGTGATTGTCGTTGATAT

ATTTGACAACAAGCTGAAGATGGCCAAAGACATAGGTGCCGCTACACATACCTTCAACTCCA

AGACGGGAGGTAGTGAAGAATTGATCAAAGCCTTCGGTGGTAATGTACCAAATGTTGTCTTG

GAATGTACTGGGGCTGAACCATGTATTAAGCTAGGTGTTGATGCCATCGCACCAGGTGGTAG

ATTCGTGCAAGTTGGTAATGCTGCTGGTCCCGTGTCCTTTCCCATAACAGTGTTCGCTATGAA

AGAACTTACTTTGTTTGGTTCATTTCGTTATGGTTTCAACGACTATAAGACAGCCGTGGGTAT

CTTTGATACTAACTACCAGAACGGTAGAGAGAATGCTCCCATTGACTTTGAACAGCTTATCA

CGCACAGATACAAATTCAAAGACGCCATTGAAGCCTACGACCTAGTAAGAGCAGGTAAAGG

GGCTGTCAAGTGTTTGATTGATGGTCCAGAATAATAA (SEQ ID NO: 8)
ATGACCGCTAACCCATCTTTGGTCTTGAACAAGATTGACGACATTTCTTTCGAAACCTACGA

-continued
```
CGCTCCAGAAATTTCTGAACCAACCGACGTTTTGGTTCAAGTCAAGAAGACCGGTATTTGTG

GTTCTGACATTCACTTCTACGCTCACGGTAGAATTGGTAACTTCGTCTTGACCAAGCCAATGG

TCTTGGGTCACGAATCTGCTGGTACCGTTGTTCAAGTCGGTAAGGGTGTCACCTCTTTGAAG

GTCGGTGACAACGTCGCTATTGAACCAGGTATTCCAAGTAGATTCTCTGACGAATACAAGTC

TGGTCACTACAACTTGTGTCCACACATGGCTTTCGCTGCTACCCCAAACTCTAAGGAAGGTG

AACCAAACCCACCAGGTACCTTGTGTAAGTACTTCAAGTCTCCAGAAGACTTCTTGGTTAAG

TTGCCAGACCACGTTTCTTTGGAATTGGGTGCTTTGGTTGAACCATTGTCTGTTGGTGTTCAC

GCTTCTAAGTTGGGTTCTGTTGCTTTCGGTGACTACGTTGCTGTTTTCGGTGCTGGTCCAGTT

GGTTTGTTGGCTGCTGCTGTTGCTAAGACCTTCGGTGCTAAGGGTGTCATTGTCGTTGACATT

TTCGACAACAAGTTGAAGATGGCTAAGGACATTGGTGCTGCTACCCACACCTTCAACTCTAA

GACCGGTGGTTCTGAAGAATTGATTAAGGCTTTCGGTGGTAACGTCCCAAACGTCGTCTTGG

AATGTACCGGTGCTGAACCATGTATTAAGTTGGGTGTTGACGCTATTGCTCCAGGTGGTAGA

TTCGTCCAAGTTGGTAACGCTGCTGGTCCAGTTTCTTTCCCAATTACCGTTTTCGCTATGAAG

GAATTGACCTTGTTCGGTTCTTTCAGATACGGTTTCAACGACTACAAGACCGCTGTTGGTATT

TTCGACACCAACTACCAAAACGGTAGAGAAAACGCTCCAATTGACTTCGAACAATTGATTAC

CCACAGATACAAGTTCAAGGACGCTATTGAAGCTTACGACTTGGTTAGAGCTGGTAAGGGTG

CTGTTAAGTGTTTGATTGACGGTCCAGAATAATAA (SEQ ID NO: 9)
ATGTTGTGTTCAGTAATTCAGAGACAGACAAGAGAGGTTTCCAACACAATGTCTTTAGACTC

ATACTATCTTGGGTTTGATCTTTCGACCCAACAACTGAAATGTCTCGCCATTAACCAGGACCT

AAAAATTGTCCATTCAGAAACAGTGGAATTTGAAAAGGATCTTCCGCATTATCACACAAAGA

AGGGTGTCTATATACACGGCGACACTATCGAATGTCCCGTAGCCATGTGGTTAGAGGCTCTA

GATCTGGTTCTCTCGAAATATCGCGAGGCTAAATTTCCATTGAACAAAGTTATGGCCGTCTC

AGGGTCCTGCCAGCAGCACGGGTCTGTCTACTGGTCCTCCCAAGCCGAATCTCTGTTAGAGC

AATTGAATAAGAAACCGGAAAAAGATTTATTGCACTACGTGAGCTCTGTAGCATTTGCAAGG

CAAACCGCCCCCAATTGGCAAGACCACAGTACTGCAAAGCAATGTCAAGAGTTTGAAGAGT

GCATAGGTGGGCCTGAAAAAATGGCTCAATTAACAGGGTCCAGAGCCCATTTTAGATTTACT

GGTCCTCAAATTCTGAAAATTGCACAATTAGAACCAGAAGCTTACGAAAAAACAAAGACCA

TTTCTTTAGTGTCTAATTTTTTGACTTCTATCTTAGTGGGCCATCTTGTTGAATTAGAGGAGGC

AGATGCCTGTGGTATGAACCTTTATGATATACGTGAAAGAAAATTCAGTGATGAGCTACTAC

ATCTAATTGATAGTTCTTCTAAGGATAAAACTATCAGACAAAAATTAATGAGAGCACCCATG

AAAAATTTGATAGCGGGTACCATCTGTAAATATTTTATTGAGAAGTACGGTTTCAATACAAA

CTGCAAGGTCTCTCCCATGACTGGGGATAATTTAGCCACTATATGTTCTTTACCCCTGCGGAA

GAATGACGTTCTCGTTTCCCTAGGAACAAGTACTACAGTTCTTCTGGTCACCGATAAGTATC

ACCCCTCTCCGAACTATCATCTTTTCATTCATCCAACTCTGCCAAACCATTATATGGGTATGA

TTTGTTATTGTAATGGTTCTTTGGCAAGGGAGAGGATAAGAGACGAGTTAAACAAAGAACG

GGAAAATAATTATGAGAAGACTAACGATTGGACTCTTTTTAATCAAGCTGTGCTAGATGACT

CAGAAAGTAGTGAAAATGAATTAGGTGTATATTTTCCTCTGGGGGAGATCGTTCCTAGCGTA

AAAGCCATAAACAAAAGGGTTATCTTCAATCCAAAAACGGGTATGATTGAAAGAGAGGTGG

CCAAGTTCAAAGACAAGAGGCACGATGCCAAAAATATTGTAGAATCACAGGCTTTAAGTTG

CAGGGTAAGAATATCTCCCCTGCTTTCGGATTCAAACGCAAGCTCACAACAGAGACTGAACG
```

```
AAGATACAATCGTGAAGTTTGATTACGATGAATCTCCGCTGCGGGACTACCTAAATAAAAGG

CCAGAAAGGACTTTTTTTGTAGGTGGGGCTTCTAAAAACGATGCTATTGTGAAGAAGTTTGC

TCAAGTCATTGGTGCTACAAAGGGTAATTTTAGGCTAGAAACACCAAACTCATGTGCCCTTG

GTGGTTGTTATAAGGCCATGTGGTCATTGTTATATGACTCTAATAAAATTGCAGTTCCTTTTG

ATAAATTTCTGAATGACAATTTTCCATGGCATGTAATGGAAAGCATATCCGATGTGGATAAT

GAAAATTGGGATCGCTATAATTCCAAGATTGTCCCCTTAAGCGAACTGGAAAAGACTCTCAT

CTAA
```

(SEQ ID NO: 10)
```
MLCSVIQRQTREVSNTMSLDSYYLGFDLSTQQLKCLAINQDLKIVHSETVEFEKDLPHYHTKKGV

YIHGDTIECPVAMWLEALDLVLSKYREAKFPLNKVMAVSGSCQQHGSVYWSSQAESLLEQLNK

KPEKDLLHYVSSVAFARQTAPNWQDHSTAKQCQEFEECIGGPEKMAQLTGSRAHFRFTGPQILKI

AQLEPEAYEKTKTISLVSNFLTSILVGHLVELEEADACGMNLYDIRERKFSDELLHLIDSSSKDKTI

RQKLMRAPMKNLIAGTICKYFIEKYGFNTNCKVSPMTGDNLATICSLPLRKNDVLVSLGTSTTVL

LVTDKYHPSPNYHLFIHPTLPNHYMGMICYCNGSLARERIRDELNKERENNYEKTNDWTLFNQA

VLDDSESSENELGVYFPLGEIVPSVKAINKRVIFNPKTGMIEREVAKFKDKRHDAKNIVESQALSC

RVRISPLLSDSNASSQQRLNEDTIVKFDYDESPLRDYLNKRPERTFFVGGASKNDAIVKKFAQVIG

ATKGNFRLETPNSCALGGCYKAMWSLLYDSNKIAVPFDKFLNDNFPWHVMESISDVDNENWDR

YNSKIVPLSELEKTLI
```

(SEQ ID NO: 11)
```
ATGCTGTGCTCCGTTATACAAAGGCAAACAAGAGAAGTATCCAACACTATGTCTTTAGATAG

TTATTATCTAGGATTCGATTTAAGTACACAACAATTGAAATGTCTTGCTATAAACCAGGATCT

AAAGATCGTCCATTCCGAAACTGTCGAGTTCGAGAAGGACTTACCACATTATCACACCAAGA

AAGGCGTCTACATTCATGGTGACACCATCGAATGCCCAGTTGCTATGTGGTTAGAAGCCCTG

GATCTTGTCCTGTCCAAATATAGGGAGGCAAAGTTCCCACTGAACAAGGTCATGGCTGTTTC

CGGTTCTTGTCAGCAGCATGGCTCCGTCTACTGGTCATCACAGGCTGAATCTCTGTTAGAAC

AACTGAACAAGAAGCCAGAGAAGGACCTGTTACACTACGTCTCCTCTGTTGCATTTGCCAGA

CAAACTGCTCCTAATTGGCAAGACCATTCCACTGCTAAACAATGTCAGGAGTTCGAAGAGTG

TATTGGTGGACCAGAGAAAATGGCCCAGTTAACTGGTTCCCGTGCTCATTTCAGGTTCACAG

GCCCACAAATCCTGAAGATTGCTCAGTTAGAACCAGAGGCTTATGAAAAGACTAAGACCAT

CTCTTTGGTCTCTAATTTCTTAACTTCCATTCTGGTTGGTCACTTGGTCGAACTGGAAGAAGC

TGATGCGTGTGGTATGAACCTGTACGACATCCGTGAGAGGAAGTTCTCTGACGAACTGCTGC

ATCTTATCGACTCCTCCTCTAAGGACAAGACCATCAGGCAGAAACTGATGAGGGCACCAATG

AAGAACCTGATTGCCGGTACTATTTGCAAGTACTTCATCGAAAAGTATGGCTTCAACACCAA

CTGCAAAGTCTCCCCTATGACTGGCGATAACCTAGCCACCATTTGTAGCTTGCCCTTAAGAA

AAAACGATGTTCTTGTGTCTTTGGGTACTTCCACAACCGTCTTGTTGGTTACCGACAAATATC

ACCCTTCACCAAACTACCACCTGTTCATCCACCCGACGTTGCCTAACCACTACATGGGCATG

ATCTGCTACTGCAATGGCAGTTTAGCAAGGGAAAGGATAAGGGACGAGTTGAACAAGGAGA

GGGAGAACAACTACGAGAAGACCAACGATTGGACCCTGTTCAACCAAGCTGTCCTGGATGA

TAGCGAATCCTCCGAGAATGAACTGGGCGTTTACTTTCCACTAGGCGAGATCGTTCCATCTG

TCAAGGCCATCAACAAGAGAGTAATCTTCAACCCCAAGACTGGCATGATCGAAAGGGAAGT

CGCCAAGTTCAAGGACAAGAGACATGACGCCAAGAACATCGTTAATCTCAAGCCTTATCTT

GCCGTGTTAGGATTTCTCCCCTACTAAGCGACTCCAATGCTTCTTCCCAGCAACGTTTGAACG
```

-continued

AGGATACGATTGTTAAATTCGACTACGACGAGAGTCCATTGAGAGACTACTTGAACAAACGT

CCTGAGAGGACATTCTTTGTTGGTGGCGCATCCAAGAACGATGCTATTGTTAAGAAGTTTGC

TCAGGTCATAGGAGCAACCAAAGGTAACTTTCGTTTAGAAACTCCAAACTCATGCGCTTTAG

GTGGTTGCTACAAGGCTATGTGGTCTTTGTTGTATGATAGCAATAAAATCGCTGTTCCTTTCG

ACAAGTTCCTAAACGATAACTTCCCTTGGCACGTCATGGAATCCATCAGCGATGTAGACAAC

GAGAATTGGGATAGATACAATTCTAAAATAGTTCCCTTGTCTGAGTTAGAGAAGACCTTGAT

TTAATAA (SEQ ID NO: 12)
ATGTTGTGTTCTGTCATTCAAAGACAAACCAGAGAAGTTTCTAACACCATGTCTTTGGACTCT

TACTACTTGGGTTTCGACTTGTCTACCCAACAATTGAAGTGTTTGGCTATTAACCAAGACTTG

AAGATTGTCCACTCTGAAACCGTTGAGTTCGAAAAGGACTTGCCACACTACCACACCAAGAA

GGGTGTCTACATTCACGGTGACACCATTGAATGTCCAGTCGCTATGTTGGAAGCTTTGGACT

TGGTTTTGTCTAAGTACAGAGAAGCTAAGTTCCCATTGAACAAGGTCATGGCTGTCTCTGGT

TCTTGTCAACAACACGGTTCTGTCTACTCTTCTCAAGCTGAATCTTTGTTGGAACAATTGAAC

AAGAAGCCAGAAAAGGACTTGTTGCACTACGTCTCTTCTGTCGCTTTCGCTAGACAAACCGC

TCCAAACCAAGACCACTCTACCGCTAAGCAATGTCAAGAGTTCGAAGAATGTATTGGTGGTC

CAGAAAAGATGGCTCAATTGACCGGTAGTAGAGCACACTTCAGATTCACCGGTCCACAAATT

TTGAAGATTGCTCAATTGGAACCAGAAGCTTACGAAAAGACCAAGACCATTTCTTTGGTCTC

TAACTTCTTGACCTCTATTTTGGTCGGTCACTTGGTCGAATTGGAAGAAGCTGACGCTTGTGG

TATGAACTTGTACGACATTAGAGAAAGAAAGTTCTCTGACGAATTGTTGCACTTGATTGACT

CTTCTTCTAAGGACAAGACCATTAGACAAAAGTTGATGAGGGCTCCAATGAAGAACTTGATT

GCTGGTACCATTTGTAAGTACTTCATTGAAAAGTACGGTTTCAACACCAACTGTAAGGTCTC

TCCAATGACCGGTGACAACTTGGCTACCATTTGTTCTTTGCCATTGAGAAAGAACGACGTTTT

GGTTTCTTTGGGTACCTCTACCACCGTCTTGTTGGTTACCGACAAGTACCACCCATCTCCAAA

CTACCACTTGTTCATTCACCCAACCTTGCCAAACCACTACATGGGTATGATTTGTTACTGTAA

CGGTTCTTTGGCTAGAGAAAGAATTAGAGACGAATTGAACAAGGAAAGAGAAAACAACTAC

GAAAAGACCAACGACACCTTGTTCAACCAAGCTGTTTTGGACGACTCTGAATCTTCTGAAAA

CGAATTGGGTGTCTACTTCCCATTGGGTGAAATTGTTCCATCTGTCAAGGCTATTAACAAGA

GAGTCATTTTCAACCCAAAGACCGGTATGATTGAAAGAGAAGTCGCTAAGTTCAAGGACAA

GAGACACGACGCTAAGAACATTGTCGAATCTCAAGCTTTGTCTTGTAGAGTTAGAATTTCTC

CATTGTTGTCTGACTCTAACGCTTCTTCTCAACAAAGATTGAACGAAGACACCATTGTCAAG

TTCGACTACGACGAATCTCCATTGAGAGACTACTTGAACAAGAGACCAGAAAGAACCTTCTT

CGTTGGTGGTGCTTCTAAGAACGACGCTATTGTTAAGAAGTTCGCTCAAGTCATTGGTGCTA

CCAAGGGTAACTTCAGATTGGAAACCCCAAACTCTTGTGCTTTGGGTGGTTGTTACAAGGCT

ATGTCTTTGTTGTACGACTCTAACAAGATTGCTGTTCCATTCGACAAGTTCTTGAACGACAAC

TTCCCACACGTCATGGAATCTATTTCTGACGTTGACAACGAAAACGACAGATACAACTCTAA

GATTGTTCCATTGTCTGAATTGGAAAAGACCTTGATTTAATAA

Example 1

Construction of Plasmid PLS2802 with XR, XD and XK Genes

Xylose reductase from *Pichia stipitis* (XR.2; SEQ ID NO:3), xylitol dehydrogenase from *Pichia stipitis* (XD.2; SEQ ID NO:7), and xylulose kinase (XK.2; SEQ ID NO:11) from *Saccharomyces cerevisiae* were synthesized with codon optimization for expression in yeast. The genes were synthesized with the following 5' and 3' flanks to introduce specific restriction enzyme sites:

```
                                        (SEQ ID NO: 13)
XR - 5' GGATCCCAAACAAA;
and (SEQ ID NO: 14)
3' CATATG
to introduce 5'-BamH1 and 3'-Nde1;
```

The yeast vector p427TEF (Dualsystems Biotech AG) was used for gene expression. The vector contains a kanamycin resistance gene that allows for selection in yeast, an ampicillin resistance gene that allows for selection in *E. coli*, and a 2 micron origin of replication that allows for propagation of plasmids in high copy numbers in yeast. For cloning the pathway genes, p427TEF was digested with SacI and XhoI restriction enzymes. The larger fragment (6235 bp) was ligated with an oligomer of the following sequence, 5'GAGCTCACGGATCCGTCATATGCTA-GATCTCTGAATTCTTACTAGTTCGACGTCTACCTAG GCAGTCGACACGCGGCCGCTTCTCGAG 3' (SEQ ID NO:19) to introduce a new multiple cloning site (MCS) with desired restriction sites. Using the new MCS, the TEF1 promoter of *S. cerevisiae* was re-introduced in the vector using SacI/BamHI restriction sites to create PLS1567. To clone all 3 genes into one vector, additional promoters (Adh1p, GPDp) and terminators (Adh2t, Adh1t) were cloned into PLS1567 using yeast recombinational cloning using methods commonly used in the art. The promoters and terminators were each amplified using the primer sets shown in Table 1-1.

TABLE 1-1

Primers Used to Amplify Yeast Promoters and Terminators for PLS1448 Construction

| Cassette | Primer 1 | Primer 2 |
|---|---|---|
| ADH2 terminator | GCA TAG CAA TCT AAT CTA AGT TTT GGA TCC GTC ATA TGG CGG ATC TCT TAT GTC TTT ACG (SEQ ID NO: 20) | TTG TAT GTA CCT GTC TGA ATT CAG AGA TCT AGC CCT GAG AAA CTA TAT GAG GGT (SEQ ID NO: 21) |
| ADH1 promoter | ACC CTC ATA TAG TTT CTC AGG GCT AGA TCT CTG AAT TCA GAC AGG TAC ATA CAA (SEQ ID NO: 22) | TCA TAA ATC ATA AGA AAT TCG CGA CGT CGA ACT AGT TGT ATA TGA GAT AGT TGA TTG TAT GC (SEQ ID NO: 23) |
| ADH1 terminator | GCA TAC AAT CAA CTA TCT CAT ATA CAA CTA GTT CGA CGT CGC GAA TTT CTT ATG ATT TAT GA (SEQ ID NO: 24) | TGA TAA ACT CGA AGT CGA CTG CCT AGG CAT GCC GGT AGA GGT GTG GT (SEQ ID NO: 25) |
| GPD promoter | ACC ACA CCT CTA CCG GCA TGC CTA GGC AGT CGA CTT CGA GTT TAT CA (SEQ ID NO: 26) | GCG TGA CAT AAC TAA TTA CAT GAC TCG AGA AGC GGC CGC TTT GTT TGT TTA TGT GTGT (SEQ ID NO: 27) |

```
                        -continued
                                        (SEQ ID NO: 15)
XD- 5' ACTAGTCAAACAAA;
and (SEQ ID NO: 16)
3'-GACGTC
to introduce 5'SpeI and 3' AatII;
and (SEQ ID NO: 17)
XK- 5' GCGGCCGCCAAACAAA;
and (SEQ ID NO: 18)
3' CTCGAG
to introduce 5' NotI and 3' XhoI
```

SOE-PCR was used to combine the ADH2 terminator with the ADH1 promoter, and the ADH1 terminator with the GPD1 promoter. An internal AatII site in the ADH2 terminator was removed by changing its sequence from GACGTC (SEQ ID NO:28) to GATGTC (SEQ ID NO:29). For yeast recombinational cloning, PLS1567 was digested with BamHI/XhoI, and a 3:1 mass ratio of each insert to digested PLS1567 was used. The transformants were selected on culture plates containing G418. The resulting plasmid (PLS1448) with the 3 promoters and terminators was confirmed by sequencing. The 2 micron origin in PLS1448 was replaced with the CEN6/ARS4 origin of replication to yield PLS1565 with lower copy number and greater stability.

XR.2, XD.2 and XK.2 genes were then cloned into PLS1565 using yeast recombinational cloning. To amplify all the pieces, the primer sets provided in Table 1-2 were used.

TABLE 1-2

Primers Used to Amplify Cassettes for PLS2802 Construction

| Cassette | Primer 1 | Primer 2 |
|---|---|---|
| PS.XR.2 | CTT GCT CAT TAG AAA GAA AGC ATA GCA ATC TAA TCT AAG TTT TGG ATC CCA AAC AAA ATG TCC A (SEQ ID NO: 30) | CTA TAA ATC GTA AAG ACA TAA GAG ATC CGC CAT ATG TTA TTA AAC GAA CCC GAT TGG TAT CTT G (SEQ ID NO: 31) |

TABLE 1-2-continued

Primers Used to Amplify Cassettes for PLS2802 Construction

| Cassette | Primer 1 | Primer 2 |
|---|---|---|
| ADH2t-ADH1p | CAA GAT ACC AAT CTT CGT TTA GAG GGA TTA GCG GTC ATT TTG TTT ATG TCT TTA CGA TTT ATA G (SEQ ID NO: 32) | ATA ACA TAT GGC GGA TCT CTT GAC TAG TTG TAT ATG AGA TAG TTG ATT GTA TGC TTG GTA (SEQ ID NO: 33) |
| PS.XD.2 | TAC CAA GCA TAC AAT CAA CTA TCT CAT ATA CAA CTA GTC AAA CAA AAT GAC CGC TAA TCC CTC (SEQ ID NO: 34) | TAA TAA AAA TCA TAA ATC ATA AGA AAT TCG CGA CGT CTT ATT ATT CTG GAC CAT CAA TCA (SEQ ID NO: 35) |
| ADH1t-GPDp | TGA TTG ATG GTC CAG AAT AAT AAG ACG TCG CGA ATT TCT TAT GAT TTA TGA TTT TTA TTA (SEQ ID NO: 36) | TTT GTA TAA CGG AGC ACA GCA TTT TGT TTG GCG GCC GCT TTG TTT GTT TAT GTG TGT TTA T (SEQ ID NO: 37) |
| SC.XK.2 | ATA AAC ACA CAT AAA CAA ACA AAG CGG CCG CCA AAC AAA ATG CTG TGC TCC GTT ATA CAA A (SEQ ID NO: 38) | GGG GAG GGC GTG AAT GTA AGC GTG ACA TAA CTA ATT ACA TGA CTC GAG TTA TTA AAT CAA GGT CTT CTC T (SEQ ID NO: 39) |

For yeast recombinational cloning, PLS1565 was digested with BamHI/XhoI and gel purified. Then, a 3:1 mass ratio of each insert:digested PLS1565 was used. Transformants were selected using G418 and confirmed by sequencing. The resulting plasmid (PLS2802) with the 3 genes cloned is depicted in FIG. 3.

Example 2

Transformation of PLS2802 into Yeast and Fermentation

PLS2802 was used to transform S. cerevisiae (THERMO-SACC®; LYCC6825; Lallemand) Transformants were selected on YPD agar plates with 200 ug/ml G418 at 30° C. for 48 hrs. Single colonies were used to inoculate 2500 of defined media (60 g/L glucose; 3 g/L potassium phosphate, 5 g/L ammonium sulphate, 0.5 g/L magnesium sulphate, 100 mM MES pH 5.5) in Axygen 96-well plates. The cultures were grown at 30° C. for 72 hrs with 85% relative humidity. Then, 40 μl of the culture was used to inoculate 360 μl of 3:1 mixture of defined media (60 g/L glucose; 3 g/L potassium phosphate, 5 g/L ammonium sulphate, 0.5 g/L magnesium sulphate, 100 mM MES pH 5.5) to plant (wheat straw) biomass hydrolysates containing xylose in 96-well Costar deep well plates for propagating the cells. The cultures were grown at 30° C. for 40 hrs with 250 rpm shaking. At 40 hrs, the cells were spun down at 22° C. for 10 mins and evaluated for xylose fermentation activity.

For fermentation, cells were re-suspended in 400 ul of plant (wheat straw) biomass hydrolysates containing xylose and the plates were sealed with mats. Plates were incubated at 30° C., with 100 rpm shaking. At different timepoints, cells were harvested and the residual sugars and ethanol in the supernatant were measured by a standard HPLC based method known in the art (See e.g., DuPont et al., Carb. Polym., 68:1-16 [2007], which is incorporated herein by reference). In some experiments, the residual xylose in the supernatant was measured using a spectrophotometric assay (e.g., Megazyme xylose assay; Cat no. K-XYLOSE) performed according to the manufacture's protocol. Strains transformed with the empty vector were used as a control. Strains transformed with the xylose pathway consumed significantly higher amounts of xylose at each of the timepoints tested compared to the vector control.

Example 3

Effect of Codon Optimization on XR, XD Activity

To evaluate the effect of codon optimization, alternate sequences of XR and XD genes were tested. Each of the genes were synthesized with either their native Pichia stiptis sequence (XR.1, XD.1) or with codon optimization towards highly expressed yeast sequences (XR.3; XD.3) (Brat et al Appl. Environ. Microbiol., 75:2304-2311 [2009]). To evaluate the effect of the optimization, XR and XD genes were cloned into vector PLS1448 with different combinations (XR.1-XD.1-XK.2; XR.2-XD.1-XK.2; XR.3-XD.1-XK.2; XR.1-XD.2-XK.2; XR.1-XD.3-XK.2). The variants were used to transform S. cerevisiae (THERMOSACC®; LYCC6469; Lallemand). Transformants were selected on YPD agar plates containing 200 ug/ml G418 at 30° C. for 48 hrs. Single colonies were used to inoculate 250 μl of YPD in Axygen 96-well plates. The cultures were grown at 30° C. for 72 hrs with 85% relative humidity. Then, 40 μl of the culture was used to inoculate 360 μl of YPD with 20 g/L xylose in 96 well Costar deep well plates for propagating the cells. The cultures were grown at 30° C. for 40 hrs with 250 rpm shaking. At 40 hrs, the cells were spun down at 22° C. for 10 mins and evaluated for xylose fermentation activity.

For fermentation, cells were re-suspended in 400 ul of YPD with 20 g/L xylose and the plates were sealed with mats. Plates were incubated at 30° C. at 100 rpm shaking. At 48 hrs, cells were harvested and the residual xylose in the supernatant was measured by a spectrophotometric assay as described above. The best xylose consumption was seen with XR.1-XD.2-XK.2 (PLS6058) variant (See, Table 3-1).

TABLE 3-1

Xylose Consumption by Yeast Strain Transformed With Xylose Pathway

| Strain | Xylose Consumed (g/L) |
|---|---|
| THERMOSACC ® + PLS1448 (vector control) | 2.5 |
| THERMOSACC ® + XR.2-XD.2-XK.2 | 12.5 |
| THERMOSACC ® + XR.1-XD.2-XK.2 | 15.8 |
| THERMOSACC ® + XR.3-XD.2-XK.2 | 2.5 |
| THERMOSACC ® + XR.2-XD.1-XK.2 | 13.8 |
| THERMOSACC ® + XR.2-XD.3-XK.2 | 13.5 |

Example 4

Construction of XR and XD Variant Libraries

*Pichia stipitis* xylose reductase and xylitol dehydrogenase were subjected to directed evolution algorithms to improve xylose utilization activity using methods as known in the art (See e.g., WO 2010/144103). Purified PCR products encoding XR and/or XD variants (i.e., comprising amino acid substitutions) and the vector portion of plasmid PLS2802 were pooled and used to transform *S. cerevisiae* (THERMO-SACC®; LYCC6825; Lallemand) to produce a library via homologous recombination (See e.g., Oldenburg et al., Nucl. Acids Res., 25(2):451-452 [1997], which is incorporated herein by reference). The library was screened for xylose fermentation activity as described in Example 2. The xylose utilization was measured relative to the positive control (XR.1-XD.2-XK.2). Strains that had activity significantly above the positive control were retested in replicate and the variants sequenced to identify mutations. The results are provided in the following Tables.

TABLE 4-1

XR and XD Variants Exhibiting Improved Activity

| Variant No: | XR Active Mutations wrt XR WT | XR Silent Mutations wrt XR WT | XD Active Mutations wrt XD WT | XD Silent Mutations wrt XD WT | Xylose utilization Activity compared to WT *P. stipitis* XR/XD |
|---|---|---|---|---|---|
| 1 (WT & Positive Control) | | | | | 1.0 |
| 2 | R276F | t811a/c812g/c816t | I208R | | ≥1.0 |
| 3 | R276F | t811a/c812g/c816t | F209S/N211K | | ≥1.0 |
| 4 | S271G | c816t/a826c/a828t | I208R/N211K | | ≥1.0 |
| 5 | S271G | c816t/a826c/a828t | I208R/N211S | | ≥1.0 |
| 6 | R276F | t811a/c812g/c816t | I208R/F209S/N211S | | ≥1.0 |
| 7 | S271G | c816t/a826c/a828t; | I208R | | ≥1.0 |
| 8 | K270R | t811a/c812g/c816t/ a826c/a828t | I208R/N211R | | ≥1.0 |
| 9 | K270R | t811a/c812g/c816t/ a826c/a828t | F209S/N211K | | ≥1.0 |
| 10 | N272P/R276F | t811a/c812g | F209S/N211K | | ≥1.0 |
| 11 | K270R/N272P/R276F | t811a/c812g | N211K | | ≥1.0 |
| 12 | | t811a/c812g/c816t/ a826c/a828t | I208R | | ≥1.0 |

TABLE 4-2

XR Variants with Improved Activity

| Variant No: | XR- Active Mutations wrt XR WT | XR- Silent Mutations wrt XR WT | Xylose Utilization Activity Compared to WT *P. stipitis* XR/XD |
|---|---|---|---|
| 1 (WT and Positive Control) | | | 1.00 |
| 13 | R276W | | ≥1.5 |
| 14 | A266V | | ≥1.4 |
| 15 | T232V | | ≥1.4 |
| 16 | I267V | | ≥1.4 |
| 17 | V255I | | ≥1.4 |
| 18 | P2T/A266C | | ≥1.4 |
| 19 | S233V | | ≥1.4 |
| 20 | K152E | | ≥1.3 |
| 21 | L224S | | ≥1.3 |
| 22 | A246L | | ≥1.3 |
| 23 | | a280c/a282t | ≥1.3 |
| 24 | K132N | | ≥1.3 |
| 25 | R276M | | ≥1.3 |
| 26 | K132A | | ≥1.3 |
| 27 | N302S | | ≥1.3 |
| 28 | R206S | | ≥1.3 |
| 29 | A246S | | ≥1.3 |
| 30 | A49G | | ≥1.3 |
| 31 | S261N | | ≥1.2 |
| 32 | K36Q | | ≥1.2 |
| 33 | T232A | | ≥1.2 |
| 34 | K155R | | ≥1.2 |
| 35 | | c438t | ≥1.2 |
| 36 | L224A | | ≥1.2 |
| 37 | S261A | | ≥1.2 |
| 38 | K152H | | ≥1.2 |
| 39 | D134E | | ≥1.2 |
| 40 | | c906t | ≥1.2 |
| 41 | I62V | | ≥1.2 |
| 42 | V283H | | ≥1.2 |
| 43 | L108Y | | ≥1.2 |
| 44 | | c201t | ≥1.2 |
| 45 | D11K | | ≥1.2 |
| 46 | S233C | | ≥1.2 |
| 47 | D134V | | ≥1.2 |
| 48 | S285E | | ≥1.2 |
| 49 | A245S | | ≥1.2 |
| 50 | S233I | | ≥1.2 |
| 51 | S3R | | ≥1.2 |
| 52 | I62L | | ≥1.2 |
| 53 | | c306t | ≥1.2 |
| 54 | G157R | | ≥1.2 |

TABLE 4-2-continued

XR Variants with Improved Activity

| Variant No: | XR- Active Mutations wrt XR WT | XR- Silent Mutations wrt XR WT | Xylose Utilization Activity Compared to WT P. stipitis XR/XD |
|---|---|---|---|
| 55 | T114S | | ≥1.2 |
| 56 | L224V | | ≥1.2 |
| 57 | | t511c/g513t | ≥1.2 |
| 58 | R33L | | ≥1.2 |
| 59 | V24G | | ≥1.2 |
| 60 | S233K | | ≥1.2 |
| 61 | | t358c/a360g | ≥1.2 |
| 62 | | t82a/c83g | ≥1.2 |
| 63 | K68G | | ≥1.2 |
| 64 | N302D | | ≥1.2 |
| 65 | D282G | | ≥1.1 |
| 66 | R206V | | ≥1.1 |
| 67 | | a426t | ≥1.1 |
| 68 | G249D | | ≥1.1 |
| 69 | | t511c/g513t | ≥1.1 |
| 70 | V318C | | ≥1.1 |
| 71 | L303V | | ≥1.1 |
| 72 | P252C | | ≥1.1 |
| 73 | E89V | | ≥1.1 |
| 74 | | a478c/g480t | ≥1.1 |
| 75 | | t703c | ≥1.1 |
| 76 | | a378t | ≥1.1 |
| 77 | S97T | | ≥1.1 |
| 78 | K155Y | c855t | ≥1.1 |
| 79 | N231L | | ≥1.1 |
| 80 | N225K | | ≥1.1 |
| 81 | N225S | | ≥1.1 |
| 82 | S3H | | ≥1.1 |
| 83 | A56E | | ≥1.1 |
| 84 | | c201t | ≥1.1 |
| 85 | K152A | | ≥1.1 |
| 86 | P168S | | ≥1.1 |
| 87 | D134H | | ≥1.1 |
| 88 | N225D | | ≥1.1 |
| 89 | Q226D | | ≥1.1 |
| 90 | S233G | | ≥1.1 |
| 91 | D282C | | ≥1.1 |
| 92 | E89N | | ≥1.1 |
| 93 | | t670c/g672t | ≥1.1 |
| 94 | K281L | | ≥1.1 |
| 95 | N302G | | ≥1.1 |
| 96 | A297H | | ≥1.1 |
| 97 | Q226E | | ≥1.1 |
| 98 | S233F | | ≥1.1 |
| 99 | K123C | | ≥1.1 |
| 100 | S261T | | ≥1.1 |
| 101 | K152Q | | ≥1.1 |
| 102 | R33V | | ≥1.1 |
| 103 | A14V | | ≥1.1 |
| 104 | S97R | | ≥1.1 |
| 105 | | a585g | ≥1.1 |
| 106 | K155D | | ≥1.1 |
| 107 | Q226S | | ≥1.1 |
| 108 | Q219T | | ≥1.1 |
| 109 | I143L | | ≥1.1 |
| 110 | D102T; | | ≥1.1 |
| 111 | N231H; | | ≥1.1 |
| 112 | T232S | | ≥1.0 |
| 113 | N225E | | ≥1.0 |
| 114 | S184A | | ≥1.0 |
| 115 | S3W | | ≥1.0 |
| 116 | D282R | | ≥1.0 |
| 117 | Q219L | | ≥1.0 |
| 118 | T232C | | ≥1.0 |
| 119 | R228T | | ≥1.0 |
| 120 | K281V | | ≥1.0 |
| 121 | S285T | | ≥1.0 |
| 122 | | t688c | ≥1.0 |
| 123 | N231S | | ≥1.0 |
| 124 | | c849g | ≥1.0 |
| 125 | K155I | | ≥1.0 |
| 126 | N231G | | ≥1.0 |
| 127 | K242L | | ≥1.0 |
| 128 | | t354g | ≥1.0 |
| 129 | A297S | | ≥1.0 |
| 130 | K68M | | ≥1.0 |
| 131 | | c408t | ≥1.0 |
| 132 | | t766c | ≥1.0 |
| 133 | T240V | | ≥1.0 |
| 134 | E46K/ D47N | | ≥1.0 |
| 135 | I301Y | | ≥1.0 |
| 136 | I301C | | ≥1.0 |
| 137 | Q226V | | ≥1.0 |
| 138 | L303I | | ≥1.0 |
| 139 | E279Q | | ≥1.0 |
| 140 | P275A | | ≥1.0 |
| 141 | D23E/K68R | | ≥1.0 |
| 142 | F236L | | ≥1.0 |
| 143 | Q219H | | ≥1.0 |
| 144 | N225Y | | ≥1.0 |
| 145 | N7L | | ≥1.0 |
| 146 | A56Y | | ≥1.0 |
| 147 | F17W | | ≥1.0 |
| 148 | K155A | | ≥1.0 |
| 149 | K116Q | | ≥1.0 |
| 150 | S261C | | ≥1.0 |

TABLE 4-3

Additional XR Variants with Improved Activity

| Variant No. | XR- Active Mutations wrt XR WT | XR- Silent Mutations wrt XR WT | Xylose Utilization Activity (Compared to Positive Control) |
|---|---|---|---|
| 13 (Positive Control) | R276W | | 1.00 |
| 151 | P2T/R206S/R276W | | ≥1.4 |
| 152 | P2T/A49G/R276W | | ≥1.4 |
| 153 | P2T/A49G/R206S/R276W | | ≥1.4 |
| 154 | P2T/R276W | | ≥1.3 |
| 155 | A49G/R276W | | ≥1.3 |
| 156 | P2T/K132N/K152E/R276W | | ≥1.3 |
| 157 | P2T/A49G/R276W | a280c | ≥1.2 |
| 158 | G227D/R276W | t6g | ≥1.2 |
| 159 | A49G/K132A/R206S/R276W | | ≥1.2 |
| 160 | P2T/P168S/R276W | a853t/g854c/c954g | ≥1.2 |
| 161 | A49G; K152E; R276W | a280c | ≥1.2 |

TABLE 4-3-continued

Additional XR Variants with Improved Activity

| Variant No. | XR- Active Mutations wrt XR WT | XR- Silent Mutations wrt XR WT | Xylose Utilization Activity (Compared to Positive Control) |
|---|---|---|---|
| 162 | R276W | c54t | ≥1.2 |
| 163 | P2T/A49G/R276W/V318C | a853t/g854c | ≥1.2 |
| 164 | P2T/A49G/K132N/R276W | | ≥1.2 |
| 165 | P2T/K132N/R276W | a280c | ≥1.2 |
| 166 | P2T/K132N/R276W | | ≥1.2 |
| 167 | P2T/G157R/R276W | g324a/c402t/a853t/g854c/c954g | ≥1.2 |
| 168 | R33L/A56E/R276W | t7a/c8g/g456a | ≥1.1 |
| 169 | A49G/R276W | t753c | ≥1.1 |
| 170 | S3H/R33L/A56E/R276W | | ≥1.1 |
| 171 | A49G/R276W | a280c | ≥1.1 |
| 172 | R276W | t82a/c83g/c201t | ≥1.1 |
| 173 | P2T/R276W | c954g | ≥1.1 |
| 174 | S3H/T114S/R276W/N302S | t699c/a756c | ≥1.1 |
| 175 | P2T/R276W | t552c | ≥1.1 |
| 176 | A49G/K132N/R206S/S233V/R276M/N302S | | ≥1.1 |
| 177 | A49G/K132A/R276W | a280c | ≥1.1 |
| 178 | R276W/V318C | t6g/t781a/c782g/a853t/g854c | ≥1.1 |
| 179 | P2T/A246L/R276W | t781a/c782g/c954g | ≥1.1 |
| 180 | P2T/A49G/K152E/R276W | | ≥1.1 |
| 181 | K155R/R206S/R276W | | ≥1.1 |
| 182 | R276W | g204a | ≥1.1 |
| 183 | R276W | a853t/g854c/c954g | ≥1.1 |
| 184 | R276W | c201t/a280c | ≥1.1 |
| 185 | T114S/R276W | | ≥1.1 |
| 186 | R33L/R276W | t7a/c8g | ≥1.1 |
| 187 | R276W | c954g | ≥1.1 |
| 188 | P2T/R276W/V318C | | ≥1.1 |
| 189 | A49G/K152E/R276W | | ≥1.1 |
| 190 | D11K/V255I/R276M | g231a/c801t | ≥1.1 |
| 191 | K132N/R276W | a280c | ≥1.1 |
| 192 | K52R/R276W | | ≥1.0 |
| 193 | P2T/A49G/S233V/A246L/R276W/N302S | | ≥1.0 |
| 194 | A49G/K132A/K152E/R276W | a280c | ≥1.0 |
| 195 | S3H/R276W | t99g/c168a | ≥1.0 |
| 196 | P2T/V24G/A49G/R276W | c954g | ≥1.0 |
| 197 | R276W | c201t | ≥1.0 |
| 198 | R276W/V318C | t6g | ≥1.0 |
| 199 | R33L/A56E/R276W | t7a/c8g | ≥1.0 |
| 200 | K132N/R276W | g465a/t618c/t907c | ≥1.0 |
| 201 | K132N/K155R/R276W/V283H | t907c | ≥1.0 |
| 202 | K36Q/R276W | | ≥1.0 |
| 203 | R276W | a478c | ≥1.0 |
| 204 | R276W | c855t | ≥1.0 |
| 205 | R276W | t82a/c83g | ≥1.0 |
| 206 | P2T/A49G/S261N/R276W | a853t/g854c/c954g | ≥1.0 |
| 207 | P2T/K132A/R276W | a280c | ≥1.0 |
| 208 | K132N/R276W | | ≥1.0 |
| 209 | R276W | t7a/c8g | ≥1.0 |
| 210 | P168S/R276W | | ≥1.0 |
| 211 | A56E/T114S/R276W | t7a/c8g | ≥1.0 |
| 212 | P2T/A49G/K68G/S261N/R276W/V318C | a853t/g854c | ≥1.0 |
| 213 | R276W | c906t | ≥1.0 |
| 214 | A49G/K132N/K152E/R276W/N302S | a280c | ≥1.0 |
| 215 | R276W | g108a/t907c | ≥1.0 |
| 216 | K132N/R276W | t289a/c290g/t291c | ≥1.0 |
| 217 | D11K/R276W | g108a/g465a | ≥1.0 |
| 218 | R276W | t82a/c83g/c201t/a280c/t358c/a378t/t511c | ≥1.0 |
| 219 | P252C/R276W | | ≥1.0 |
| 220 | R276W | c21t | ≥1.0 |
| 221 | P2T/A49G/R276W/N302S | | ≥1.0 |
| 222 | P2T/V24G/R276W/V318C | | ≥1.0 |
| 223 | Dl1K/K155Y/R206S/R276W | g108a/t289a/c290g/t291c | ≥1.0 |
| 224 | S3H/R33L/T114S/R276W | c168a | ≥1.0 |

TABLE 4-4

Additional XR Variants with Improved Activity

| Variant No: | XR- Active Mutations wrt XR WT | XR- Silent Mutations wrt XR WT | Xylose Utilization Activity (Compared to Positive Control) |
|---|---|---|---|
| 272 (Positive Control) | P2T/A49G/K132N/S233K/I267V/R276W | t99a/g156a/t747c/t751a/c752g, t753c | 1.00 |
| 377 | P2T/E46C/A49G/F107Y/K132N/S233K/I267V/R276W | t99a/g156a/t747c/t751a/c752g/t753c | ≥1.2 |
| 378 | P2T/C19L/E46C/A49G/F107Y/K132N/S233K/I267V/R276W | t99a/g156a/t747c/t751a/c752g/t753c | ≥1.1 |
| 379 | P2T/A49G/K132N/S233K/I267V/R276W | t99a/g156a/t552g/t747c/t751a/c752g/t753c/a756t/c816t | ≥1.1 |
| 380 | P2T/A49G/K132N/S233K/I267V/R276W | t99a/g108a/g156a/t322c/t747c/t751a/c752g/t753c | ≥1.0 |
| 381 | P2T/A49G/K132N/S233K/I267V/R276W | t99a/g156a/t552g/t747c/t751a/c752g/t753c | ≥1.0 |
| 382 | P2T/E46C/A49G/K132N/V164I/S233K/I267V/R276W | t99a/g156a/t747c/t751a/c752g/t753c | ≥1.0 |
| 383 | P2T/C19L/E46C/A49G/K132N/S233K/I267V/R276W | t99a/g156a/t747c/t751a/c752g/t753c | ≥1.0 |
| 384 | P2T/A49G/K132N/S233K/R276W | t99a/g108a/g156a/t747c/t751a/c752g/t753c/c801t | ≥1.0 |
| 385 | P2T/A49G/K132N/P168S/S233K/I267V/R276W | t99a/g156a/t322c/t747c/t751a/c752g/t753c | ≥1.0 |
| 386 | P2T/A49G/K132N/P168S/S233K/I267V/R276W | t99a/g108a/g156a/t322c/g513a/t747c/t751a/c752g/t753c/c816t | ≥1.0 |

In some additional experiments, the *Pichia stipitis* xylitol dehydrogenase (XD.2) was subjected to directed evolution to improve xylose utilization activity using PCR amplification known in the art (See e.g., WO 2010/144103). Purified PCR products were pooled and transformed into *S. cerevisiae* (THERMOSACC®; LYCC6825; Lallemand) to produce the library via homologous recombination (See e.g., Oldenburg et al., Nucl. Acids Res., 25(2):451-452 [1997], which is incorporated herein by reference). The library was screened for xylose fermentation activity as described in Example 2. Variants that exhibited activity significantly above the positive control were retested and sequenced. Variants that exhibited activity improved above background are provided in Table 4-5.

TABLE 4-5

XD Variants with Improved Activity

| Variant No: | XD- Active Mutations wrt XD WT | XD- Silent Mutations wrt XD WT | Xylose Utilization Activity (Compared to Positive Control) |
|---|---|---|---|
| 13 (Positive Control) | | | 1.00 |
| 225 | E235K | | ≥1.2 |
| 226 | V206A | | ≥1.2 |
| 227 | A49Q | | ≥1.2 |
| 228 | K352E | | ≥1.2 |
| 229 | M215C | | ≥1.1 |
| 230 | P256A | | ≥1.1 |
| 231 | | t24g | ≥1.1 |
| 232 | S81G | | ≥1.1 |
| 233 | | a768t | ≥1.1 |
| 234 | T19L | | ≥1.1 |
| 235 | G202D | | ≥1.1 |
| 236 | L189C | | ≥1.1 |
| 237 | P5R | | ≥1.1 |
| 238 | G231H | | ≥1.1 |
| 239 | D210W | | ≥1.1 |
| 240 | T230V | | ≥1.1 |
| 241 | | a780g | ≥1.1 |
| 242 | | a732g | ≥1.1 |
| 243 | T286V | | ≥1.1 |
| 244 | | c630t | ≥1.1 |
| 245 | G231A | | ≥1.1 |
| 246 | P5E | | ≥1.1 |
| 247 | D218R | | ≥1.1 |
| 248 | S228P | | ≥1.0 |
| 249 | T19Q | | ≥1.0 |
| 250 | V287L | | ≥1.0 |
| 251 | V205C | | ≥1.0 |
| 252 | V205H | | ≥1.0 |
| 253 | V187M | | ≥1.0 |
| 254 | H149R | | ≥1.0 |
| 255 | F296R | | ≥1.0 |
| 256 | A239C | | ≥1.0 |
| 257 | L260Q | | ≥1.0 |
| 258 | G241W/K307R | | ≥1.0 |
| 259 | E235Q | | ≥1.0 |
| 260 | D13G | | ≥1.0 |
| 261 | A350D | | ≥1.0 |
| 262 | T252S | | ≥1.0 |
| 263 | C251T | | ≥1.0 |
| 264 | N227T | | ≥1.0 |
| 265 | M215A | | ≥1.0 |
| 266 | C251G | | ≥1.0 |
| 267 | K229R | | ≥1.0 |
| 268 | F226V | | ≥1.0 |
| 269 | P256Q | | ≥1.0 |
| 270 | D327A | | ≥1.0 |

The following Table (Table 4-6) provides results for XR and XD combinatorial variants with improved activity compared to a positive control having the active mutations indicated in the Table.

TABLE 4-6

XR & XD Combinatorial Variants with Improved Activity

| | XR | | XD | | Xylose Utilization |
|---|---|---|---|---|---|
| Variant No. | Active Mutations wrt XR WT | Silent Mutations wrt XR WT | Active Mutations wrt XD WT | Silent Mutations wrt XD WT | Activity Improvement (Relative to Positive Control) |
| 152 (Positive Control) | P2T/A49G/R276W | | | | 1.00 |
| 271 | P2T/K132N/K152E/R276W | | F209S/N211K | | ≥1.2 |
| 272 | P2T/A49G/K132N/S233K/I267V/R276W | t99a/g156a/t747c/t751a/c752g/t753c | | | ≥1.2 |
| 273 | P2T/A49G/K132N/I267V/R276W | t99a/g204a/t618c/t697a/c698g/t699c/t747c/t751a/c752g/t753c | | | ≥1.2 |
| 274 | P2T/A49G/P168S/R206S/I267V/R276W | g456a/t895c | | | ≥1.2 |
| 275 | P2T/A49G/K52R/K152E/S233K/I267V/R276W | g231a/t322c | | | ≥1.2 |
| 276 | P2T/A49G/K132N/E67V/R276W | | | | ≥1.2 |
| 277 | P2T/A49G/R276W | | G232L | | ≥1.2 |
| 278 | P2T/A49G/K132N/R276W | t99a/g204a | | | ≥1.2 |
| 279 | P2T/A49G/K132N/I267V/R276W | t99a/t747c/t751a/c752g/t753c | | | ≥1.2 |
| 280 | P2T/A49G/K132N/R276W | t99g/g108a/a853t/g854c/c855g | | | ≥1.2 |
| 281 | P2T/A49G/S233K/I267V/R276W | t99a/g513a/t747c/t751a/c752g/t753c | | | ≥1.2 |
| 282 | P2T/A49G/R206S/S233K/I267V/R276W | t895c | | | ≥1.2 |
| 283 | P2T/A49G/K132N/R276W | g156a/g204a/c801t | | | ≥1.2 |
| 284 | P2T/A49G/K132N/R276W | t753g/a756t/a853t/g854c/c855g | | | ≥1.2 |
| 285 | P2T/A49G/S233K/I267V/R276W | t895c | | | ≥1.2 |
| 286 | P2T/A49G/K152E/P168S/S233V/I267V/R276W | t895c | | | ≥1.1 |
| 287 | P2T/A49G/S233K/I267V/R276W | t618c/t747c/t751a/c752g/t753c | | | ≥1.1 |
| 288 | P2T/A49G/R276W | | T225X | a693w | ≥1.1 |
| 289 | P2T/A49G/R276W | | | c336t | ≥1.1 |
| 290 | P2T/A49G/S233K/I267V/R276W | t322c/t895c | | | ≥1.1 |
| 291 | P2T/A49G/R276W | | E235K | | ≥1.1 |
| 292 | P2T/A49G/S233K/I267V/R276W | t618c/t895c | | | ≥1.1 |
| 293 | P2T/A49G/R276W | | K214A | | ≥1.1 |
| 294 | P2T/A49G/K132N/I267V/R276W | t99a/g156a | | | ≥1.1 |
| 295 | P2T/A49G/R276W | | K229V | | ≥1.1 |
| 296 | P2T/A49G/R276W | | | | ≥1.1 |
| 297 | P2T/A49G/R206S/S233K/I267V/R276W | t9c/t895c | | | ≥1.1 |
| 298 | P2T/A49G/I267V/R276W | t99a/t697a/c698g/t699c/t747c/t751a/c752g/t753c | | | ≥1.1 |
| 299 | P2T/A49G/P168S/S233K/R276W | t9c/t618c | | | ≥1.1 |
| 300 | P2T/A49G/S233K/I267V/R276W | g834a/t895c | | | ≥1.1 |
| 301 | P2T/A49G/G227D/P252C/G264D/R276W | t753g | | | ≥1.1 |

TABLE 4-6-continued

XR & XD Combinatorial Variants with Improved Activity

| | XR | | XD | | Xylose Utilization |
|---|---|---|---|---|---|
| Variant No. | Active Mutations wrt XR WT | Silent Mutations wrt XR WT | Active Mutations wrt XD WT | Silent Mutations wrt XD WT | Activity Improvement (Relative to Positive Control) |
| 302 | P2T/A49G/K132N/ R276W | a853t/g854c/ c855g | | | ≥1.1 |
| 303 | P2T/S3H/A49G/P168S/ S233K/R276W | g456a/c801t/ t895c | | | ≥1.1 |
| 304 | P2T/A49G/S233K/ I267V/R276W | t99a/t618c/ t747c/t751a/ c752g/t753c | | | ≥1.1 |
| 305 | P2T/R206S/R276W | | A49Q | | ≥1.1 |
| 306 | P2T/A49G/I267V/ R276W | g156a | | | ≥1.1 |
| 307 | P2T/A49G/I267V/ R276W | t895c/ | | | ≥1.1 |
| 308 | P2T/A49G/R206S/ S233V/R276W | a504g | | | ≥1.1 |
| 309 | P2T/A49G/I267V/ R276W | t99a | | | ≥1.1 |
| 310 | P2T/A49G/S233K/ R276W | c801t/t895c | | | ≥1.1 |
| 311 | P2T/A49G/R206S/ R276W | t697a/c698g/ c801t/t895c | | | ≥1.1 |
| 312 | P2T/A49G/P252C/ R276W | t753g/a853t/ g854c/c855g | | | ≥1.1 |
| 313 | P2T/K132N/K152E/ R276W | | K352E | | ≥1.1 |
| 314 | P2T/A49G/I267V/ R276W | t747c/t751a/ c752g/t753c | | | ≥1.1 |
| 315 | P2T/A49G/I267V/ R276W | | | | ≥1.1 |
| 316 | P2T/A49G/R276W | | C251A | | ≥1.1 |
| 317 | P2T/A49G/R276W | | G232R | | ≥1.1 |
| 318 | P2T/A49G/R206S/ S233V/R276W | c801t/t895c | | | ≥1.1 |
| 319 | P2T/A49G/K132N/ R276W | g204a/t753g/ a756t/a853t/ g854c/c855g | | | ≥1.1 |
| 320 | P2T/A49G/R206S/ R276W | t697a/c698g/ t699c | | | ≥1.1 |
| 321 | P2T/A49G/R276W | | K229M | | ≥1.1 |
| 322 | P2T/A49G/S233K/ I267V/R276W | t322c/t618c/ t895c | | | ≥1.1 |
| 323 | P2T/K132N/K152E/ R276W | | A49Q/E235K | | ≥1.1 |
| 324 | P2T/A49G/R276W | | | a780t | ≥1.1 |
| 325 | P2T/A49G/I267V/ R276W | t99a/g156a/ g204a | | | ≥1.1 |
| 326 | P2T/A49G/R276W | | D327X | | ≥1.1 |
| 327 | P2T/K132N/K152E/ R276W | | A49Q | | ≥1.1 |
| 328 | P2T/A49G/P168S/ R276W | | | | ≥1.1 |
| 329 | P2T/A49G/R276W | | V206A | | ≥1.0 |
| 330 | P2T/A49G/R276W | | V206A | | ≥1.0 |
| 331 | P2T/A49G/R276W | | K337R | | ≥1.0 |
| 332 | P2T/A49G/K152E/ I267V/R276W | a504g | | | ≥1.0 |
| 333 | P2T/A49G/K132N/ R276W | a478c/g480t | | | ≥1.0 |
| 334 | P2T/K36Q/A49G/ G227D/R276W | t99g/t753g/ a756t/a853t/ g854c/c855g | | | ≥1.0 |
| 335 | P2T/A49G/R276W | | V287L | | ≥1.0 |
| 336 | P2T/A49G/D86N/ K132N/R276W | g204a/a478c/ g480t/t753g/ a756t/a853t/ g854c/c855g | | | ≥1.0 |
| 337 | P2T/A49G/R206S/ R276W | | A49Q | | ≥1.0 |
| 338 | P2T/A49G/R276W | | G241E | | ≥1.0 |
| 339 | P2T/A49G/G227D/ R276W | t753g/a756t/ a853t/g854c/ c855g | | | ≥1.0 |

TABLE 4-6-continued

XR & XD Combinatorial Variants with Improved Activity

| | XR | | XD | | Xylose Utilization |
|---|---|---|---|---|---|
| Variant No. | Active Mutations wrt XR WT | Silent Mutations wrt XR WT | Active Mutations wrt XD WT | Silent Mutations wrt XD WT | Activity Improvement (Relative to Positive Control) |
| 340 | P2T/S3X/A49G/S233X/ I267X/R276W/L299X | t84w | | | ≥1.0 |
| 341 | P2T/A49G/I267V/ R276W | a504g/c816t/ t895c | | | ≥1.0 |
| 342 | P2T/A49G/R276W | | H112Q | | ≥1.0 |
| 343 | P2T/A49G/R276W | | K238G | | ≥1.0 |
| 344 | P2T/A49G/P168S/ R276W | t895c | | | ≥1.0 |
| 345 | P2T/A49G/G227D/ I267V/R276W | | | | ≥1.0 |
| 346 | P2T/A49G/K132N/ G227D/P252C/R276W | t753g/a853t/ g854c/c855g | | | ≥1.0 |
| 347 | P2T/A49G/R276W | | K352Q | | ≥1.0 |
| 348 | P2T/A49G/I267V/ R276W | g204a/t697a/ c698g/t699c/ t747c/t751a/ c752g/t753c | | | ≥1.0 |
| 349 | R276F | t811a/c812g/ c816t | I208R/N211K | | ≥1.0 |
| 350 | P2T/A49G/I267V/ R276W | g231a/t322c/ t895c | | | ≥1.0 |
| 351 | P2T/A49G/R276W | | K259S | | ≥1.0 |
| 352 | P2T/A49G/K132N/ G227D/R276W | a478c/g480t/ t753g/a756t/ a853t/g854c/ c855g | | | ≥1.0 |
| 353 | P2T/A49G/I267V/ R276W | g156a/t747c/ t751a/c752g/ t753c | | | ≥1.0 |
| 354 | P2T/A49G/S233V/ I267V/R276W | g156a/g231a/ t322c/ g456a/t895c | | | ≥1.0 |
| 355 | P2T/A49G/G227D/ P252C/R276W | t753g/a853t/ g854c/c855g | | | ≥1.0 |
| 356 | P2T/A49G/R276W | | K352G | | ≥1.0 |
| 357 | P2T/A49G/R276W | a853t/g854c/ c855g | | | ≥1.0 |
| 358 | P2T/K132N/K152E/ R276W | | E235K | | ≥1.0 |
| 359 | P2T/A49G/K52R/ R206S/I267V/R276W | t9c/t84a/ g231a/t697a/ c698g/t895c | | | ≥1.0 |
| 360 | P2T/A49G/K132N/ R276W | | | | ≥1.0 |
| 361 | P2T/A49G/R276W | | K352E | | ≥1.0 |
| 362 | P2T/A49G/K52R/ R276W | t99a | | | ≥1.0 |
| 363 | P2T/A49G/R276W | | H112A | | ≥1.0 |
| 364 | P2T/A49G/S233V/ R276W | t895c | | | ≥1.0 |
| 365 | P2T/R206S/R276W | | E235K | | ≥1.0 |
| 366 | P2T/A49G/R276W | t99a/g156a/ g204a | | | ≥1.0 |
| 367 | P2T/A49G/R276W | | S26A | | ≥1.0 |
| 368 | P2T/A49G/R276W | | D210A | | ≥1.0 |
| 369 | P2T/A49G/R206S/ R276W | | K352E | | ≥1.0 |
| 370 | P2T/A49G/R276W | t618c/t697a/ c698g/c801t/ t895c | | | ≥1.0 |
| 371 | P2T/A49G/S233V/ I267V/R276W | a504g/t895c | | | ≥1.0 |
| 372 | P2T/W20X/A49G/ D63X/R276W | c111n/c822t/ a825c/a853t/ g854c/c855g | | | ≥1.0 |
| 373 | P2T/A49G/R276W | t84a | | | ≥1.0 |
| 374 | P2T/A49G/R276W | g204a/c801t | | | ≥1.0 |
| 375 | P2T/A49G/R276W | t552g/c801t/t895c | | | ≥1.0 |
| 376 | P2T/A49G/R276W | c801t | | | ≥1.0 |

The sequences of some variants included in the above table(s) are provided below. Variant 3 has active substitutions in both the XR and XD (R276F and F209S/N211K, respectively), as well as XR silent mutations (t811a/c812g/c816t), as shown in SEQ ID NOS:50 and 51 (XR DNA and amino acid sequences, respectively), and SEQ ID NOS:52 and 53 (XD DNA and amino acid sequences, respectively).

```
                                                      (SEQ ID NO: 50)
ATGCCTTCTATTAAGTTGAACTCTGGTTACGACATGCCAGCCGTCGGTTTCGGCTGTTGGAAA

GTTGACGTTGACACCTGTTCTGAACAGGTCTACCGTGCTATCAAGACCGGTTACAGATTGTT

CGACGGTGCCGAAGATTACGCCAACGAAAAGTTAGTTGGTGCCGGTGTCAAGAAGGCCATT

GACGAAGGTATCGTCAAGCGTGAAGACTTGTTCCTTACCTCCAAGTTGTGGAACAACTACCA

CCACCCAGACAACGTCGAAAAGGCCTTGAACAGAACCCTTTCTGACTTGCAAGTTGACTACG

TTGACTTGTTCTTGATCCACTTCCCAGTCACCTTCAAGTTCGTTCCATTAGAAGAAAAGTACC

CACCAGGATTCTACTGTGGTAAGGGTGACAACTTCGACTACGAAGATGTTCCAATTTTAGAG

ACCTGGAAGGCTCTTGAAAAGTTGGTCAAGGCCGGTAAGATCAGGTCTATCGGTGTTTCTAA

CTTCCCAGGTGCTTTGCTCTTGGACTTGTTGAGAGGTGCTACCATCAAGCCATCTGTCTTGCA

AGTTGAACACCACCCATACTTGCAACAACCAAGATTGATCGAGTTCGCTCAATCCCGTGGTA

TTGCTGTCACCGCTTACTCTTCGTTCGGTCCTCAATCTTTCGTTGAATTGAACCAAGGTAGAG

CTTTGAACACTTCTCCATTGTTCGAGAACGAAACTATCAAGGCTATCGCTGCTAAGCACGGT

AAGTCTCCAGCTCAAGTCTTGTTGAGATGGTCTTCCCAAAGAGGCATTGCCATCATTCCAAA

GAGCAATACTGTCCCATTCTTGTTGGAAAACAAGGATGTCAACAGCTTCGACTTGGACGAAC

AAGATTTCGCTGACATTGCCAAGTTGGACATCAACTTGAGATTCAACGACCCATGGGACTGG

GACAAGATTCCTATCTTCGTCTAA
                                                      (SEQ ID NO: 51)
MPSIKLNSGYDMPAVGFGCWKVDVDTCSEQVYRAIKTGYRLFDGAEDYANEKLVGAGVKKAI

DEGIVKREDLFLTSKLWNNYHHPDNVEKALNRTLSDLQVDYVDLFLIHFPVTFKFVPLEEKYPPG

FYCGKGDNFDYEDVPILETWKALEKLVKAGKIRSIGVSNFPGALLLDLLRGATIKPSVLQVEHHP

YLQQPRLIEFAQSRGIAVTAYSSFGPQSFVELNQGRALNTSPLFENETIKAIAAKHGKSPAQVLLR

WSSQRGIAIIPKSNTVPFLLENKDVNSFDLDEQDFADIAKLDINLRFNDPWDWDKIPIFV
                                                      (SEQ ID NO: 52)
ATGACCGCTAATCCCTCTCTTGTTTTGAATAAGATTGACGACATTTCTTTTGAAACTTACGAT

GCTCCCGAAATTAGCGAACCCACAGACGTTTTAGTTCAAGTTAAAAAAACTGGTATCTGCGG

TTCTGACATCCACTTCTACGCTCATGGAAGGATCGGCAACTTCGTCTTAACAAAGCCAATGG

TTCTGGGTCATGAAAGCGCGGGTACTGTTGTTCAAGTCGGTAAAGGTGTTACTTCACTGAAG

GTTGGTGATAACGTCGCAATCGAGCCCGGTATTCCATCTAGGTTCAGTGATGAGTACAAATC

TGGTCACTACAACCTGTGTCCACACATGGCATTTGCTGCTACTCCCAATTCTAAAGAGGGTG

AACCAAACCCACCAGGAACTCTATGTAAGTACTTCAAATCTCCAGAAGACTTCCTGGTTAAG

TTACCCGATCATGTTTCTTTGGAGTTGGGTGCTTTGGTCGAGCCACTATCTGTTGGGGTCCAT

GCTAGTAAATTAGGCTCCGTTGCATTTGGCGATTACGTTGCTGTTTTTGGTGCTGGTCCAGTA

GGATTACTGGCTGCCGCTGTCGCTAAGACATTTGGTGCCAAGGGTGTGATTGTCGTTGATAT

ATCTGACAAGAAGCTGAAGATGGCCAAAGACATAGGTGCCGCTACACATACCTTCAACTCC

AAGACGGGAGGTAGTGAAGAATTGATCAAAGCCTTCGGTGGTAATGTACCAAATGTTGTCTT

GGAATGTACTGGGGCTGAACCATGTATTAAGCTAGGTGTTGATGCCATCGCACCAGGTGGTA

GATTCGTGCAAGTTGGTAATGCTGCTGGTCCCGTGTCCTTTCCCATAACAGTGTTCGCTATGA

AAGAACTTACTTTGTTTGGTTCATTTCGTTATGGTTTCAACGACTATAAGACAGCCGTGGGTA
```

-continued
```
TCTTTGATACTAACTACCAGAACGGTAGAGAATGCTCCCATTGACTTTGAACAGCTTATC

ACGCACAGATACAAATTCAAAGACGCCATTGAAGCCTACGACCTAGTAAGAGCAGGTAAAG

GGGCTGTCAAGTGTTTGATTGATGGTCCAGAATAA
```

```
                                                   (SEQ ID NO: 53)
MTANPSLVLNKIDDISFETYDAPEISEPTDVLVQVKKTGICGSDIHFYAHGRIGNFVLTKPMVLGH

ESAGTVVQVGKGVTSLKVGDNVAIEPGIPSRFSDEYKSGHYNLCIRMAFAATPNSKEGEPNPPGT

LCKYFKSPEDFLVKLPDHVSLELGALVEPLSVGVHASKLGSVAFGDYVAVFGAGPVGLLAAAV

AKTFGAKGVIVVDISDKIKIRMAKDIGAATHTFNSKTGGSEELIKAFGGNVPNVVLECTGAEPCIK

LGVDAIAPGGRFVQVGNAAGPVSFPITVFAMKELTLFGSFRYGFNDYKTAVGIFDTNYQNGREN

APIDFEQLITHRYKFKDAIEAYDLVRAGKGAVKCLIDGPE
```

The DNA and amino acid sequences of variant 152 (P2T/A49G/R276W in XR) are provided below (SEQ ID NOS:54 and 55).

```
                                                   (SEQ ID NO: 54)
ATGACCTCTATTAAGTTGAACTCTGGTTACGACATGCCAGCCGTCGGTTTCGGCTGTTGGAA

AGTTGACGTTGACACCTGTTCTGAACAGGTCTACCGTGCTATCAAGACCGGTTACAGATTGT

TCGACGGTGCCGAAGATTACGGCAACGAAAAGTTAGTTGGTGCCGGTGTCAAGAAGGCCAT

TGACGAAGGTATCGTCAAGCGTGAAGACTTGTTCCTTACCTCCAAGTTGTGGAACAACTACC

ACCACCCAGACAACGTCGAAAAGGCCTTGAACAGAACCCTTTCTGACTTGCAAGTTGACTAC

GTTGACTTGTTCTTGATCCACTTCCCAGTCACCTTCAAGTTCGTTCCATTAGAAGAAAAGTAC

CCACCAGGATTCTACTGTGGTAAGGGTGACAACTTCGACTACGAAGATGTTCCAATTTTAGA

GACCTGGAAGGCTCTTGAAAAGTTGGTCAAGGCCGGTAAGATCAGGTCTATCGGTGTTTCTA

ACTTCCCAGGTGCTTTGCTCTTGGACTTGTTGAGAGGTGCTACCATCAAGCCATCTGTCTTGC

AAGTTGAACACCACCCATACTTGCAACAACCAAGATTGATCGAGTTCGCTCAATCCCGTGGT

ATTGCTGTCACCGCTTACTCTTCGTTCGGTCCTCAATCTTTCGTTGAATTGAACCAAGGTAGA

GCTTTGAACACTTCTCCATTGTTCGAGAACGAAACTATCAAGGCTATCGCTGCTAAGCACGG

TAAGTCTCCAGCTCAAGTCTTGTTGAGATGGTCTTCCCAAAGAGGCATTGCCATCATTCCAA

AGTCCAACACTGTCCCATGGTTGTTGGAAAACAAGGATGTCAACAGCTTCGACTTGGACGAA

CAAGATTTCGCTGACATTGCCAAGTTGGACATCAACTTGAGATTCAACGACCCATGGGACTG

GGACAAGATTCCTATCTTCGTCTAA
```

```
                                                   (SEQ ID NO: 55)
MTSIKLNSGYDWAVGFGCWKVDVDTCSEQVYRAIKTGYRLFDGAEDYGNEKLVGAGVKKAI

DEGIVKREDLFLTSKLWNNYIIHPDNVEKALNRTLSDLQVDYVDLFLEIFINTFKFVPLEEKYPPG

FYCGKGDNFDYEDVPILETWKALEKLVKAGKIRSIGVSNFPGALLLDLLRGATIKPSVLQVEHHP

YLQQPRLIEFAQSRGIAVTAYSSFGPQSFVELNQGRALNTSPLFENETIKAIAAKHGKSPAQVLLR

WSSQRGIAIIPKSNTVPWLLENKDVNSFDLDEQDFADIAKLDINLRFNDPWDWDKIPIFV
```

The DNA and amino acid sequences of variant 272 (P2T/A49G/K132N/S233K/I267V/R276W in XR) are provided below (SEQ ID NOS:56 and 57).

```
                                                   (SEQ ID NO: 56)
ATGACCTCTATTAAGTTGAACTCTGGTTACGACATGCCAGCCGTCGGTTTCGGCTGTTGGAA

AGTTGACGTTGACACCTGTTCTGAACAGGTCTACCGAGCTATCAAGACCGGTTACAGATTGT

TCGACGGTGCCGAAGATTACGGCAACGAAAAATTAGTTGGTGCCGGTGTCAAGAAGGCCAT
```

```
TGACGAAGGTATCGTCAAGCGTGAAGACTTGTTCCTTACCTCCAAGTTGTGGAACAACTACC

ACCACCCAGACAACGTCGAAAAGGCCTTGAACAGAACCCTTTCTGACTTGCAAGTTGACTAC

GTTGACTTGTTCTTGATCCACTTCCCAGTCACCTTCAAGTTCGTTCCATTAGAAGAAAGTAC

CCACCAGGATTCTACTGTGGTAACGGTGACAACTTCGACTACGAAGATGTTCCAATTTTAGA

GACCTGGAAGGCTCTTGAAAAGTTGGTCAAGGCCGGTAAGATCAGGTCTATCGGTGTTTCTA

ACTTCCCAGGTGCTTTGCTCTTGGACTTGTTGAGAGGTGCTACCATCAAGCCATCTGTCTTGC

AAGTTGAACACCACCCATACTTGCAACAACCAAGATTGATCGAGTTCGCTCAATCCCGTGGT

ATTGCTGTCACCGCTTACTCTTCGTTCGGTCCTCAATCTTTCGTTGAATTGAACCAAGGTAGA

GCTTTGAACACTAAGCCATTGTTCGAGAACGAAACTATCAAGGCTATCGCTGCTAAGCACGG

CAAGAGCCCAGCTCAAGTCTTGTTGAGATGGTCTTCCCAAAGAGGCATTGCCGTTATTCCAA

AGTCCAACACTGTCCCATGGTTGTTGGAAAACAAGGATGTCAACAGCTTCGACTTGGACGAA

CAAGATTTCGCTGACATTGCCAAGTTGGACATCAACTTGAGATTCAACGACCCATGGGACTG

GGACAAGATTCCTATCTTCGTCTAA
```

```
                                                    (SEQ ID NO: 57)
MTSIKLNSGYDMPAVGFGCWKVDVDTCSEQVYRAIKTGYRLFDGAEDYGNEKLVGAGVKKAI

DEGIVKREDLFLTSKLWNNYHHPDNVEKALNRTLSDLQVDYVDLFLIFIFPVTFKFVPLEEKYPPG

FYCGNGDNFDYEDVPILETWKALEKLVKAGKIRSIGVSNFPGALLLDLLRGATIKPSVLQVEHHP

YLQQPRLIEFAQSRGIAVTAYSSFGPQSFVELNQGRALNTKPLFENETIKAIAAKHGKSPAQVLLR

WSSQRGIAVIPKSNTVPWLLENKDVNSFDLDEQDFADIAKLDINLRFNDPWDWDKIPIFV
```

The DNA and amino acid sequences of variant 377 (P2T/E46C/A49G/F107Y/K132N/S233K/I267V/R276W in XR) are provided below (SEQ ID NOS:58 and 59).

```
                                                    (SEQ ID NO: 58)
ATGACCTCTATTAAGTTGAACTCTGGTTACGACATGCCAGCCGTCGGTTTCGGCTGTTGGAA

AGTTGACGTTGACACCTGTTCTGAACAGGTCTACCGAGCTATCAAGACCGGTTACAGATTGT

TCGACGGTGCCGAAGATTACGGCAACGAAAAATTAGTTGGTGCCGGTGTCAAGAAGGCCAT

TGACGAAGGTATCGTCAAGCGTGAAGACTTGTTCCTTACCTCCAAGTTGTGGAACAACTACC

ACCACCCAGACAACGTCGAAAAGGCCTTGAACAGAACCCTTTCTGACTTGCAAGTTGACTAC

GTTGACTTGTTCTTGATCCACTTCCCAGTCACCTTCAAGTTCGTTCCATTAGAAGAAAGTAC

CCACCAGGATTCTACTGTGGTAACGGTGACAACTTCGACTACGAAGATGTTCCAATTTTAGA

GACCTGGAAGGCTCTTGAAAAGTTGGTCAAGGCCGGTAAGATCAGGTCTATCGGTGTTTCTA

ACTTCCCAGGTGCTTTGCTCTTGGACTTGTTGAGAGGTGCTACCATCAAGCCATCTGTCTTGC

AAGTTGAACACCACCCATACTTGCAACAACCAAGATTGATCGAGTTCGCTCAATCCCGTGGT

ATTGCTGTCACCGCTTACTCTTCGTTCGGTCCTCAATCTTTCGTTGAATTGAACCAAGGTAGA

GCTTTGAACACTAAGCCATTGTTCGAGAACGAAACTATCAAGGCTATCGCTGCTAAGCACGG

CAAGAGCCCAGCTCAAGTCTTGTTGAGATGGTCTTCCCAAAGAGGCATTGCCGTTATTCCAA

AGTCCAACACTGTCCCATGGTTGTTGGAAAACAAGGATGTCAACAGCTTCGACTTGGACGAA

CAAGATTTCGCTGACATTGCCAAGTTGGACATCAACTTGAGATTCAACGACCCATGGGACTG

GGACAAGATTCCTATCTTCGTCTAA
```

```
                                                    (SEQ ID NO: 59)
MTSIKLNSGYDMPAVGFGCWKVDVDTCSEQVYRAIKTGYRLFDGAEDYGNEKLVGAGVKKAI

DEGIVKREDLFLTSKLWNNYEMPDNVEKALNRTLSDLQVDYVDLFLIHFPVTFKFVPLEEKYPPG
```

-continued

FYCGNGDNFDYEDVPILETWKALEKLVKAGKIRSIGVSNFPGALLLDLLRGATIKPSVLQVEHHP

YLQQPRLIEFAQSRGIAVTAYSSFGPQSFVELNQGRALNTKPLFENETIKAIAAKHGKSPAQVLLR

WSSQRGIAVIPKSNTVPWLLENKDVNSFDLDEQDFADIAKLDINLRFNDPWDWDKIPIFV

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of the present invention.

We claim:

1. An isolated xylose reductase variant, wherein said variant has xylose reductase activity and comprises a substitution at at least two positions selected from 271, 272, 275, 276, and 279, in SEQ ID NO:2.

2. An isolated xylose reductase variant of claim 1, wherein said variant has xylose reductase activity and comprises a substitution at at least two positions selected from S271G, N272P, P275A, R276M, R276F, R276W, and E279Q, in SEQ ID NO:2.

3. An isolated xylose reductase variant of claim 1, wherein said variant has xylose reductase activity and comprises at least one of the following substitutions or substitution sets P2T/S3H/A49G/P168S/S233K/R276W; P2T/S3X/A49G/S233X/I267X/R276W/L299X; P2T/C19L/E46C/A49G/F107Y/K132N/S233K/I267V/R276W; P2T/C19L/E46C/A49G/K132N/S233K/I267V/R276W; P2T/W20X/A49G/D63X/R276W; P2T/V24G/A49G/R276W; P2T/V24G/R276W/V318C; P2T/K36Q/A49G/G227D/R276W; P2T/E46C/A49G/F107Y/K132N/S233K/I267V/R276W; P2T/E46C/A49G/K132N/V164I/S233K/I267V/R276W; P2T/A49G/K52R/K152E/S233K/I267V/R276W; P2T/A49G/K52R/R206S/I267V/R276W; P2T/A49G/K52R/R276W; P2T/A49G/K68G/S261N/R276W/V318C; P2T/A49G/D86N/K132N/R276W; P2T/A49G/K132N/P168S/S233K/I267V/R276W; P2T/A49G/K132N/G227D/P252C/R276W; P2T/A49G/K132N/G227D/R276W; P2T/A49G/K132N/S233K/I267V/R276W; P2T/A49G/K132N/S233K/R276W; P2T/A49G/K132N/I267V/R276W; P2T/A49G/K132N/R276W; P2T/A49G/K152E/P168S/S233V/I267V/R276W; P2T/A49G/K152E/I267V/R276W; P2T/A49G/K152E/R276W; P2T/A49G/P 168 S/R206S/I267V/R276W; P2T/A49G/P168S/S233K/R276W; P2T/A49G/P168S/R276W; P2T/A49G/R206S/S233K/I267V/R276W; S233V/R276W P2T/A49G/R206S/R276W; P2T/A49G/G227D/P252C/G264D/R276W; P2T/A49G/G227D/P252C/R276W; P2T/A49G/G227D/I267V/R276W; P2T/A49G/G227D/R276W; P2T/A49G/S233K/R276W; P2T/A49G/S233K/I267V/R276W; P2T/A49G/S233V/A246L/R276W/N302S; P2T/A49G/S233V/I267V/R276W; P2T/A49G/S233V/R276W; P2T/A49G/P252C/R276W; P2T/A49G/S261N/R276W; P2T/A49G/I267V/R276W; P2T/A49G/R276W; P2T/A46G/R276W/N3025; P2T/A49G/R276W/V318C; P2T/K132A/R276W; P2T/K132N/R276W; P2T/K132N/K152E/R276W;

P2T/G157R/R276W; P2T/P168S/R276W; P2T/R206S/R276W; P2T/A246L/R276W; P2T/R276W; P2T/R276W/V318C; S3H/R33L/A56E/R276W; S3H/R33L/T114S/R276W; S3H/T114S/R276W/N302S; S3H/R276W; D11K/K155Y/R206S/R276W; D11K/V255I/R276M; D11K/R276W; R33L/A56E/R276W; R33L/R276W; K36Q/R276W; A49G/K132A/K152E/R276W; A49G/K132A/R276W; A49G/K132A/R206S/R276W; A49G/K132N/K152E/R276W; A49G/K132N/K152E/R276W/N302S; A49G/K132N/R206S/S233V/W276M/N302S; A49G/K132N/R206S/S233V/R276M/N302S; A49G/K152E/R276W; D11K/V255I/W276M; A49G/R276W; K52R/R276W; A56E/T114S/R276W; T114S/R276W; K132N/R276W; K132N/K155R/R276W/V283H; K155R/R206S/R276W; P168S/R276W; G227D/R276W; P252C/R276W; K270R/N272P/R276F; N272P/R276F; or R276W/V318C, in SEQ ID NO:2.

4. The isolated xylose reductase variant of claim 1, wherein, said variant comprises the polypeptide sequence of SEQ ID NOS:41, 43, 45, or 47.

\* \* \* \* \*

SEQUENCE LISTING

<160> NUMBER OF SEQ ID NOS: 59

<210> SEQ ID NO 1
<211> LENGTH: 960
<212> TYPE: DNA
<213> ORGANISM: Pichia stipitis

<400> SEQUENCE: 1

```
atgccttcta ttaagttgaa ctctggttac gacatgccag ccgtcggttt cggctgttgg      60
aaagtcgacg tcgacacctg ttctgaacag atctaccgtg ctatcaagac cggttacaga     120
ttgttcgacg gtgccgaaga ttacgccaac gaaaagttag ttggtgccgg tgtcaagaag     180
gccattgacg aaggtatcgt caagcgtgaa gacttgttcc ttacctccaa gttgtggaac     240
aactaccacc acccagacaa cgtcgaaaag gccttgaaca gaacccttc  tgacttgcaa     300 gttgactacg ttgacttgtt cttgatccac ttcccagtca ccttcaagtt cgttccatta     360
gaagaaaagt acccaccagg attctactgt ggtaagggtg acaacttcga ctacgaagat     420
gttccaattt tagagacctg gaaggctctt gaaaagttgg tcaaggccgg taagatcaga     480
tctatcggtg tttctaactt cccaggtgct tgctcttgg  acttgttgag aggtgctacc     540
atcaagccat ctgtcttgca agttgaacac cacccatact gcaacaacc  aagattgatc     600 gaattcgctc aatcccgtgg tattgctgtc accgcttact cttcgttcgg tcctcaatct     660
ttcgttgaat tgaaccaagg tagagctttg aacacttctc cattgttcga gaacgaaact     720
atcaaggcta tcgctgctaa gcacggtaag tctccagctc aagtcttgtt gagatggtct     780
tcccaaagag gcattgccat cattccaaag tccaacactg tcccaagatt gttggaaaac     840
aaggacgtca acagcttcga cttggacgaa caagatttcg ctgacattgc caagttggac     900
atcaacttga gattcaacga cccatgggac tgggacaaga ttcctatctt cgtctaataa     960
```

<210> SEQ ID NO 2
<211> LENGTH: 318
<212> TYPE: PRT
<213> ORGANISM: Pichia stipitis

<400> SEQUENCE: 2

```
Met Pro Ser Ile Lys Leu Asn Ser Gly Tyr Asp Met Pro Ala Val Gly
1               5                   10                  15
```

Phe Gly Cys Trp Lys Val Asp Val Asp Thr Cys Ser Glu Gln Ile Tyr
                20                  25                  30

Arg Ala Ile Lys Thr Gly Tyr Arg Leu Phe Asp Gly Ala Glu Asp Tyr
            35                  40                  45

Ala Asn Glu Lys Leu Val Gly Ala Gly Val Lys Lys Ala Ile Asp Glu
        50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315

<210> SEQ ID NO 3
<211> LENGTH: 960
<212> TYPE: DNA
<213> ORGANISM: Artificial sequence
<220> FEATURE:
<223> OTHER INFORMATION: Synthetic DNA which is codon optimized DNA
      sequence of xylose reductase from P. stipitis having sequence name
      XR.2

<400> SEQUENCE: 3
atgccctcca taaagctaaa ctctggttat gatatgcctg ccgttggatt cggttgttgg      60
aaagtagatg ttgatacctg ctcagaacag atttataggg ctattaaaac aggttacagg     120
ttgttcgacg gtgccgagga ctacgcgaat gagaagttag ttggagctgg tgttaagaag     180
gccatcgacg agggcattgt taagagggag gacctgttct taacgtctaa actgtggaat     240
aactatcacc acccagacaa tgttgaaaaa gccctgaata gaactttgag tgatttgcag     300

-continued

```
gtggattacg ttgacttgtt tctaatccat ttccccgtta ctttcaagtt cgtccctta      360 gaggagaagt atccaccagg tttctattgt ggtaagggcg acaacttcga ctatgaagat      420
gttcctattc tggagacctg gaaggctctg gagaaactgg tcaaggcagg caaataagg      480 tccataggcg tctctaactt cccaggagca ctactgcttg acttgttgag gggagctacc      540
atcaaacctt cagtcttgca agttgaacac caccccctatt tgcaacaacc caggctgata      600
gagtttgctc aatccagagg tatagctgtt actgcatact cttcctttgg acctcaatcc      660
ttcgtcgaac ttaaccaagg tagagcgttg aatacttccc ccttgttcga gaatgaaact      720
atcaaggcta ttgcggctaa gcacggtaag tcaccagctc aagtgttact tagatggtct      780
tcccaaaggg gtatcgcaat cattccaaag tctaacactg ttcccagatt gttggagaat      840
aaagatgtta attctttcga tttggacgaa caagactttg cagacatagc caaactagat      900
attaatctga gattcaatga tccctgggat tgggacaaga taccaatctt cgtttaataa      960
```

<210> SEQ ID NO 4
<211> LENGTH: 942
<212> TYPE: DNA
<213> ORGANISM: Artificial sequence
<220> FEATURE:
<223> OTHER INFORMATION: Synthetic DNA which is codon optimized DNA
      sequence of xylose reductase from P. stipitis having sequence name
      XR.3

<400> SEQUENCE: 4

```
atgccatcta ttaagttgaa ctctggttac gacatgccag ctgtcggttt cggttgtaag      60
gttgacgttg acacctgttc tgaacaaatt tacagagcta ttaagaccgg ttacagattg      120
ttcgacggtg ctgaagacta cgctaacgaa aagttggttg gtgctggtgt caagaaggct      180
attgacgaag gtattgtcaa gagagaagac ttgttcttga cctctaagtt gaacaactac      240
caccacccag acaacgtcga aaaggctttg aacagaacct gtctgacttg caagttgac      300 tacgttgact tgttcttgat tcacttccca gtcaccttca gttcgtccc attggaagaa      360 aagtacccac aggttttcta ctgtggtaag ggtgacaact tcgactacga agacgttcca      420
attttggaaa ccaaggcttt ggaaaagttg gttaaggctg gtaagattag gtctattggt      480
gtttctaact tcccaggtgc tttgttgttg gacttgttga gggtgctac cattaagcca      540 tctgttttgc aagttgaaca ccacccatac ttgcaacaac caagattgat tgagttcgct      600
caatctaggg gtattgctgt caccgcttac tcttctttcg gtccacaatc tttcgtcgaa      660
ttgaaccaag gtagagcttt gaacacctct ccattgttcg aaaacgaaac cattaaggct      720
attgctgcta agcacggtaa gtctccagct caagtcttgt tgaggtcttc tcaaagaggt      780
attgctatta ttccaaagtc taacaccgtc caagattgt tggaaaacaa ggacgttaac      840
tctttcgact ggacgaaca agacttcgct gacattgcta agttggacat taacttgaga      900
ttcaacgacc cagacgacaa gattccaatt ttcgtttaat aa                          942
```

<210> SEQ ID NO 5
<211> LENGTH: 1095
<212> TYPE: DNA
<213> ORGANISM: Pichia stipitis

<400> SEQUENCE: 5

```
atgactgcta acccttcctt ggtgttgaac aagatcgacg acatttcgtt cgaaacttac      60
gatgccccag aaatctctga acctaccgat gtcctcgtcc aggtcaagaa aaccggtatc      120
tgtggttccg acatccactt ctacgcccat ggtagaatcg gtaacttcgt tttgaccaag      180
```

```
ccaatggtct tgggtcacga atccgccggt actgttgtcc aggttggtaa gggtgtcacc      240
tctcttaagg ttggtgacaa cgtcgctatc gaaccaggta ttccatccag attctccgac      300
gaatacaaga gcggtcacta caacttgtgt cctcacatgg ccttcgccgc tactcctaac      360
tccaaggaag gcgaaccaaa cccaccaggt accttatgta agtacttcaa gtcgccagaa      420
gacttcttgg tcaagttgcc agaccacgtc agcttggaac tcggtgctct tgttgagcca      480
ttgtctgttg gtgtccacgc tctaagttg ggttccgttg ctttcggcga ctacgttgcc       540
gtctttggtg ctggtcctgt tggtcttttg gctgctgctg tcgccaagac cttcggtgct      600
aagggtgtca tcgtcgttga catttcgac aacaagttga gatggccaa ggacattggt        660 gctgctactc acaccttcaa ctccaagacc ggtggttctg aagaattgat caaggctttc      720
ggtggtaacg tgccaaacgt cgtttttggaa tgtactggtg ctgaaccttg tatcaagttg     780
ggtgttgacg ccattgcccc aggtggtcgt ttcgttcaag tcggtaacgc tgctggtcca      840
gtcagcttcc caatcaccgt tttcgccatg aaggaattga ctttgttcgg ttctttcaga      900
tacggattca acgactacaa gactgctgtt ggaatctttg acactaacta ccaaaacggt      960
agagaaaatg ctccaattga ctttgaacaa ttgatcaccc acagatacaa gttcaaggac     1020
gctattgaag cctacgactt ggtcagagcc ggtaagggtg ctgtcaagtg tctcattgac     1080
ggccctgagt aataa                                                      1095

<210> SEQ ID NO 6
<211> LENGTH: 363
<212> TYPE: PRT
<213> ORGANISM: Pichia stipitis

<400> SEQUENCE: 6

Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
```

```
           210                 215                 220
Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
                260                 265                 270

Gln Val Gly Asn Ala Ala Gly Pro Val Ser Phe Pro Ile Thr Val Phe
            275                 280                 285

Ala Met Lys Glu Leu Thr Leu Phe Gly Ser Phe Arg Tyr Gly Phe Asn
        290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
                340                 345                 350

Gly Ala Val Lys Cys Leu Ile Asp Gly Pro Glu
            355                 360
```

<210> SEQ ID NO 7
<211> LENGTH: 1095
<212> TYPE: DNA
<213> ORGANISM: Artificial sequence
<220> FEATURE:
<223> OTHER INFORMATION: Synthetic DNA which is codon optimized DNA
      sequence of xylitol dehydrogenase from P. stipitis having
      sequence name XD.2

<400> SEQUENCE: 7

```
atgaccgcta atccctctct tgttttgaat aagattgacg acatttcttt tgaaacttac      60 gatgctccg aaattagcga acccacagac gttttagttc aagttaaaaa aactggtatc      120
tgcggttctg acatccactt ctacgctcat ggaaggatcg gcaacttcgt cttaacaaag     180
ccaatggttc tgggtcatga agcgcgggt actgttgttc aagtcggtaa aggtgttact     240
tcactgaagg ttggtgataa cgtcgcaatc gagcccggta ttccatctag gttcagtgat     300
gagtacaaat ctggtcacta caacctgtgt ccacacatgg catttgctgc tactcccaat     360
tctaaagagg gtgaaccaaa cccaccagga actctatgta agtacttcaa atctccagaa     420
gacttcctgg ttaagttacc cgatcatgtt tctttggagt tgggtgcttt ggtcgagcca     480
ctatctgttg gggtccatgc tagtaaatta ggctccgttg catttggcga ttacgttgct     540
gtttttggtg ctggtccagt aggattactg gctgccgctg tcgctaagac atttggtgcc     600
aagggtgtga ttgtcgttga tatatttgac aacaagctga agatggccaa agacataggt     660
gccgctacac ataccttcaa ctccaagacg ggaggtagtg aagaattgat caaagccttc     720
ggtggtaatg taccaaatgt tgtcttggaa tgtactgggg ctgaaccatg tattaagcta     780
ggtgttgatg ccatcgcacc aggtggtaga ttcgtgcaag ttggtaatgc tgctggtccc     840
gtgtcctttc ccataacagt gttcgctatg aaagaactta ctttgtttgg ttcatttcgt     900
tatggtttca cgactataa dacagccgtg gtatctttg atactaacta ccagaacggt     960
agagagaatg ctcccattga ctttgaacag cttatcacgc acagatacaa attcaaagac    1020
gccattgaag cctacgacct agtaagagca ggtaaggggg ctgtcaagtg tttgattgat    1080
ggtccagaat aataa                                                      1095
```

| <210> SEQ ID NO 8
| <211> LENGTH: 1095
| <212> TYPE: DNA
| <213> ORGANISM: Artificial sequence
| <220> FEATURE:
| <223> OTHER INFORMATION: Synthetic DNA which is codon optimized DNA
|       sequence of xylitol dehydrogenase from P. stipitis having
|       sequence name XD.3

<400> SEQUENCE: 8

```
atgaccgcta acccatcttt ggtcttgaac aagattgacg acatttcttt cgaaacctac      60
gacgctccag aaatttctga accaaccgac gttttggttc aagtcaagaa gaccggtatt     120
tgtggttctg acattcactt ctacgctcac ggtagaattg gtaacttcgt cttgaccaag     180
ccaatggtct tgggtcacga atctgctggt accgttgttc aagtcggtaa gggtgtcacc     240
tctttgaagg tcggtgacaa cgtcgctatt gaaccaggta ttccaagtag attctctgac     300
gaatacaagt ctggtcacta caacttgtgt ccacacatgg ctttcgctgc taccccaaac     360
tctaaggaag gtgaaccaaa cccaccaggt accttgtgta agtacttcaa gtctccagaa     420
gacttcttgg ttaagttgcc agaccacgtt tctttggaat gggtgctttt ggttgaacca     480
ttgtctgttg gtgttcacgc ttctaagttg ggttctgttg ctttcggtga ctacgttgct     540
gttttcggtg ctggtccagt tggtttgttg gctgctgctg ttgctaagac cttcggtgct     600
aagggtgtca ttgtcgttga catttttcgac aacaagttga gatggctaa ggacattggt     660 gctgctaccc acaccttcaa ctctaagacc ggtggttctg aagaattgat taaggctttc     720
ggtggtaacg tcccaaacgt cgtcttggaa tgtaccggtg ctgaaccatg tattaagttg     780
ggtgttgacg ctattgctcc aggtggtaga ttcgtccaag ttggtaacgc tgctggtcca     840
gttctttccc caattaccgt tttcgctatg aaggaattga ccttgttcgg ttctttcaga     900
tacggtttca cgactacaa gaccgctgtt ggtattttcg acaccaacta ccaaaacggt     960
agagaaaacg ctccaattga cttcgaacaa ttgattaccc acagatacaa gttcaaggac    1020
gctattgaag cttacgactt ggttagagct ggtaagggtg ctgttaagtg tttgattgac    1080
ggtccagaat aataa                                                    1095
```

| <210> SEQ ID NO 9
| <211> LENGTH: 1803
| <212> TYPE: DNA
| <213> ORGANISM: Saccharomyces cerevisiae

<400> SEQUENCE: 9

```
atgttgtgtt cagtaattca gagacagaca agagaggttt ccaacacaat gtctttagac      60
tcatactatc ttgggtttga tctttcgacc caacaactga atgtctcgc cattaaccag     120 gacctaaaaa ttgtccattc agaaacagtg gaatttgaaa aggatcttcc gcattatcac     180
acaaagaagg gtgtctatat acacggcgac actatcgaat gtcccgtagc catgtggtta     240
gaggctctag atcggttctt ctcgaaatat cgcgaggcta aatttccatt gaacaaagtt     300
atggccgtct cagggtcctg ccagcagcac gggtctgtct actggtcctc ccaagccgaa     360
tctctgttag agcaattgaa taagaaaccg gaaaaagatt tattgcacta cgtgagctct     420
gtagcatttg caaggcaaac cgcccccaat tggcaagacc acagtactgc aaagcaatgt     480
caagagtttg aagagtgcat aggtgggcct gaaaaaatgg ctcaattaac agggtccaga     540 gcccattttta gatttactgg tcctcaaatt ctgaaaattg cacaattaga accagaagct     600
tacgaaaaaa caaagaccat ttctttagtg tctaattttt tgacttctat cttagtgggc     660
catcttgttg aattagagga ggcagatgcc tgtggtatga acctttatga tatacgtgaa     720
```

```
agaaaattca gtgatgagct actacatcta attgatagtt cttctaagga taaaactatc    780
agacaaaaat taatgagagc acccatgaaa aatttgatag cgggtaccat ctgtaaatat    840
tttattgaga agtacggttt caatacaaac tgcaaggtct ctcccatgac tggggataat    900
ttagccacta tatgttcttt acccctgcgg aagaatgacg ttctcgtttc cctaggaaca    960
agtactacag ttcttctggt caccgataag tatcacccct ctccgaacta tcatcttttc   1020
attcatccaa ctctgccaaa ccattatatg ggtatgattt gttattgtaa tggttctttg   1080
gcaagggaga ggataagaga cgagttaaac aaagaacggg aaaataatta tgagaagact   1140
aacgattgga ctctttttaa tcaagctgtg ctagatgact cagaaagtag tgaaaatgaa   1200
ttaggtgtat attttcctct gggggagatc gttcctagcg taaaagccat aaacaaaagg   1260
gttatcttca atccaaaaac gggtatgatt gaaagagagg tggccaagtt caaagacaag   1320
aggcacgatg ccaaaaatat tgtagaatca caggctttaa gttgcagggt aagaatatct   1380
cccctgcttt cggattcaaa cgcaagctca aacagagac tgaacgaaga tacaatcgtg   1440
aagtttgatt acgatgaatc tccgctgcgg gactacctaa ataaaaggcc agaaaggact   1500
ttttttgtag gtggggcttc taaaaacgat gctattgtga agaagtttgc tcaagtcatt   1560
ggtgctacaa agggtaattt taggctagaa acaccaaact catgtgccct tggtggttgt   1620
tataaggcca tgtggtcatt gttatatgac tctaataaaa ttgcagttcc ttttgataaa   1680
tttctgaatg acaattttcc atggcatgta atggaaagca tatccgatgt ggataatgaa   1740
aattgggatc gctataattc caagattgtc cccttaagcg aactggaaaa gactctcatc   1800
taa                                                                 1803

<210> SEQ ID NO 10
<211> LENGTH: 600
<212> TYPE: PRT
<213> ORGANISM: Saccharomyces cerevisiae

<400> SEQUENCE: 10

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175
```

```
Thr Gly Ser Arg Ala His Phe Arg Phe Thr Gly Pro Gln Ile Leu Lys
            180                 185                 190

Ile Ala Gln Leu Glu Pro Glu Ala Tyr Glu Lys Thr Lys Thr Ile Ser
        195                 200                 205

Leu Val Ser Asn Phe Leu Thr Ser Ile Leu Val Gly His Leu Val Glu
    210                 215                 220

Leu Glu Glu Ala Asp Ala Cys Gly Met Asn Leu Tyr Asp Ile Arg Glu
225                 230                 235                 240

Arg Lys Phe Ser Asp Glu Leu Leu His Leu Ile Asp Ser Ser Ser Lys
                245                 250                 255

Asp Lys Thr Ile Arg Gln Lys Leu Met Arg Ala Pro Met Lys Asn Leu
            260                 265                 270

Ile Ala Gly Thr Ile Cys Lys Tyr Phe Ile Glu Lys Tyr Gly Phe Asn
        275                 280                 285

Thr Asn Cys Lys Val Ser Pro Met Thr Gly Asp Asn Leu Ala Thr Ile
    290                 295                 300

Cys Ser Leu Pro Leu Arg Lys Asn Asp Val Leu Val Ser Leu Gly Thr
305                 310                 315                 320

Ser Thr Thr Val Leu Leu Val Thr Asp Lys Tyr His Pro Ser Pro Asn
                325                 330                 335

Tyr His Leu Phe Ile His Pro Thr Leu Pro Asn His Tyr Met Gly Met
            340                 345                 350

Ile Cys Tyr Cys Asn Gly Ser Leu Ala Arg Glu Arg Ile Arg Asp Glu
        355                 360                 365

Leu Asn Lys Glu Arg Glu Asn Asn Tyr Glu Lys Thr Asn Asp Trp Thr
    370                 375                 380

Leu Phe Asn Gln Ala Val Leu Asp Asp Ser Glu Ser Ser Glu Asn Glu
385                 390                 395                 400

Leu Gly Val Tyr Phe Pro Leu Gly Glu Ile Val Pro Ser Val Lys Ala
                405                 410                 415

Ile Asn Lys Arg Val Ile Phe Asn Pro Lys Thr Gly Met Ile Glu Arg
            420                 425                 430

Glu Val Ala Lys Phe Lys Asp Lys Arg His Asp Ala Lys Asn Ile Val
        435                 440                 445

Glu Ser Gln Ala Leu Ser Cys Arg Val Arg Ile Ser Pro Leu Leu Ser
450                 455                 460

Asp Ser Asn Ala Ser Ser Gln Gln Arg Leu Asn Glu Asp Thr Ile Val
465                 470                 475                 480

Lys Phe Asp Tyr Asp Glu Ser Pro Leu Arg Asp Tyr Leu Asn Lys Arg
                485                 490                 495

Pro Glu Arg Thr Phe Phe Val Gly Gly Ala Ser Lys Asn Asp Ala Ile
            500                 505                 510

Val Lys Lys Phe Ala Gln Val Ile Gly Ala Thr Lys Gly Asn Phe Arg
        515                 520                 525

Leu Glu Thr Pro Asn Ser Cys Ala Leu Gly Gly Cys Tyr Lys Ala Met
    530                 535                 540

Trp Ser Leu Leu Tyr Asp Ser Asn Lys Ile Ala Val Pro Phe Asp Lys
545                 550                 555                 560

Phe Leu Asn Asp Asn Phe Pro Trp His Val Met Glu Ser Ile Ser Asp
                565                 570                 575

Val Asp Asn Glu Asn Trp Asp Arg Tyr Asn Ser Lys Ile Val Pro Leu
            580                 585                 590

Ser Glu Leu Glu Lys Thr Leu Ile
        595                 600
```

<210> SEQ ID NO 11
<211> LENGTH: 1806
<212> TYPE: DNA
<213> ORGANISM: Artificial sequence
<220> FEATURE:
<223> OTHER INFORMATION: Synthetic DNA which is codon optimized DNA sequence of xylulokinase from S. cerevisiae having sequence name XK.2

<400> SEQUENCE: 11

| | | | | | |
|---|---|---|---|---|---|
| atgctgtgct | ccgttataca | aaggcaaaca | agagaagtat | ccaacactat | gtctttagat | 60 |
| agttattatc | taggattcga | tttaagtaca | caacaattga | aatgtcttgc | tataaaccag | 120 |
| gatctaaaga | tcgtccattc | cgaaactgtc | gagttcgaga | aggacttacc | acattatcac | 180 |
| accaagaaag | gcgtctacat | tcatggtgac | accatcgaat | gcccagttgc | tatgtggtta | 240 |
| gaagccctgg | atcttgtcct | gtccaaatat | agggaggcaa | agttcccact | gaacaaggtc | 300 |
| atggctgttt | ccgttcttg | tcagcagcat | ggctccgtct | actggtcatc | acaggctgaa | 360 |
| tctctgttag | aacaactgaa | caagaagcca | gagaaggacc | tgttacacta | cgtctcctct | 420 |
| gttgcatttg | ccagacaaac | tgctcctaat | tggcaagacc | attccactgc | taaacaatgt | 480 |
| caggagttcg | aagagtgtat | tggtggacca | gagaaaatgg | cccagttaac | tggttcccgt | 540 |
| gctcatttca | ggttcacagg | cccacaaatc | ctgaagattg | ctcagttaga | accagaggct | 600 |
| tatgaaaaga | ctaagaccat | ctcttggtc | tctaatttct | taacttccat | tctggttggt | 660 |
| cacttggtcg | aactggaaga | agctgatgcg | tgtggtatga | acctgtacga | catccgtgag | 720 |
| aggaagttct | ctgacgaact | gctgcatctt | atcgactcct | cctctaagga | caagaccatc | 780 |
| aggcagaaac | tgatgagggc | accaatgaag | aacctgattg | ccggtactat | ttgcaagtac | 840 |
| ttcatcgaaa | agtatggctt | caacaccaac | tgcaaagtct | cccctatgac | tggcgataac | 900 |
| ctagccacca | tttgtagctt | gcccttaaga | aaaaacgatg | ttcttgtgtc | tttgggtact | 960 |
| tccacaaccg | tcttgttggt | taccgacaaa | tatcacccct | caccaaaacta | ccacctgttc | 1020 |
| atccacccga | cgttgcctaa | ccactacatg | ggcatgatct | gctactgcaa | tggcagttta | 1080 |
| gcaagggaaa | ggataaggga | cgagttgaac | aaggagaggg | agaacaacta | cgagaagacc | 1140 |
| aacgattgga | ccctgttcaa | ccaagctgtc | ctggatgata | gcgaatcctc | cgagaatgaa | 1200 |
| ctgggcgttt | actttccact | aggcgagatc | gttccatctg | tcaaggccat | caacaagaga | 1260 |
| gtaatcttca | accccaagac | tggcatgatc | gaaagggaag | tcgccaagtt | caaggacaag | 1320 |
| agacatgacg | ccaagaacat | cgttgaatct | caagccttat | cttgccgtgt | taggatttct | 1380 |
| cccctactaa | gcgactccaa | tgcttcttcc | cagcaacgtt | tgaacgagga | tacgattgtt | 1440 |
| aaattcgact | acgacgagag | tccattgaga | gactacttga | acaaacgtcc | tgagaggaca | 1500 |
| ttctttgttg | gtggcgcatc | caagaacgat | gctattgtta | agaagtttgc | tcaggtcata | 1560 |
| ggagcaacca | aaggtaactt | tcgtttagaa | actccaaact | catgcgcttt | aggtggttgc | 1620 |
| tacaaggcta | tgtggtcttt | gttgtatgat | agcaataaaa | tcgctgttcc | tttcgacaag | 1680 |
| ttcctaaacg | ataacttccc | ttggcacgtc | atggaatcca | tcagcgatgt | agacaacgag | 1740 |
| aattgggata | gatacaattc | taaaatagtt | cccttgtctg | agttagagaa | gaccttgatt | 1800 |
| taataa | | | | | 1806 |

<210> SEQ ID NO 12
<211> LENGTH: 1785
<212> TYPE: DNA
<213> ORGANISM: Artificial sequence
<220> FEATURE:
<223> OTHER INFORMATION: Synthetic DNA which is codon optimized DNA
sequence of xylulokinase from S. cerevisiae having sequence name
XK.3

<400> SEQUENCE: 12

```
atgttgtgtt ctgtcattca agacaaacc  agagaagttt ctaacaccat gtctttggac      60
tcttactact tgggtttcga cttgtctacc caacaattga agtgtttggc tattaaccaa     120
gacttgaaga ttgtccactc tgaaaccgtt gagttcgaaa aggacttgcc acactaccac     180
accaagaagg gtgtctacat tcacggtgac accattgaat gtccagtcgc tatgttggaa     240
gctttggact tggttttgtc taagtacaga gaagctaagt tcccattgaa caaggtcatg     300
gctgtctctg gttcttgtca acaacacggt tctgtctact cttctcaagc tgaatctttg     360
ttggaacaat gaacaagaa  gccagaaaag gacttgttgc actacgtctc ttctgtcgct     420
ttcgctagac aaaccgctcc aaaccaagac cactctaccg ctaagcaatg tcaagagttc     480
gaagaatgta ttggtggtcc agaaaagatg gctcaattga ccggtagtag agcacacttc     540
agattcaccg gtccacaaat tttgaagatt gctcaattgg aaccagaagc ttacgaaaag     600
accaagacca tttctttggt ctctaacttc ttgacctcta ttttggtcgg tcacttggtc     660
gaattggaag aagctgacgc ttgtggtatg aacttgtacg acattagaga agaaagttc      720
tctgacgaat tgttgcactt gattgactct tcttctaagg acaagaccat tagacaaaag     780
ttgatgaggg ctccaatgaa gaacttgatt gctggtacca tttgtaagta cttcattgaa     840
aagtacggtt tcaacaccaa ctgtaaggtc tctccaatga ccggtgacaa cttggctacc     900
atttgttctt tgccattgag aaagaacgac gttttggttt ctttgggtac tctaccacc      960
gtcttgttgg ttaccgacaa gtaccaccca tctccaaact accacttgtt cattcaccca    1020
accttgccaa accactacat gggtatgatt tgttactgta acggttcttt ggctagagaa    1080
agaattagag acgaattgaa caaggaaaga gaaacaact  acgaaaagac caacgacacc    1140
ttgttcaacc aagctgtttt ggacgactct gaatcttctg aaaacgaatt gggtgtctac    1200
ttcccattgg gtgaaattgt tccatctgtc aaggctatta acaagagagt cattttcaac    1260
ccaaagaccg gtatgattga agagaagtc  gctaagttca aggacaagag acacgacgct    1320
aagaacattg tcgaatctca agctttgtct tgtagagtta gaatttctcc attgttgtct    1380
gactctaacg cttcttctca acaaagattg aacgaagaca ccattgtcaa gttcgactac    1440
gacgaatctc cattgagaga ctacttgaac aagagaccag aaagaacctt cttcgttggt    1500
ggtgcttcta gaacgacgc  tattgttaag aagttcgctc aagtcattgg tgctaccaag    1560
ggtaacttca gattggaaac cccaaactct tgtgctttgg gtggttgtta caaggctatg    1620
tctttgttgt acgactctaa caagattgct gttccattcg acaagttctt gaacgacaac    1680
ttcccacacg tcatggaatc tatttctgac gttgacaacg aaaacgacag atacaactct    1740
aagattgttc cattgtctga attggaaaag accttgattt aataa                    1785
```

<210> SEQ ID NO 13
<211> LENGTH: 14
<212> TYPE: DNA
<213> ORGANISM: Artificial sequence
<220> FEATURE:
<223> OTHER INFORMATION: Synthetic DNA 5' flanking sequence to introduce
specific restriction enzyme sites

<400> SEQUENCE: 13

```
ggatcccaaa caaa                                                        14
```

```
<210> SEQ ID NO 14
<211> LENGTH: 6
<212> TYPE: DNA
<213> ORGANISM: Artificial sequence
<220> FEATURE:
<223> OTHER INFORMATION: Synthetic DNA 3' flanking sequence to introduce
      specific restriction enzyme sites

<400> SEQUENCE: 14 catatg                                                                     6

<210> SEQ ID NO 15
<211> LENGTH: 14
<212> TYPE: DNA
<213> ORGANISM: Artificial sequence
<220> FEATURE:
<223> OTHER INFORMATION: Synthetic DNA 5' flanking sequence to introduce
      specific restriction enzyme sites

<400> SEQUENCE: 15
actagtcaaa caaa                                                           14

<210> SEQ ID NO 16
<211> LENGTH: 6
<212> TYPE: DNA
<213> ORGANISM: Artificial sequence
<220> FEATURE:
<223> OTHER INFORMATION: Synthetic DNA 3' flanking sequence to introduce
      specific restriction enzyme sites

<400> SEQUENCE: 16 gacgtc                                                                     6

<210> SEQ ID NO 17
<211> LENGTH: 16
<212> TYPE: DNA
<213> ORGANISM: Artificial sequence
<220> FEATURE:
<223> OTHER INFORMATION: Synthetic DNA 5' flanking sequence to introduce
      specific restriction enzyme sites

<400> SEQUENCE: 17
gcggccgcca aacaaa                                                         16

<210> SEQ ID NO 18
<211> LENGTH: 6
<212> TYPE: DNA
<213> ORGANISM: Artificial sequence
<220> FEATURE:
<223> OTHER INFORMATION: Synthetic DNA 3' flanking sequence to introduce
      specific restriction enzyme sites

<400> SEQUENCE: 18 ctcgag                                                                     6

<210> SEQ ID NO 19
<211> LENGTH: 88
<212> TYPE: DNA
<213> ORGANISM: Artificial sequence
<220> FEATURE:
<223> OTHER INFORMATION: Synthetic DNA to introduce a new multiple
      cloning site

<400> SEQUENCE: 19
gagctcacgg atccgtcata tgctagatct ctgaattctt actagttcga cgtctaccta        60
ggcagtcgac acgcggccgc ttctcgag                                            88
```

```
<210> SEQ ID NO 20
<211> LENGTH: 60
<212> TYPE: DNA
<213> ORGANISM: Artificial sequence
<220> FEATURE:
<223> OTHER INFORMATION: Synthetic DNA primer

<400> SEQUENCE: 20
gcatagcaat ctaatctaag ttttggatcc gtcatatggc ggatctctta tgtctttacg      60

<210> SEQ ID NO 21
<211> LENGTH: 54
<212> TYPE: DNA
<213> ORGANISM: Artificial sequence
<220> FEATURE:
<223> OTHER INFORMATION: Synthetic DNA primer

<400> SEQUENCE: 21
ttgtatgtac ctgtctgaat tcagagatct agccctgaga aactatatga gggt            54

<210> SEQ ID NO 22
<211> LENGTH: 54
<212> TYPE: DNA
<213> ORGANISM: Artificial sequence
<220> FEATURE:
<223> OTHER INFORMATION: Synthetic DNA primer

<400> SEQUENCE: 22
accctcatat agtttctcag ggctagatct ctgaattcag acaggtacat acaa            54

<210> SEQ ID NO 23
<211> LENGTH: 62
<212> TYPE: DNA
<213> ORGANISM: Artificial sequence
<220> FEATURE:
<223> OTHER INFORMATION: Synthetic DNA primer

<400> SEQUENCE: 23
tcataaatca taagaaattc gcgacgtcga actagttgta tatgagatag ttgattgtat      60
gc                                                                    62

<210> SEQ ID NO 24
<211> LENGTH: 62
<212> TYPE: DNA
<213> ORGANISM: Artificial sequence
<220> FEATURE:
<223> OTHER INFORMATION: Synthetic DNA primer

<400> SEQUENCE: 24
gcatacaatc aactatctca tatacaacta gttcgacgtc gcgaatttct tatgatttat      60
ga                                                                    62

<210> SEQ ID NO 25
<211> LENGTH: 47
<212> TYPE: DNA
<213> ORGANISM: Artificial sequence
<220> FEATURE:
<223> OTHER INFORMATION: Synthetic DNA primer

<400> SEQUENCE: 25
tgataaactc gaagtcgact gcctaggcat gccggtagag gtgtggt                   47

<210> SEQ ID NO 26
<211> LENGTH: 47
<212> TYPE: DNA
```

<213> ORGANISM: Artificial sequence
<220> FEATURE:
<223> OTHER INFORMATION: Synthetic DNA primer

<400> SEQUENCE: 26
accacacctc taccggcatg cctaggcagt cgacttcgag tttatca                    47

<210> SEQ ID NO 27
<211> LENGTH: 58
<212> TYPE: DNA
<213> ORGANISM: Artificial sequence
<220> FEATURE:
<223> OTHER INFORMATION: Synthetic DNA primer

<400> SEQUENCE: 27
gcgtgacata actaattaca tgactcgaga agcggccgct tgtttgttt atgtgtgt        58

<210> SEQ ID NO 28
<211> LENGTH: 6
<212> TYPE: DNA
<213> ORGANISM: Artificial sequence
<220> FEATURE:
<223> OTHER INFORMATION: Synthetic DNA of sequence within the ADH2
      terminator

<400> SEQUENCE: 28 gacgtc                                                                  6

<210> SEQ ID NO 29
<211> LENGTH: 6
<212> TYPE: DNA
<213> ORGANISM: Artificial sequence
<220> FEATURE:
<223> OTHER INFORMATION: Synthetic DNA

<400> SEQUENCE: 29 gatgtc                                                                  6

<210> SEQ ID NO 30
<211> LENGTH: 67
<212> TYPE: DNA
<213> ORGANISM: Artificial sequence
<220> FEATURE:
<223> OTHER INFORMATION: Synthetic DNA primer

<400> SEQUENCE: 30
cttgctcatt agaaagaaag catagcaatc taatctaagt tttggatccc aaacaaaatg     60
ccctcca                                                                67

<210> SEQ ID NO 31
<211> LENGTH: 61
<212> TYPE: DNA
<213> ORGANISM: Artificial sequence
<220> FEATURE:
<223> OTHER INFORMATION: Synthetic DNA primer

<400> SEQUENCE: 31
ctataaatcg taaagacata agagatccgc catatgttat taaacgaaga ttggtatctt    60
g                                                                       61

<210> SEQ ID NO 32
<211> LENGTH: 61
<212> TYPE: DNA
<213> ORGANISM: Artificial sequence
<220> FEATURE:
<223> OTHER INFORMATION: Synthetic DNA primer

```
<400> SEQUENCE: 32
caagatacca atcttcgttt aataacatat ggcggatctc ttatgtcttt acgatttata      60
g                                                                     61

<210> SEQ ID NO 33
<211> LENGTH: 63
<212> TYPE: DNA
<213> ORGANISM: Artificial sequence
<220> FEATURE:
<223> OTHER INFORMATION: Synthetic DNA primer

<400> SEQUENCE: 33
gagggattag cggtcatttt gtttgactag ttgtatatga gatagttgat tgtatgcttg      60
gta                                                                   63

<210> SEQ ID NO 34
<211> LENGTH: 63
<212> TYPE: DNA
<213> ORGANISM: Artificial sequence
<220> FEATURE:
<223> OTHER INFORMATION: Synthetic DNA primer

<400> SEQUENCE: 34
taccaagcat acaatcaact atctcatata caactagtca aacaaaatga ccgctaatcc      60
ctc                                                                   63

<210> SEQ ID NO 35
<211> LENGTH: 60
<212> TYPE: DNA
<213> ORGANISM: Artificial sequence
<220> FEATURE:
<223> OTHER INFORMATION: Synthetic DNA primer

<400> SEQUENCE: 35
taataaaaat cataaatcat aagaaattcg cgacgtctta ttattctgga ccatcaatca     60

<210> SEQ ID NO 36
<211> LENGTH: 60
<212> TYPE: DNA
<213> ORGANISM: Artificial sequence
<220> FEATURE:
<223> OTHER INFORMATION: Synthetic DNA primer

<400> SEQUENCE: 36
tgattgatgg tccagaataa taagacgtcg cgaatttctt atgatttatg attttatta     60

<210> SEQ ID NO 37
<211> LENGTH: 61
<212> TYPE: DNA
<213> ORGANISM: Artificial sequence
<220> FEATURE:
<223> OTHER INFORMATION: Synthetic DNA primer

<400> SEQUENCE: 37
tttgtataac ggagcacagc attttgtttg gcggccgctt tgtttgttta tgtgtgttta     60
t                                                                    61

<210> SEQ ID NO 38
<211> LENGTH: 61
<212> TYPE: DNA
<213> ORGANISM: Artificial sequence
<220> FEATURE:
<223> OTHER INFORMATION: Synthetic DNA primer
```

<400> SEQUENCE: 38

```
ataaacacac ataaacaaac aaagcggccg ccaaacaaaa tgctgtgctc cgttatacaa      60
a                                                                     61
```

<210> SEQ ID NO 39
<211> LENGTH: 70
<212> TYPE: DNA
<213> ORGANISM: Artificial sequence
<220> FEATURE:
<223> OTHER INFORMATION: Synthetic DNA primer

<400> SEQUENCE: 39

```
ggggagggcg tgaatgtaag cgtgacataa ctaattacat gactcgagtt attaaatcaa      60
ggtcttctct                                                            70
```

<210> SEQ ID NO 40
<211> LENGTH: 957
<212> TYPE: DNA
<213> ORGANISM: Artificial sequence
<220> FEATURE:
<223> OTHER INFORMATION: Synthetic DNA

<400> SEQUENCE: 40

```
atgccttcta ttaagttgaa ctctggttac gacatgccag ccgtcggttt cggctgttgg      60
aaagttgacg ttgacacctg ttctgaacag gtctaccgtg ctatcaagac cggttacaga     120
ttgttcgacg gtgccgaaga ttacgccaac gaaaagttag ttggtgccgg tgtcaagaag     180
gccattgacg aaggtatcgt caagcgtgaa gacttgttcc ttacctccaa gttgtggaac     240
aactaccacc acccagacaa cgtcgaaaag gccttgaaca aacccttc tgacttgcaa       300
gttgactacg ttgacttgtt cttgatccac ttcccagtca ccttcaagtt cgttccatta     360
gaagaaaagt accccaccag gattctactg tggtaagggtg acaacttcga ctacgaagat    420
gttccaattt tagagacctg gaaggctctt gaaaagttgg tcaaggccgg taagatcagg     480
tctatcggtg tttctaactt cccaggtgct ttgctcttgg acttgttgag aggtgctacc     540
atcaagccat ctgtcttgca agttgaacac cacccatact gcaacaacc aagattgatc     600
gagttcgctc aatcccgtgg tattgctgtc accgcttact cttcgttcgg tcctcaatct     660
ttcgttgaat tgaaccaagg tagagctttg aacacttctc cattgttcga gaacgaaact     720
atcaaggcta tcgctgctaa gcacggtaag tctccagctc aagtcttgtt gagatggtct     780
tcccaaagag gcattgccat cattccaaag tccaacactg tcccatggtt gttggaaaac    840
aaggatgtca acagcttcga cttggacgaa caagatttcg ctgacattgc caagttggac    900
atcaacttga gattcaacga cccatgggac tgggacaaga ttcctatctt cgtctaa       957
```

<210> SEQ ID NO 41
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 41

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
```

```
                35                  40                  45
Ala Asn Glu Lys Leu Val Gly Ala Gly Val Lys Ala Ile Asp Glu
 50                  55                  60
Gly Ile Val Lys Arg Glu Asp Leu Phe Leu Thr Ser Lys Leu Trp Asn
 65                  70                  75                  80
Asn Tyr His His Pro Asp Asn Val Glu Lys Ala Leu Asn Arg Thr Leu
                 85                  90                  95
Ser Asp Leu Gln Val Asp Tyr Val Asp Leu Phe Leu Ile His Phe Pro
            100                 105                 110
Val Thr Phe Lys Phe Val Pro Leu Glu Glu Lys Tyr Pro Pro Gly Phe
        115                 120                 125
Tyr Cys Gly Lys Gly Asp Asn Phe Asp Tyr Glu Asp Val Pro Ile Leu
    130                 135                 140
Glu Thr Trp Lys Ala Leu Glu Lys Leu Val Lys Ala Gly Lys Ile Arg
145                 150                 155                 160
Ser Ile Gly Val Ser Asn Phe Pro Gly Ala Leu Leu Leu Asp Leu Leu
                165                 170                 175
Arg Gly Ala Thr Ile Lys Pro Ser Val Leu Gln Val Glu His His Pro
            180                 185                 190
Tyr Leu Gln Gln Pro Arg Leu Ile Glu Phe Ala Gln Ser Arg Gly Ile
        195                 200                 205
Ala Val Thr Ala Tyr Ser Ser Phe Gly Pro Gln Ser Phe Val Glu Leu
    210                 215                 220
Asn Gln Gly Arg Ala Leu Asn Thr Ser Pro Leu Phe Glu Asn Glu Thr
225                 230                 235                 240
Ile Lys Ala Ile Ala Ala Lys His Gly Lys Ser Pro Ala Gln Val Leu
                245                 250                 255
Leu Arg Trp Ser Ser Gln Arg Gly Ile Ala Ile Pro Lys Ser Asn
            260                 265                 270
Thr Val Pro Trp Leu Leu Glu Asn Lys Asp Val Asn Ser Phe Asp Leu
        275                 280                 285
Asp Glu Gln Asp Phe Ala Asp Ile Ala Lys Leu Asp Ile Asn Leu Arg
    290                 295                 300
Phe Asn Asp Pro Trp Asp Trp Asp Lys Ile Pro Ile Phe Val
305                 310                 315

<210> SEQ ID NO 42
<211> LENGTH: 957
<212> TYPE: DNA
<213> ORGANISM: Artificial sequence
<220> FEATURE:
<223> OTHER INFORMATION: Synthetic DNA

<400> SEQUENCE: 42
atgacctcta ttaagttgaa ctctggttac gacatgccag ccgtcggttt cggctgttgg      60
aaagttgacg ttgacacctg ttctgaacag gtctaccgtg ctatcaagac cggttacaga     120
ttgttcgacg gtgccgaaga ttacggcaac gaaaagttag ttggtgccgg tgtcaagaag     180
gccattgacg aaggtatcgt caagcgtgaa gacttgttcc ttacctccaa gttgtggaac     240
aactaccacc acccagacaa cgtcgaaaag gccttgaaca gaacccttc tgacttgcaa      300 gttgactacg ttgacttgtt cttgatccac ttcccagtca ccttcaagtt cgttccatta     360
gaagaaaagt acccaccagg attctactgt ggtaagggtg acaacttcga ctacgaagat     420
gttccaattt tagagacctg gaaggctctt gaaaagttgg tcaaggccgg taagatcagg     480
tctatcggtg tttctaactt cccaggtgct ttgctcttgg acttgttgag aggtgctacc     540
```

-continued

```
atcaagccat ctgtcttgca agttgaacac cacccatact tgcaacaacc aagattgatc    600
gagttcgctc aatcccgtgg tattgctgtc accgcttact cttcgttcgg tcctcaatct    660
ttcgttgaat tgaaccaagg tagagctttg aacacttctc cattgttcga gaacgaaact    720
atcaaggcta tcgctgctaa gcacggtaag tctccagctc aagtcttgtt gagatggtct    780
tcccaaagag gcattgccat cattccaaag tccaacactg tcccatggtt gttggaaaac    840
aaggatgtca acagcttcga cttggacgaa caagatttcg ctgacattgc caagttggac    900
atcaacttga gattcaacga cccatgggac tgggacaaga ttcctatctt cgtctaa      957
```

<210> SEQ ID NO 43
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 43

```
Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
```

```
                 290                 295                 300

Phe Asn Asp Pro Trp Asp Trp Asp Lys Ile Pro Ile Phe Val
305                 310                 315

<210> SEQ ID NO 44
<211> LENGTH: 957
<212> TYPE: DNA
<213> ORGANISM: Artificial sequence
<220> FEATURE:
<223> OTHER INFORMATION: Synthetic DNA

<400> SEQUENCE: 44
atgacctcta ttaagttgaa ctctggttac gacatgccag ccgtcggttt cggctgttgg      60
aaagttgacg ttgacacctg ttctgaacag gtctaccgag ctatcaagac cggttacaga     120
ttgttcgacg gtgccgaaga ttacggcaac gaaaaattag ttggtgccgg tgtcaagaag     180
gccattgacg aaggtatcgt caagcgtgaa gacttgttcc ttacctccaa gttgtggaac     240
aactaccacc acccagacaa cgtcgaaaag gccttgaaca gaacccttc tgacttgcaa      300 gttgactacg ttgacttgtt cttgatccac ttcccagtca ccttcaagtt cgttccatta     360
gaagaaaagt acccaccagg attctactgt ggtaacggtg acaacttcga ctacgaagat     420
gttccaattt tagagacctg gaaggctctt gaaaagttgg tcaaggccgg taagatcagg     480
tctatcggtg tttctaactt cccaggtgct ttgctcttgg acttgttgag aggtgctacc     540
atcaagccat ctgtcttgca agttgaacac cacccatact tgcaacaacc aagattgatc     600
gagttcgctc aatcccgtgg tattgctgtc accgcttact cttcgttcgg tcctcaatct     660
ttcgttgaat tgaaccaagg tagagctttg aacactaagc cattgttcga gaacgaaact     720
atcaaggcta tcgctgctaa gcacggcaag agcccagctc aagtcttgtt gagatggtct     780
tcccaaagag gcattgccgt tattccaaag tccaacactg tcccatggtt gttggaaaac     840
aaggatgtca acagcttcga cttggacgaa caagatttcg ctgacattgc caagttggac     900
atcaacttga gattcaacga cccatgggac tgggacaaga ttcctatctt cgtctaa      957

<210> SEQ ID NO 45
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 45

Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125
```

Tyr Cys Gly Asn Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
                180                 185                 190

Tyr Leu Gln Gln Pro Arg Leu Ile Glu Phe Ala Gln Ser Arg Gly Ile
            195                 200                 205

Ala Val Thr Ala Tyr Ser Ser Phe Gly Pro Gln Ser Phe Val Glu Leu
        210                 215                 220

Asn Gln Gly Arg Ala Leu Asn Thr Lys Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Val Ile Pro Lys Ser Asn
                260                 265                 270

Thr Val Pro Trp Leu Leu Glu Asn Lys Asp Val Asn Ser Phe Asp Leu
            275                 280                 285

Asp Glu Gln Asp Phe Ala Asp Ile Ala Lys Leu Asp Ile Asn Leu Arg
        290                 295                 300

Phe Asn Asp Pro Trp Asp Trp Asp Lys Ile Pro Ile Phe Val
305                 310                 315

<210> SEQ ID NO 46
<211> LENGTH: 957
<212> TYPE: DNA
<213> ORGANISM: Artificial sequence
<220> FEATURE:
<223> OTHER INFORMATION: Synthetic DNA

<400> SEQUENCE: 46

| | | | | |
|---|---|---|---|---|
| atgccttcta ttaagttgaa ctctggttac gacatgccag ccgtcggttt cggctgttgg | 60 |
| aaagttgacg ttgacaccctg ttctgaacag gtctaccgtg ctatcaagac cggttacaga | 120 |
| ttgttcgacg gtgccgaaga ttacgccaac gaaaagttag ttggtgccgg tgtcaagaag | 180 |
| gccattgacg aaggtatcgt caagcgtgaa gacttgttcc ttacctccaa gttgtggaac | 240 |
| aactaccacc acccagacaa cgtcgaaaag gccttgaaca gaacccttc tgacttgcaa | 300 |
| gttgactacg ttgacttgtt cttgatccac ttcccagtca ccttcaagtt cgttccatta | 360 |
| gaagaaaagt acccaccagg attctactgt ggtaagggtg acaacttcga ctacgaagat | 420 |
| gttccaattt tagagacctg gaaggctctt gaaaagttgg tcaaggccgg taagatcagg | 480 |
| tctatcggtg tttctaactt cccaggtgct ttgctcttgg acttgttgag aggtgctacc | 540 |
| atcaagccat ctgtcttgca agttgaacac cacccatact gcaacaacc aagattgatc | 600 |
| gagttcgctc aatcccgtgg tattgctgtc accgcttact cttcgttcgg tcctcaatct | 660 |
| ttcgttgaat tgaaccaagg tagagctttg aacacttctc cattgttcga gaacgaaact | 720 |
| atcaaggcta tcgctgctaa gcacggtaag tctccagctc aagtcttgtt gagatggtct | 780 |
| tcccaaagag gcattgccat cattccaaag agcaatactg tcccattctt gttggaaaac | 840 |
| aaggatgtca acagcttcga cttggacgaa caagatttcg ctgacattgc caagttggac | 900 |
| atcaacttga gattcaacga cccatgggac tgggacaaga ttcctatctt cgtctaa | 957 |

<210> SEQ ID NO 47
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 47

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Pro Lys Ser Asn
            260                 265                 270

Thr Val Pro Phe Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 48
<211> LENGTH: 1092
<212> TYPE: DNA
<213> ORGANISM: Artificial sequence
<220> FEATURE:
<223> OTHER INFORMATION: Synthetic DNA

<400> SEQUENCE: 48
atgaccgcta atccctctct tgttttgaat aagattgacg acatttcttt tgaaacttac    60

```
gatgctcccg aaattagcga acccacagac gttttagttc aagttaaaaa aactggtatc    120
tgcggttctg acatccactt ctacgctcat ggaaggatcg gcaacttcgt cttaacaaag    180
ccaatggttc tgggtcatga aagcgcgggt actgttgttc aagtcggtaa aggtgttact    240
tcactgaagg ttggtgataa cgtcgcaatc gagcccggta ttccatctag gttcagtgat    300
gagtacaaat ctggtcacta caacctgtgt ccacacatgg catttgctgc tactcccaat    360
tctaaagagg gtgaaccaaa cccaccagga actctatgta agtacttcaa atctccagaa    420
gacttcctgg ttaagttacc cgatcatgtt tctttggagt tgggtgcttt ggtcgagcca    480
ctatctgttg gggtccatgc tagtaaatta ggctccgttg catttggcga ttacgttgct    540 gttttttggtg ctggtccagt aggattactg gctgccgctg tcgctaagac atttggtgcc    600
aagggtgtga ttgtcgttga tatatctgac aagaagctga agatggccaa agacataggt    660
gccgctacac ataccttcaa ctccaagacg ggaggtagtg aagaattgat caaagccttc    720
ggtggtaatg taccaaatgt tgtcttggaa tgtactgggg ctgaaccatg tattaagcta    780
ggtgttgatg ccatcgcacc aggtggtaga ttcgtgcaag ttggtaatgc tgctggtccc    840 gtgtccttc ccataacagt gttcgctatg aaagaactta ctttgtttgg ttcatttcgt    900
tatggtttca cgactataa gacagccgtg gtatctttg atactaacta ccagaacggt    960
agagagaatg ctcccattga ctttgaacag cttatcacgc acagatacaa attcaaagac   1020
gccattgaag cctacgacct agtaagagca ggtaaggggg ctgtcaagtg tttgattgat   1080
ggtccagaat aa                                                      1092
```

<210> SEQ ID NO 49
<211> LENGTH: 363
<212> TYPE: PRT
<213> ORGANISM: Artificial sequence
<220> FEATURE:
<223> OTHER INFORMATION: Synthetic polypeptide

<400> SEQUENCE: 49

```
Met Thr Ala Asn Pro Ser Leu Val Leu Asn Lys Ile Asp Asp Ile Ser
1               5                  10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175
```

```
Asp Tyr Val Ala Val Phe Gly Ala Gly Pro Val Gly Leu Leu Ala Ala
                180                 185                 190
Ala Val Ala Lys Thr Phe Gly Ala Lys Gly Val Ile Val Val Asp Ile
            195                 200                 205
Ser Asp Lys Lys Leu Lys Met Ala Lys Asp Ile Gly Ala Ala Thr His
210                 215                 220
Thr Phe Asn Ser Lys Thr Gly Gly Ser Glu Glu Leu Ile Lys Ala Phe
225                 230                 235                 240
Gly Gly Asn Val Pro Asn Val Val Leu Glu Cys Thr Gly Ala Glu Pro
                245                 250                 255
Cys Ile Lys Leu Gly Val Asp Ala Ile Ala Pro Gly Gly Arg Phe Val
            260                 265                 270
Gln Val Gly Asn Ala Ala Gly Pro Val Ser Phe Pro Ile Thr Val Phe
        275                 280                 285
Ala Met Lys Glu Leu Thr Leu Phe Gly Ser Phe Arg Tyr Gly Phe Asn
    290                 295                 300
Asp Tyr Lys Thr Ala Val Gly Ile Phe Asp Thr Asn Tyr Gln Asn Gly
305                 310                 315                 320
Arg Glu Asn Ala Pro Ile Asp Phe Glu Gln Leu Ile Thr His Arg Tyr
                325                 330                 335
Lys Phe Lys Asp Ala Ile Glu Ala Tyr Asp Leu Val Arg Ala Gly Lys
            340                 345                 350
Gly Ala Val Lys Cys Leu Ile Asp Gly Pro Glu
        355                 360
```

<210> SEQ ID NO 50
<211> LENGTH: 957
<212> TYPE: DNA
<213> ORGANISM: Artificial sequence
<220> FEATURE:
<223> OTHER INFORMATION: Synthetic DNA

<400> SEQUENCE: 50

```
atgccttcta ttaagttgaa ctctggttac gacatgccag ccgtcggttt cggctgttgg     60
aaagttgacg ttgacacctg ttctgaacag gtctaccgtg ctatcaagac cggttacaga    120
ttgttcgacg gtgccgaaga ttacgccaac gaaaagttag ttggtgccgg tgtcaagaag    180
gccattgacg aaggtatcgt caagcgtgaa gacttgttcc ttacctccaa gttgtggaac    240
aactaccacc acccagacaa cgtcgaaaag gccttgaaca gaacccttc tgacttgcaa    300
gttgactacg ttgacttgtt cttgatccac ttcccagtca ccttcaagtt cgttccatta    360
gaagaaaagt acccaccagg attctactgt ggtaagggtg acaacttcga ctacgaagat    420
gttccaattt tagagacctg gaaggctctt gaaaagttgg tcaaggccgg taagatcagg    480
tctatcggtg tttctaactt cccaggtgct tgctcttgg acttgttgag aggtgctacc    540
atcaagccat ctgtcttgca agttgaacac cacccatact tgcaacaacc aagattgatc    600
gagttcgctc aatcccgtgg tattgctgtc accgcttact cttcgttcgg tcctcaatct    660
ttcgttgaat tgaaccaagg tagagctttg aacacttctc cattgttcga gaacgaaact    720
atcaaggcta tcgctgctaa gcacggtaag tctccagctc aagtcttgtt gagatggtct    780
tcccaaagag gcattgccat cattccaaag agcaatactg tcccattctt gttggaaaac    840
aaggatgtca acagcttcga cttggacgaa caagatttcg ctgacattgc caagttggac    900
atcaacttga gattcaacga cccatgggac tgggacaaga ttcctatctt cgtctaa      957
```

<210> SEQ ID NO 51

<211> LENGTH: 318
<212> TYPE: PRT
<213> ORGANISM: Artificial sequence
<220> FEATURE:
<223> OTHER INFORMATION: Synthetic polypeptide

<400> SEQUENCE: 51

```
Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Phe Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315
```

<210> SEQ ID NO 52
<211> LENGTH: 1092
<212> TYPE: DNA
<213> ORGANISM: Artificial sequence
<220> FEATURE:
<223> OTHER INFORMATION: Synthetic DNA

<400> SEQUENCE: 52
atgaccgcta atccctctct tgttttgaat aagattgacg acatttcttt tgaaacttac    60

```
gatgctcccg aaattagcga acccacagac gttttagttc aagttaaaaa aactggtatc    120
tgcggttctg acatccactt ctacgctcat ggaaggatcg gcaacttcgt cttaacaaag    180
ccaatggttc tgggtcatga aagcgcgggt actgttgttc aagtcggtaa aggtgttact    240
tcactgaagg ttggtgataa cgtcgcaatc gagcccggta ttccatctag gttcagtgat    300
gagtacaaat ctggtcacta caacctgtgt ccacacatgg catttgctgc tactcccaat    360
tctaaagagg gtgaaccaaa cccaccagga actctatgta agtacttcaa atctccagaa    420
gacttcctgg ttaagttacc cgatcatgtt tctttggagt tgggtgcttt ggtcgagcca    480
ctatctgttg gggtccatgc tagtaaatta ggctccgttg catttggcga ttacgttgct    540
gtttttggtg ctggtccagt aggattactg gctgccgctg tcgctaagac atttggtgcc    600
aagggtgtga ttgtcgttga tatatctgac aagaagctga agatggccaa agacataggt    660
gccgctacac ataccttcaa ctccaagacg ggaggtagtg aagaattgat caaagccttc    720
ggtggtaatg taccaaatgt tgtcttggaa tgtactgggg ctgaaccatg tattaagcta    780
ggtgttgatg ccatcgcacc aggtggtaga ttcgtgcaag ttggtaatgc tgctggtccc    840
gtgtcctttc ccataacagt gttcgctatg aaagaactta ctttgtttgg ttcatttcgt    900
tatggtttca cgactataa gacagccgtg gtatctttg atactaacta ccagaacggt    960
agagagaatg ctcccattga ctttgaacag cttatcacgc acagatacaa attcaaagac   1020
gccattgaag cctacgacct agtaagagca ggtaaagggg ctgtcaagtg tttgattgat   1080
ggtccagaat aa                                                       1092
```

<210> SEQ ID NO 53  
<211> LENGTH: 363  
<212> TYPE: PRT  
<213> ORGANISM: Artificial sequence  
<220> FEATURE:  
<223> OTHER INFORMATION: Synthetic polypeptide

<400> SEQUENCE: 53

```
Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
                20                  25                  30

Val Gln Val Lys Lys Thr Gly Ile Cys Gly Ser Asp Ile His Phe Tyr
            35                  40                  45

Ala His Gly Arg Ile Gly Asn Phe Val Leu Thr Lys Pro Met Val Leu
        50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
                100                 105                 110

Met Ala Phe Ala Ala Thr Pro Asn Ser Lys Glu Gly Glu Pro Asn Pro
            115                 120                 125

Pro Gly Thr Leu Cys Lys Tyr Phe Lys Ser Pro Glu Asp Phe Leu Val
        130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
```

```
                180             185             190
Ala Val Ala Lys Thr Phe Gly Ala Lys Gly Val Ile Val Asp Ile
        195                 200                 205
Ser Asp Lys Lys Leu Lys Met Ala Lys Asp Ile Gly Ala Ala Thr His
    210                 215                 220
Thr Phe Asn Ser Lys Thr Gly Ser Glu Glu Leu Ile Lys Ala Phe
225                 230                 235                 240
Gly Gly Asn Val Pro Asn Val Val Leu Glu Cys Thr Gly Ala Glu Pro
                245                 250                 255
Cys Ile Lys Leu Gly Val Asp Ala Ile Ala Pro Gly Gly Arg Phe Val
            260                 265                 270
Gln Val Gly Asn Ala Ala Gly Pro Val Ser Phe Pro Ile Thr Val Phe
        275                 280                 285
Ala Met Lys Glu Leu Thr Leu Phe Gly Ser Phe Arg Tyr Gly Phe Asn
    290                 295                 300
Asp Tyr Lys Thr Ala Val Gly Ile Phe Asp Thr Asn Tyr Gln Asn Gly
305                 310                 315                 320
Arg Glu Asn Ala Pro Ile Asp Phe Glu Gln Leu Ile Thr His Arg Tyr
                325                 330                 335
Lys Phe Lys Asp Ala Ile Glu Ala Tyr Asp Leu Val Arg Ala Gly Lys
            340                 345                 350
Gly Ala Val Lys Cys Leu Ile Asp Gly Pro Glu
        355                 360

<210> SEQ ID NO 54
<211> LENGTH: 957
<212> TYPE: DNA
<213> ORGANISM: Artificial sequence
<220> FEATURE:
<223> OTHER INFORMATION: Synthetic DNA

<400> SEQUENCE: 54
atgacctcta ttaagttgaa ctctggttac gacatgccag ccgtcggttt cggctgttgg      60
aaagttgacg ttgacacctg ttctgaacag gtctaccgtg ctatcaagac cggttacaga     120
ttgttcgacg gtgccgaaga ttacggcaac gaaaagttag ttggtgccgg tgtcaagaag     180
gccattgacg aaggtatcgt caagcgtgaa gacttgttcc ttacctccaa gttgtggaac     240
aactaccacc acccagacaa cgtcgaaaag gccttgaaca gaacccttc tgacttgcaa     300
gttgactacg ttgacttgtt cttgatccac ttcccagtca ccttcaagtt cgttccatta     360
gaagaaaagt acccaccagg attctactgt ggtaagggtg acaacttcga ctacgaagat     420
gttccaattt tagagacctg gaaggctctt gaaaagttgg tcaaggccgg taagatcagg     480
tctatcggtg tttctaactt cccaggtgct tgctcttgg acttgttgag aggtgctacc     540
atcaagccat ctgtcttgca agttgaacac cacccatact gcaacaacc aagattgatc     600
gagttcgctc aatcccgtgg tattgctgtc accgcttact cttcgttcgg tcctcaatct     660
ttcgttgaat tgaaccaagg tagagctttg aacacttctc cattgttcga gaacgaaact     720
atcaaggcta tcgctgctaa gcacggtaag tctccagctc aagtcttgtt gagatggtct     780
tcccaaagag gcattgccat cattccaaag tccaacactg tcccatggtt gttggaaaac     840
aaggatgtca acagcttcga cttggacgaa caagatttcg ctgacattgc aagttggac     900
atcaacttga gattcaacga cccatgggac tgggacaaga ttcctatctt cgtctaa       957

<210> SEQ ID NO 55
<211> LENGTH: 318
```

<212> TYPE: PRT
<213> ORGANISM: Artificial sequence
<220> FEATURE:
<223> OTHER INFORMATION: Synthetic polypeptide

<400> SEQUENCE: 55

Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315

<210> SEQ ID NO 56
<211> LENGTH: 957
<212> TYPE: DNA
<213> ORGANISM: Artificial sequence
<220> FEATURE:
<223> OTHER INFORMATION: Synthetic DNA

<400> SEQUENCE: 56
atgacctcta ttaagttgaa ctctggttac gacatgccag ccgtcggttt cggctgttgg      60
aaagttgacg ttgacaccct gttctgaaca ggtctaccga gctatcaaga ccggttacag     120

```
ttgttcgacg gtgccgaaga ttacggcaac gaaaaattag ttggtgccgg tgtcaagaag      180
gccattgacg aaggtatcgt caagcgtgaa gacttgttcc ttacctccaa gttgtggaac      240
aactaccacc acccagacaa cgtcgaaaag gccttgaaca gaacccttcc tgacttgcaa      300
gttgactacg ttgacttgtt cttgatccac ttcccagtca ccttcaagtt cgttccatta      360
gaagaaaagt acccaccagg attctactgt ggtaacggtg acaacttcga ctacgaagat      420
gttccaattt tagagacctg gaaggctctt gaaaagttgg tcaaggccgg taagatcagg      480
tctatcggtg tttctaactt cccaggtgct ttgctcttgg acttgttgag aggtgctacc      540
atcaagccat ctgtcttgca agttgaacac cacccatact gcaacaacc aagattgatc      600 gagttcgctc aatcccgtgg tattgctgtc accgcttact cttcgttcgg tcctcaatct      660
ttcgttgaat tgaaccaagg tagagctttg aacactaagc cattgttcga aacgaaact      720 atcaaggcta tcgctgctaa gcacggcaag agcccagctc aagtcttgtt gagatggtct      780
tcccaaagag gcattgccgt tattccaaag tccaacactg tcccatggtt gttggaaaac      840
aaggatgtca acagcttcga cttggacgaa caagatttcg ctgacattgc caagttggac      900
atcaacttga gattcaacga cccatgggac tgggacaaga ttcctatctt cgtctaa       957
```

<210> SEQ ID NO 57
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 57

```
Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

Gly Asn Glu Lys Leu Val Gly Ala Gly Val Lys Ala Ile Asp Glu
    50                  55                  60

Gly Ile Val Lys Arg Glu Asp Leu Phe Leu Thr Ser Lys Leu Trp Asn
65                  70                  75                  80

Asn Tyr His His Pro Asp Asn Val Glu Lys Ala Leu Asn Arg Thr Leu
                85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Asn Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220
```

-continued

Asn Gln Gly Arg Ala Leu Asn Thr Lys Pro Leu Phe Glu Asn Glu Thr
225                 230                 235                 240

Ile Lys Ala Ile Ala Ala Lys His Gly Lys Ser Pro Ala Gln Val Leu
            245                 250                 255

Leu Arg Trp Ser Ser Gln Arg Gly Ile Ala Val Ile Pro Lys Ser Asn
            260                 265                 270

Thr Val Pro Trp Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315

<210> SEQ ID NO 58
<211> LENGTH: 957
<212> TYPE: DNA
<213> ORGANISM: Artificial sequence
<220> FEATURE:
<223> OTHER INFORMATION: Synthetic DNA

<400> SEQUENCE: 58
atgacctcta ttaagttgaa ctctggttac gacatgccag ccgtcggttt cggctgttgg      60
aaagttgacg ttgacacctg ttctgaacag gtctaccgag ctatcaagac cggttacaga    120
ttgttcgacg gtgccgaaga ttacggcaac gaaaaattag ttggtgccgg tgtcaagaag    180
gccattgacg aaggtatcgt caagcgtgaa gacttgttcc ttacctccaa gttgtggaac    240
aactaccacc acccagacaa cgtcgaaaag gccttgaaca gaacccttc tgacttgcaa     300
gttgactacg ttgacttgtt cttgatccac ttcccagtca ccttcaagtt cgttccatta    360
gaagaaaagt acccaccagg attctactgt ggtaacggtg acaacttcga ctacgaagat    420
gttccaattt tagagacctg gaaggctctt gaaaagttgg tcaaggccgg taagatcagg    480
tctatcggtg tttctaactt cccaggtgct tgctcttgg acttgttgag aggtgctacc     540
atcaagccat ctgtcttgca agttgaacac cacccatact tgcaacaacc aagattgatc    600
gagttcgctc aatcccgtgg tattgctgtc accgcttact cttcgttcgg tcctcaatct    660
ttcgttgaat tgaaccaagg tagagctttg aacactaagc cattgttcga gaacgaaact    720
atcaaggcta tcgctgctaa gcacggcaag agcccagctc aagtcttgtt gagatggtct    780
tcccaaagag gcattgccgt tattccaaag tccaacactg tcccatggtt gttggaaaac    840
aaggatgtca acagcttcga cttggacgaa caagatttcg ctgacattgc aagttggac    900
atcaacttga gattcaacga cccatgggac tgggacaaga ttcctatctt cgtctaa       957

<210> SEQ ID NO 59
<211> LENGTH: 318
<212> TYPE: PRT
<213> ORGANISM: Artificial sequence
<220> FEATURE:
<223> OTHER INFORMATION: Synthetic polypeptide

<400> SEQUENCE: 59

Met Thr Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Val Tyr
            20                  25                  30

Arg Ala Ile Lys Thr Gly Tyr Arg Leu Phe Asp Gly Ala Glu Asp Tyr
        35                  40                  45

-continued

```
Gly Asn Glu Lys Leu Val Gly Ala Gly Val Lys Lys Ala Ile Asp Glu
 50                  55                  60
Gly Ile Val Lys Arg Glu Asp Leu Phe Leu Thr Ser Lys Leu Trp Asn
 65                  70                  75                  80
Asn Tyr His His Pro Asp Asn Val Glu Lys Ala Leu Asn Arg Thr Leu
                 85                  90                  95
Ser Asp Leu Gln Val Asp Tyr Val Asp Leu Phe Leu Ile His Phe Pro
                100                 105                 110
Val Thr Phe Lys Phe Val Pro Leu Glu Glu Lys Tyr Pro Pro Gly Phe
                115                 120                 125
Tyr Cys Gly Asn Gly Asp Asn Phe Asp Tyr Glu Asp Val Pro Ile Leu
            130                 135                 140
Glu Thr Trp Lys Ala Leu Glu Lys Leu Val Lys Ala Gly Lys Ile Arg
145                 150                 155                 160
Ser Ile Gly Val Ser Asn Phe Pro Gly Ala Leu Leu Leu Asp Leu Leu
                165                 170                 175
Arg Gly Ala Thr Ile Lys Pro Ser Val Leu Gln Val Glu His His Pro
                180                 185                 190
Tyr Leu Gln Gln Pro Arg Leu Ile Glu Phe Ala Gln Ser Arg Gly Ile
            195                 200                 205
Ala Val Thr Ala Tyr Ser Ser Phe Gly Pro Gln Ser Phe Val Glu Leu
            210                 215                 220
Asn Gln Gly Arg Ala Leu Asn Thr Lys Pro Leu Phe Glu Asn Glu Thr
225                 230                 235                 240
Ile Lys Ala Ile Ala Ala Lys His Gly Lys Ser Pro Ala Gln Val Leu
                245                 250                 255
Leu Arg Trp Ser Ser Gln Arg Gly Ile Ala Val Ile Pro Lys Ser Asn
                260                 265                 270
Thr Val Pro Trp Leu Leu Glu Asn Lys Asp Val Asn Ser Phe Asp Leu
            275                 280                 285
Asp Glu Gln Asp Phe Ala Asp Ile Ala Lys Leu Asp Ile Asn Leu Arg
            290                 295                 300
Phe Asn Asp Pro Trp Asp Trp Asp Lys Ile Pro Ile Phe Val
305                 310                 315
```